United States Patent
Bass et al.

(10) Patent No.: US 10,948,492 B2
(45) Date of Patent: Mar. 16, 2021

(54) PD-L2 BIOMARKERS PREDICTIVE OF PD-1 PATHWAY INHIBITOR RESPONSES IN ESOPHAGOGASTRIC CANCERS

(71) Applicant: Dana-Farber Cancer Institute, Inc., Boston, MA (US)

(72) Inventors: Adam Bass, Somerville, MA (US); Sarah Derks, Boston, MA (US); Gordon J. Freeman, Brookline, MA (US); Scott J. Rodig, Westwood, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/553,225

(22) PCT Filed: Mar. 3, 2016

(86) PCT No.: PCT/US2016/020589
§ 371 (c)(1),
(2) Date: Aug. 24, 2017

(87) PCT Pub. No.: WO2016/144673
PCT Pub. Date: Sep. 15, 2016

(65) Prior Publication Data
US 2018/0238884 A1    Aug. 23, 2018

Related U.S. Application Data

(60) Provisional application No. 62/129,094, filed on Mar. 6, 2015.

(51) Int. Cl.
| | |
|---|---|
| *C07K 14/705* | (2006.01) |
| *G01N 33/574* | (2006.01) |
| *C07K 16/28* | (2006.01) |
| *C12Q 1/6886* | (2018.01) |

(52) U.S. Cl.
CPC ..... *G01N 33/57407* (2013.01); *C07K 14/705* (2013.01); *C07K 16/2827* (2013.01); *C12Q 1/6886* (2013.01); *C07K 2317/76* (2013.01); *G01N 2333/70532* (2013.01); *G01N 2333/70596* (2013.01); *G01N 2800/52* (2013.01)

(58) Field of Classification Search
CPC ........................ G01N 33/57407; C07K 14/705
USPC ...................................... 424/172.1
See application file for complete search history.

(56) References Cited

U.S. PATENT DOCUMENTS

2018/0238884 A1    8/2018   Bass et al.

FOREIGN PATENT DOCUMENTS

| WO | WO-2014/194293 A1 | 12/2014 |
| WO | WO-2014/197369 A1 | 12/2014 |
| WO | WO-2015/026634 A1 | 2/2015 |

OTHER PUBLICATIONS

Pasini et al (J Gastroenterol, 2014, 49: 1453-1466).*
Schauer et al (Clin Cancer Res, 2010, 16(1): 330-337).*
Extended European Search Report and Written Opinion for International Application No. 16762173 dated Jul. 6, 2018.
Extended European Search Report and Written Opinion for European Application No. PCT/US2016020589 dated Jul. 6, 2018.
Herbst et al., "Predictive Correlates of Response to the Anti-PD-L1 Antibody MPDL3280A in Cancer Patients," Nature, 515(7528):563-567 (2014).
Ohigashi et al., "Clinical Significance of Programmed Death-1 Ligand-1 and Programmed Death-1 Ligand-2 Expression in Human Esophageal Cancer," Clinical Cancer Research, 11(8):2947-2953 (2005).
Topallian et al., "Safety Activity, and Immune Correlates of Anti-PD-1 Antibody in Cancer," New England Journal of Medicine, 336(26):2443-2454 (2012).
International Search Report and Written Opinion for International Application No. PCT/US16/20589 dated Jun. 24, 2016.
Koyama et al., "Adaptive Resistance to Therapeutic PD-1 Blockade is Associated with Upregulation of Alternative Immune Checkpoints," Nat Commun, 7(10501): 1-9 (2016).
Winograd et al., "Induction of T-Cell Immunity Overcomes Complete Resistance to PD-1 and CTLA-4 Blockade and Improves Survival in Pancreatic Carcinoma," Cancer Immunol Res, 3(4): 399-411 (2015).
Search Report issued by the European Patent Office in corresponding Application No. EP 16762173.9, dated Nov. 29, 2019.
Wu et al., "MicroRNA Expression Signatures during Malignant Progression from Barrett's Esophagus to Esophageal Adenocarcinoma," Canc Prev Res 6(3):196-205 (2013).
Zou et al., "Inhibitory B7-family molecules in the tumour microenvironment," Nat Revs Immunol 8(6):467-477 (2008).

* cited by examiner

*Primary Examiner* — Sean E Aeder
(74) *Attorney, Agent, or Firm* — Foley Hoag LLP

(57) ABSTRACT

The present invention is based on the identification of novel biomarkers predictive of responsiveness of esophagogastric cancers to inhibitors of the PD-1 pathway.

21 Claims, 10 Drawing Sheets

Specification includes a Sequence Listing.

Figure 2
A
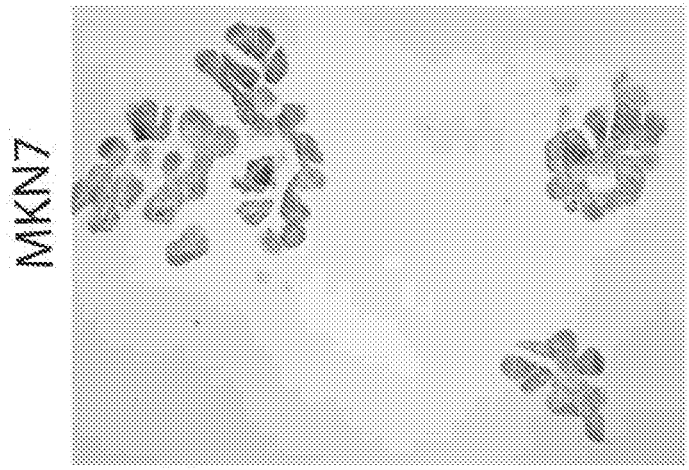
MKN7
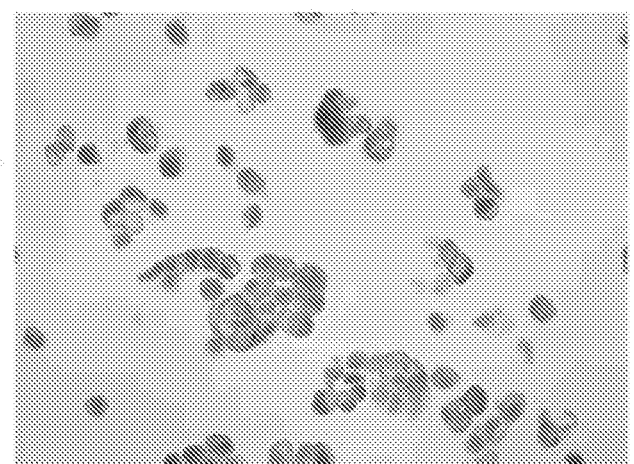
OE33
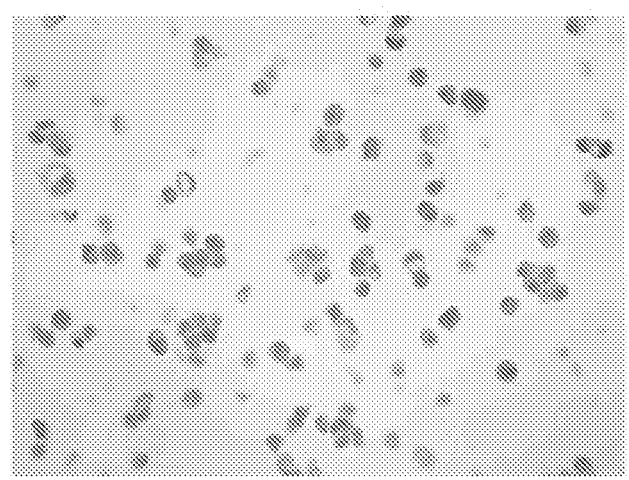
ESO26

Figure 2 (cont.)
A (cont.)
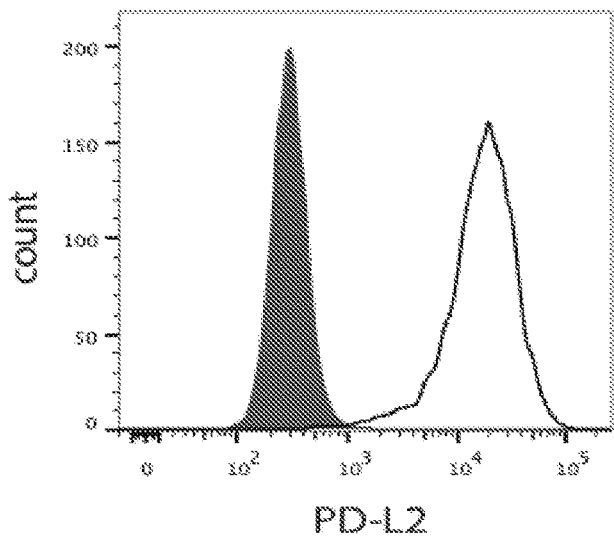
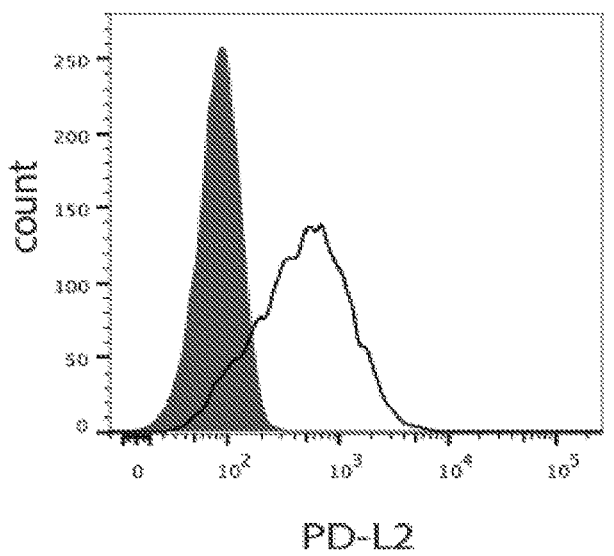
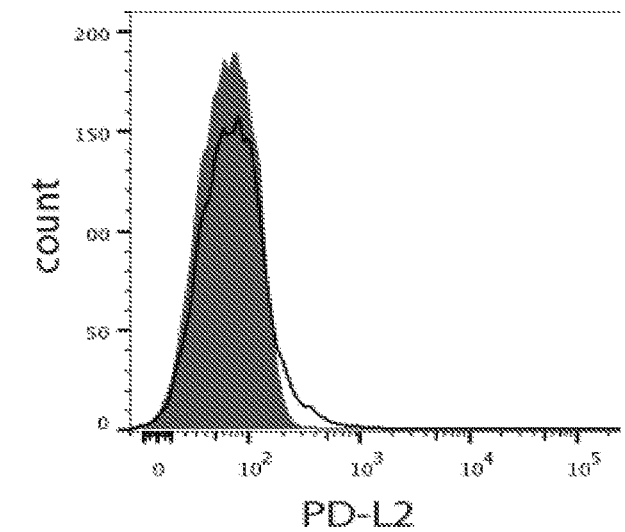

Figure 2 (cont.)
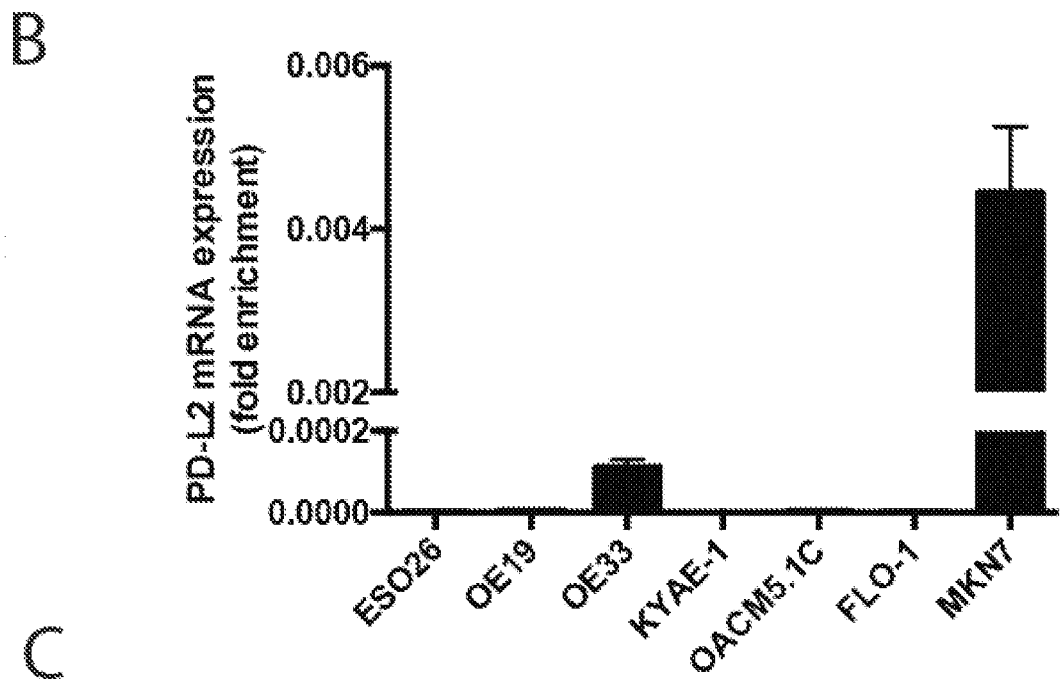
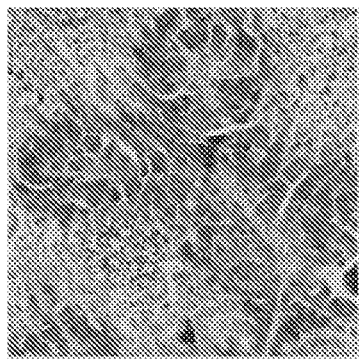
xenograft 1
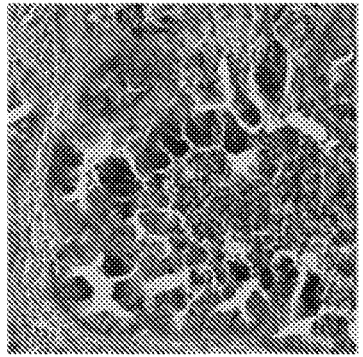
xenograft 6

C (cont.)

Figure 3
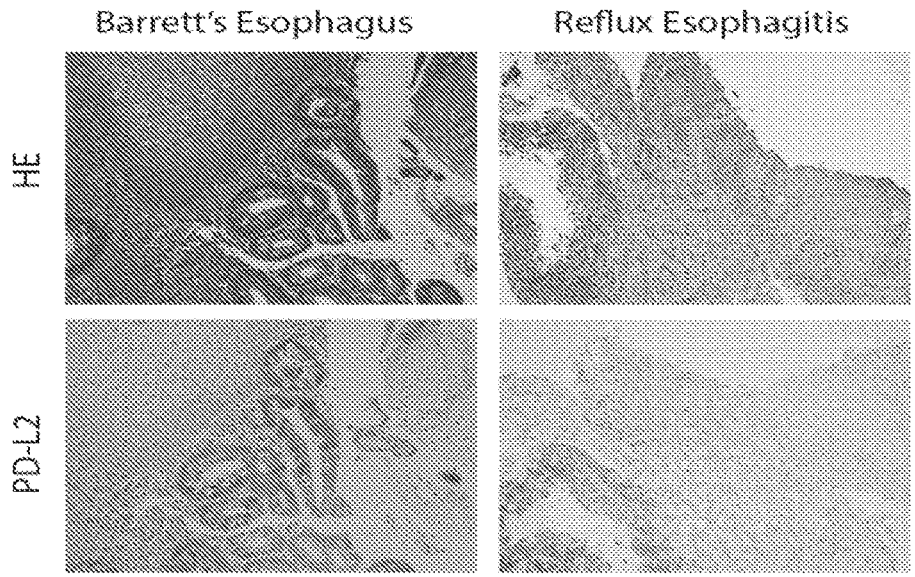
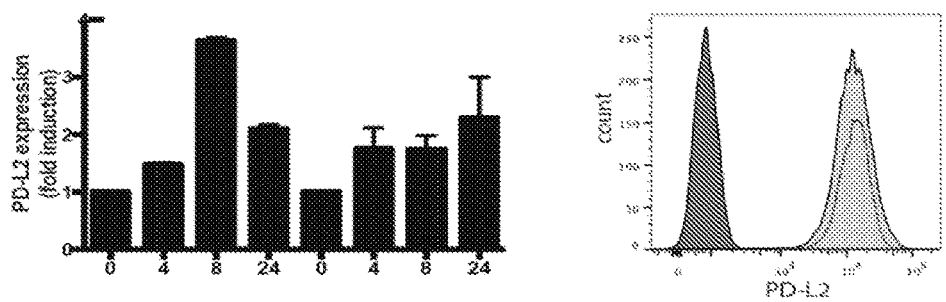
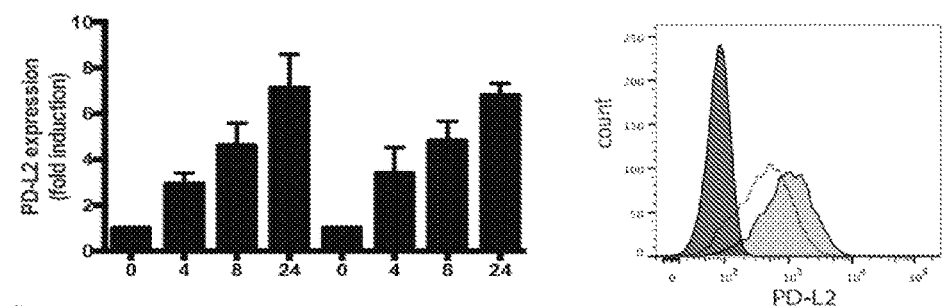
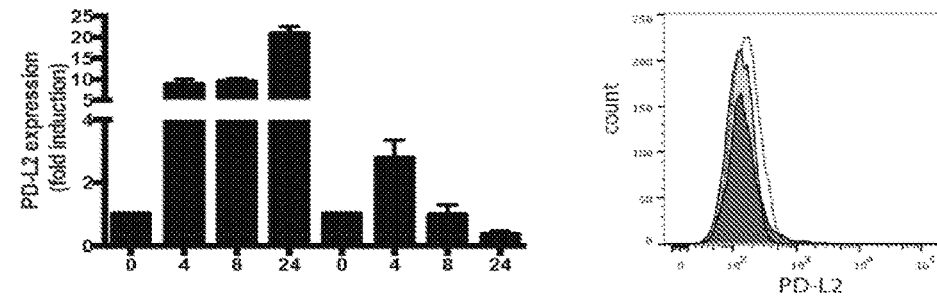

Figure 4
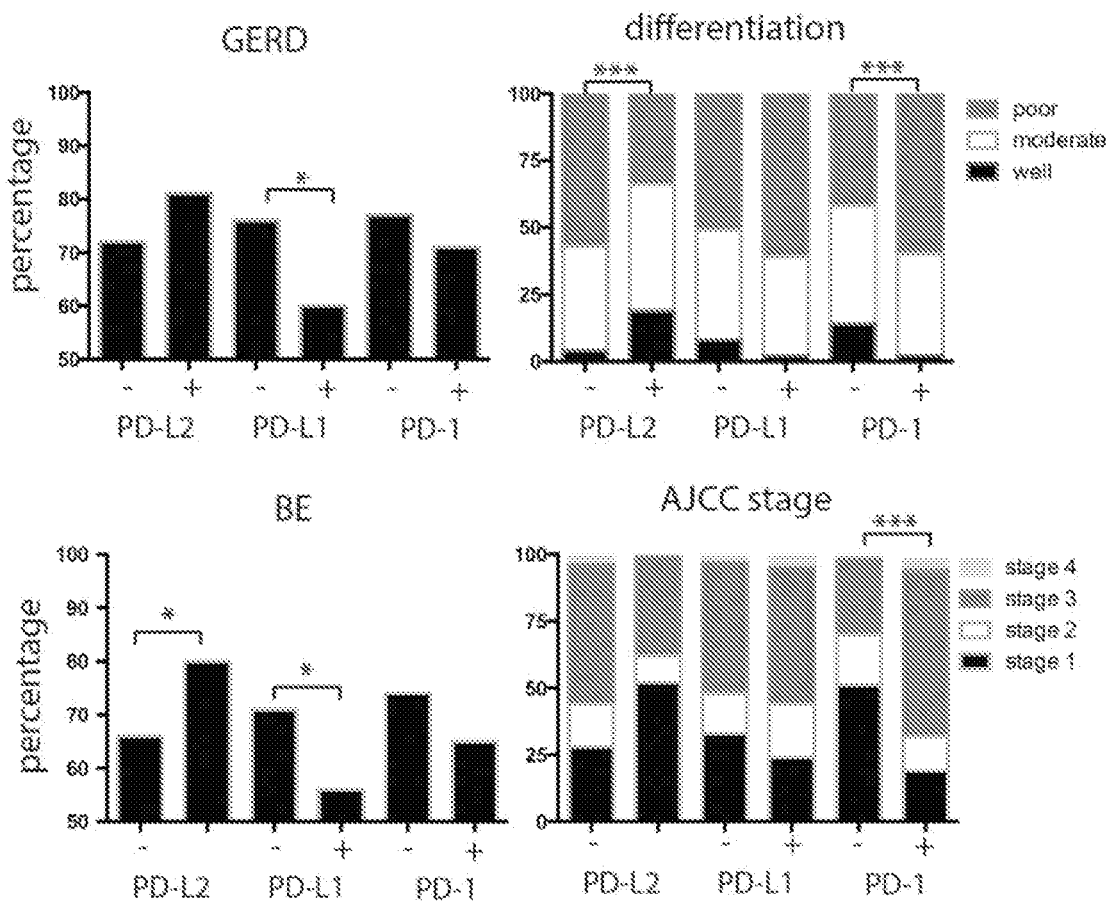
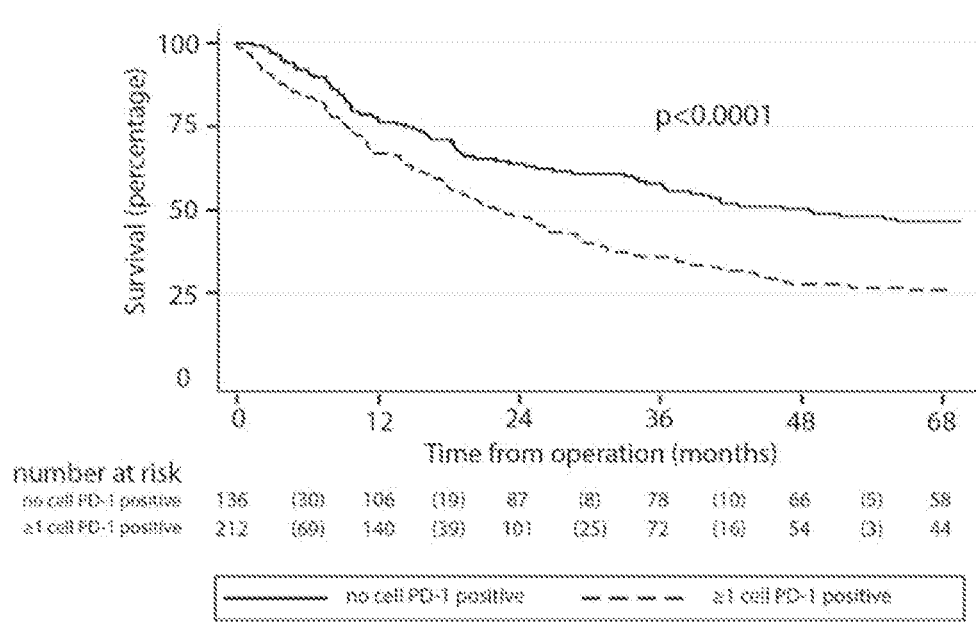

Figure 5

| | | N (%) |
|---|---|---|
| All Cases | | 354 (100) |
| Sex | Female | 62 (17.5) |
| | Male | 292 (82.5) |
| Age | (median, IQR) | 67 (60-75) |
| History of smoking cigarettes | No | 101 (28.9) |
| | Yes | 249 (71.1) |
| History of GERD documented in medical record | No | 92 (26.2) |
| | Yes | 258 (73.8) |
| Histology of Barrett's Esophagus in resection specimen | No | 110 (31.1) |
| | Yes | 244 (68.9) |
| Body Mass Index | (median, IQR) | 27.7 (25.1-31.6) |
| Approach to Esophagectomy | Open | 67 (18.9) |
| | Hybrid | 16 (4.5) |
| | Minimially invasive | 271 (76.6) |
| Charlson Comorbidity Index | Low (CCI 0-1) | 134 (37.8) |
| | Intermediate (CCI 2-5) | 151 (42.7) |
| | High (CCI >5) | 69 (19.5) |
| Tumor Location | Mid/proximal esophagus | 7 (2.0) |
| | Distal esophagus | 96 (27.4) |
| | GE Junction | 247 (70.6) |
| Tumor Stage (AJCC7) | T1 | 138 (39.1) |
| | T2 | 36 (10.2) |
| | T3 | 174 (49.3) |
| | T4 | 5 (1.4) |
| Tumor Size | (median, IQR) | 3.7 (2.4-5.5) |
| Tumor Grade | Well differentiated | 24 (6.8) |
| | Moderately differentiated | 145 (41.0) |
| | Poorly differentiated | 185 (52.2) |
| Node Stage (AJCC7) | N0 | 140 (39.7) |
| | N1 | 80 (22.7) |
| | N2 | 62 (17.6) |
| | N3 | 71 (20) |
| Number of Nodes Examined | (median, IQR) | 20 (14-29) |
| Metastasis Stage | M0 | 341 (96.6) |
| | M1 | 12 (3.4) |
| Final AJCC7 Stage Group | Stage I | 116 (33.0) |
| | Stage II | 53 (15.0) |
| | Stage III | 171 (48.6) |
| | Stage IV | 12 (3.4) |
| IQR; interquartile range, GERD; gastro-esophageal reflux disease | | |
| AJCC; American joint committee on cancer | | |

SEQUENCE LISTING

```
<160> NUMBER OF SEQ ID NOS: 16

<210> SEQ ID NO 1
<211> LENGTH: 819
<212> TYPE: DNA
<213> ORGANISM: Homo sapiens
<220> FEATURE:
<221> NAME/KEY: CDS
<222> LOCATION: (1)..(819)

<400> SEQUENCE: 1 atg atc ttc ctc ctg cta atg ttg agc ctg gaa ttg cag ctt cac cag      48
Met Ile Phe Leu Leu Leu Met Leu Ser Leu Glu Leu Gln Leu His Gln
1               5                   10                  15 ata gca gct tta ttc aca gtg aca gtc cct aag gaa ctg tac ata ata      96
Ile Ala Ala Leu Phe Thr Val Thr Val Pro Lys Glu Leu Tyr Ile Ile
            20                  25                  30 gag cat ggc agc aat gtg acc ctg gaa tgc aac ttt gac act gga agt     144
Glu His Gly Ser Asn Val Thr Leu Glu Cys Asn Phe Asp Thr Gly Ser
        35                  40                  45 cat gtg aac ctt gga gca ata aca gcc agt ttg caa aag gtg gaa aat     192
His Val Asn Leu Gly Ala Ile Thr Ala Ser Leu Gln Lys Val Glu Asn
    50                  55                  60 gat aca tcc cca cac cgt gaa aga gcc act ttg ctg gag gag cag ctg     240
Asp Thr Ser Pro His Arg Glu Arg Ala Thr Leu Leu Glu Glu Gln Leu
65                  70                  75                  80 ccc cta ggg aag gcc tcg ttc cac ata cct caa gtc caa gtg agg gac     288
Pro Leu Gly Lys Ala Ser Phe His Ile Pro Gln Val Gln Val Arg Asp
                85                  90                  95 gaa gga cag tac caa tgc ata atc atc tat ggg gtc gcc tgg gac tac     336
Glu Gly Gln Tyr Gln Cys Ile Ile Ile Tyr Gly Val Ala Trp Asp Tyr
            100                 105                 110 aag tac ctg act ctg aaa gtc aaa gct tcc tac agg aaa ata aac act     384
Lys Tyr Leu Thr Leu Lys Val Lys Ala Ser Tyr Arg Lys Ile Asn Thr
        115                 120                 125 cac atc cta aag gtt cca gaa aca gat gag gta gag ctc acc tgc cag     432
His Ile Leu Lys Val Pro Glu Thr Asp Glu Val Glu Leu Thr Cys Gln
    130                 135                 140 gct aca ggt tat cct ctg gca gaa gta tcc tgg cca aac gtc agc gtt     480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc     528
Pro Ala Asn Thr Ser His Ser Arg Thr Pro Glu Gly Leu Tyr Gln Val
                165                 170                 175
```

```
acc agt gtt ctg cgc cta aag cca ccc cct ggc aga aac ttc agc tgt    576
Thr Ser Val Leu Arg Leu Lys Pro Pro Pro Gly Arg Asn Phe Ser Cys
        180                 185                 190 gtg ttc tgg aat act cac gtg agg gaa ctt act ttg gcc agc att gac    624
Val Phe Trp Asn Thr His Val Arg Glu Leu Thr Leu Ala Ser Ile Asp
            195                 200                 205 ctt caa agt cag atg gaa ccc agg acc cat cca act tgg ctg ctt cac    672
Leu Gln Ser Gln Met Glu Pro Arg Thr His Pro Thr Trp Leu Leu His
    210                 215                 220 att ttc atc ccc tcc tgc atc att gct ttc att ttc ata gcc aca gtg    720
Ile Phe Ile Pro Ser Cys Ile Ile Ala Phe Ile Phe Ile Ala Thr Val
225                 230                 235                 240 ata gcc cta aga aaa caa ctc tgt caa aag ctg tat tct tca aaa gac    768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct    816
Thr Thr Lys Arg Pro Val Thr Thr Thr Lys Arg Glu Val Asn Ser Ala
            260                 265                 270 atc                                                                819
Ile

<210> SEQ ID NO 2
<211> LENGTH: 273
<212> TYPE: PRT
<213> ORGANISM: Homo sapiens

<400> SEQUENCE: 2

Met Ile Phe Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
```

```
               225                 230                 235                 240
Ile Ala Leu Arg Lys Gln Leu Cys Gln Lys Leu Tyr Ser Ser Lys Asp
                    245                 250                 255

Thr Thr Lys Arg Pro Val Thr Thr Lys Arg Glu Val Asn Ser Ala
                    260                 265                 270

Ile

<210> SEQ ID NO 3
<211> LENGTH: 968
<212> TYPE: DNA
<213> ORGANISM: Homo sapiens
<220> FEATURE:
<221> NAME/KEY: CDS
<222> LOCATION: (59)..(793)

<400> SEQUENCE: 3
gcttcccgag gctccgcacc agccgcgctt ctgtccgcct gcagggcatt ccagaaag          58 atg agg ata ttt gct gtc ttt ata ttc atg acc tac tgg cat ttg ctg         106
Met Arg Ile Phe Ala Val Phe Ile Phe Met Thr Tyr Trp His Leu Leu
1               5                  10                  15 aac gca ttt act gtc acg gtt ccc aag gac cta tat gtg gta gag tat        154
Asn Ala Phe Thr Val Thr Val Pro Lys Asp Leu Tyr Val Val Glu Tyr
                20                  25                  30 ggt agc aat atg aca att gaa tgc aaa ttc cca gta gaa aaa caa tta        202
Gly Ser Asn Met Thr Ile Glu Cys Lys Phe Pro Val Glu Lys Gln Leu
            35                  40                  45 gac ctg gct gca cta att gtc tat tgg gaa atg gag gat aag aac att        250
Asp Leu Ala Ala Leu Ile Val Tyr Trp Glu Met Glu Asp Lys Asn Ile
        50                  55                  60 att caa ttt gtg cat gga gag gaa gac ctg aag gtt cag cat agt agc        298
Ile Gln Phe Val His Gly Glu Glu Asp Leu Lys Val Gln His Ser Ser
65                  70                  75                  80 tac aga cag agg gcc cgg ctg ttg aag gac cag ctc tcc ctg gga aat        346
Tyr Arg Gln Arg Ala Arg Leu Leu Lys Asp Gln Leu Ser Leu Gly Asn
                85                  90                  95 gct gca ctt cag atc aca gat gtg aaa ttg cag gat gca ggg gtg tac        394
Ala Ala Leu Gln Ile Thr Asp Val Lys Leu Gln Asp Ala Gly Val Tyr
                100                 105                 110 cgc tgc atg atc agc tat ggt ggt gcc gac tac aag cga att act gtg        442
Arg Cys Met Ile Ser Tyr Gly Gly Ala Asp Tyr Lys Arg Ile Thr Val
            115                 120                 125 aaa gtc aat gcc cca tac aac aaa atc aac caa aga att ttg gtt gtg        490
Lys Val Asn Ala Pro Tyr Asn Lys Ile Asn Gln Arg Ile Leu Val Val
        130                 135                 140 gat cca gtc acc tct gaa cat gaa ctg aca tgt cag gct gag ggc tac        538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt        586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat        634
Gly Lys Thr Thr Thr Thr Asn Ser Lys Arg Glu Glu Lys Leu Phe Asn
                180                 185                 190 gtg acc agc aca ctg aga atc aac aca aca act aat gag att ttc tac        682
Val Thr Ser Thr Leu Arg Ile Asn Thr Thr Thr Asn Glu Ile Phe Tyr
            195                 200                 205 tgc act ttt agg aga tta gat cct gag gaa aac cat aca gct gaa ttg        730
Cys Thr Phe Arg Arg Leu Asp Pro Glu Glu Asn His Thr Ala Glu Leu
        210                 215                 220
```

```
gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt    833
Leu Ser Pro Ser Thr
            245 gaataaatga atgaatgaat aacactatgt ttacaaaata tatcctaatt cctcacctcc   893 attcatccaa accatattgt tacttaataa acattcagca gatatttatg gaataaaaaa   953 aaaaaaaaaa aaaaa                                                    968
```

<210> SEQ ID NO 4
<211> LENGTH: 245
<212> TYPE: PRT
<213> ORGANISM: Homo sapiens

<400> SEQUENCE: 4

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Gly Asn Ile Leu Asn Val Ser Ile Lys Ile Cys Leu Thr
225                 230                 235                 240

Leu Ser Pro Ser Thr
            245
```

<210> SEQ ID NO 5
<211> LENGTH: 1553
<212> TYPE: DNA
<213> ORGANISM: Homo sapiens
<220> FEATURE:
<221> NAME/KEY: CDS
<222> LOCATION: (53)..(922)

<400> SEQUENCE: 5

```
cgaggctccg caccagccgc gcttctgtcc gcctgcaggg cattccagaa ag atg agg       58
                                                         Met Arg
                                                          1 ata ttt gct gtc ttt ata ttc atg acc tac tgg cat ttg ctg aac gca        106
Ile Phe Ala Val Phe Ile Phe Met Thr Tyr Trp His Leu Leu Asn Ala
     5                  10                 15 ttt act gtc acg gtt ccc aag gac cta tat gtg gta gag tat ggt agc        154
Phe Thr Val Thr Val Pro Lys Asp Leu Tyr Val Val Glu Tyr Gly Ser
 20                  25                 30 aat atg aca att gaa tgc aaa ttc cca gta gaa aaa caa tta gac ctg        202
Asn Met Thr Ile Glu Cys Lys Phe Pro Val Glu Lys Gln Leu Asp Leu
 35                  40                 45                  50 gct gca cta att gtc tat tgg gaa atg gag gat aag aac att att caa        250
Ala Ala Leu Ile Val Tyr Trp Glu Met Glu Asp Lys Asn Ile Ile Gln
             55                  60                 65 ttt gtg cat gga gag gaa gac ctg aag gtt cag cat agt agc tac aga        298
Phe Val His Gly Glu Glu Asp Leu Lys Val Gln His Ser Ser Tyr Arg
             70                  75                 80 cag agg gcc cgg ctg ttg aag gac cag ctc tcc ctg gga aat gct gca        346
Gln Arg Ala Arg Leu Leu Lys Asp Gln Leu Ser Leu Gly Asn Ala Ala
         85                  90                 95 ctt cag atc aca gat gtg aaa ttg cag gat gca ggg gtg tac cgc tgc        394
Leu Gln Ile Thr Asp Val Lys Leu Gln Asp Ala Gly Val Tyr Arg Cys
    100                 105                110 atg atc agc tat ggt ggt gcc gac tac aag cga att act gtg aaa gtc        442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca        490
Asn Ala Pro Tyr Asn Lys Ile Asn Gln Arg Ile Leu Val Val Asp Pro
                135                 140                 145 gtc acc tct gaa cat gaa ctg aca tgt cag gct gag ggc tac ccc aag        538
Val Thr Ser Glu His Glu Leu Thr Cys Gln Ala Glu Gly Tyr Pro Lys
             150                 155                160 gcc gaa gtc atc tgg aca agc agt gac cat caa gtc ctg agt ggt aag        586
Ala Glu Val Ile Trp Thr Ser Ser Asp His Gln Val Leu Ser Gly Lys
         165                 170                 175 acc acc acc acc aat tcc aag aga gag gag aag ctt ttc aat gtg acc        634
Thr Thr Thr Thr Asn Ser Lys Arg Glu Glu Lys Leu Phe Asn Val Thr
    180                 185                 190 agc aca ctg aga atc aac aca aca act aat gag att ttc tac tgc act        682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc        730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta        778
Pro Glu Leu Pro Leu Ala His Pro Pro Asn Glu Arg Thr His Leu Val
             230                 235                240 att ctg gga gcc atc tta tta tgc ctt ggt gta gca ctg aca ttc atc        826
Ile Leu Gly Ala Ile Leu Leu Cys Leu Gly Val Ala Leu Thr Phe Ile
         245                 250                 255 ttc cgt tta aga aaa ggg aga atg atg gat gtg aaa aaa tgt ggc atc        874
Phe Arg Leu Arg Lys Gly Arg Met Met Asp Val Lys Lys Cys Gly Ile
    260                 265                 270 caa gat aca aac tca aag aag caa agt gat aca cat ttg gag gag acg        922
Gln Asp Thr Asn Ser Lys Lys Gln Ser Asp Thr His Leu Glu Glu Thr
275                 280                 285                 290 taatccagca ttggaacttc tgatcttcaa gcagggattc tcaacctgtg gtttagggt       982
```

```
tcatcggggc tgagcgtgac aagaggaagg aatgggcccg tgggatgcag gcaatgtggg    1042
acttaaaagg cccaagcact gaaaatggaa cctggcgaaa gcagaggagg agaatgaaga    1102
aagatggagt caaacaggga gcctggaggg agaccttgat actttcaaat gcctgagggg    1162
ctcatcgacg cctgtgacag ggagaaagga tacttctgaa caaggagcct ccaagcaaat    1222
catccattgc tcatcctagg aagacgggtt gagaatccct aatttgaggg tcagttcctg    1282
cagaagtgcc ctttgcctcc actcaatgcc tcaatttgtt ttctgcatga ctgagagtct    1342
cagtgttgga acgggacagt atttatgtat gagttttttcc tatttatttt gagtctgtga    1402
ggtcttcttg tcatgtgagt gtggttgtga atgatttctt ttgaagatat attgtagtag    1462
atgttacaat tttgtcgcca aactaaactt gctgcttaat gatttgctca catctagtaa    1522
aacatggagt atttgtaaaa aaaaaaaaa a                                     1553
```

<210> SEQ ID NO 6
<211> LENGTH: 290
<212> TYPE: PRT
<213> ORGANISM: Homo sapiens

<400> SEQUENCE: 6

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270
```

```
Gly Ile Gln Asp Thr Asn Ser Lys Lys Gln Ser Asp Thr His Leu Glu
        275                 280                 285

Glu Thr
    290

<210> SEQ ID NO 7
<211> LENGTH: 921
<212> TYPE: DNA
<213> ORGANISM: Homo sapiens
<220> FEATURE:
<221> NAME/KEY: CDS
<222> LOCATION: (25)..(888)

<400> SEQUENCE: 7
cactctggtg gggctgctcc aggc atg cag atc cca cag gcg ccc tgg cca          51
                          Met Gln Ile Pro Gln Ala Pro Trp Pro
                            1               5 gtc gtc tgg gcg gtg cta caa ctg ggc tgg cgg cca gga tgg ttc tta         99
Val Val Trp Ala Val Leu Gln Leu Gly Trp Arg Pro Gly Trp Phe Leu
 10              15                  20                  25 gac tcc cca gac agg ccc tgg aac ccc ccc acc ttc tcc cca gcc ctg        147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc        195
Leu Val Val Thr Glu Gly Asp Asn Ala Thr Phe Thr Cys Ser Phe Ser
             45                  50                  55 aac aca tcg gag agc ttc gtg cta aac tgg tac cgc atg agc ccc agc        243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc        291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac        339
Gly Gln Asp Cys Arg Phe Arg Val Thr Gln Leu Pro Asn Gly Arg Asp
 90                  95                 100                 105 ttc cac atg agc gtg gtc agg gcc cgg cgc aat gac agc ggc acc tac        387
Phe His Met Ser Val Val Arg Ala Arg Arg Asn Asp Ser Gly Thr Tyr
                110                 115                 120 ctc tgt ggg gcc atc tcc ctg gcc ccc aag gcg cag atc aaa gag agc        435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca        483
Leu Arg Ala Glu Leu Arg Val Thr Glu Arg Arg Ala Glu Val Pro Thr
        140                 145                 150 gcc cac ccc agc ccc tca ccc agg tca gcc ggc cag ttc caa acc ctg        531
Ala His Pro Ser Pro Ser Pro Arg Ser Ala Gly Gln Phe Gln Thr Leu
    155                 160                 165 gtg gtt ggt gtc gtg ggc ggc ctg ctg ggc agc ctg gtg ctg cta gtc        579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga        627
Trp Val Leu Ala Val Ile Cys Ser Arg Ala Ala Arg Gly Thr Ile Gly
                190                 195                 200 gcc agg cgc acc ggc cag ccc ctg aag gag gac cca tca gcc gtg cct        675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag        723
Val Phe Ser Val Asp Tyr Gly Glu Leu Asp Phe Gln Trp Arg Glu Lys
        220                 225                 230 acc ccg gag ccc ccc gtg ccc tgt gtc cct gag cag acg gag tat gcc        771
```

```
Thr Pro Glu Pro Pro Val Pro Cys Val Pro Glu Gln Thr Glu Tyr Ala
    235                 240                 245 acc att gtc ttt cct agc gga atg ggc acc tca tcc ccc gcc cgc agg    819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat    867
Gly Ser Ala Asp Gly Pro Arg Ser Ala Gln Pro Leu Arg Pro Glu Asp
                270                 275                 280 gga cac tgc tct tgg ccc ctc tgaccggctt ccttggccac cagtgttctg cag    921
Gly His Cys Ser Trp Pro Leu
                285
```

<210> SEQ ID NO 8
<211> LENGTH: 288
<212> TYPE: PRT
<213> ORGANISM: Homo sapiens

<400> SEQUENCE: 8

```
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
                20                  25                  30

Asn Pro Pro Thr Phe Ser Pro Ala Leu Leu Val Val Thr Glu Gly Asp
                35                  40                  45

Asn Ala Thr Phe Thr Cys Ser Phe Ser Asn Thr Ser Glu Ser Phe Val
        50                  55                  60

Leu Asn Trp Tyr Arg Met Ser Pro Ser Asn Gln Thr Asp Lys Leu Ala
65              70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
                100                 105                 110

Ala Arg Arg Asn Asp Ser Gly Thr Tyr Leu Cys Gly Ala Ile Ser Leu
            115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145             150                 155                 160

Arg Ser Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
                180                 185                 190

Ser Arg Ala Ala Arg Gly Thr Ile Gly Ala Arg Arg Thr Gly Gln Pro
            195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225             230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
                260                 265                 270

Ser Ala Gln Pro Leu Arg Pro Glu Asp Gly His Cys Ser Trp Pro Leu
            275                 280                 285
```

<210> SEQ ID NO 9

<211> LENGTH: 1437
<212> TYPE: DNA
<213> ORGANISM: Homo sapiens

<400> SEQUENCE: 9

```
atgataagga agaagaggaa gcgaagcgcg ccccccggcc catgccgcag ccacgggccc    60
agacccgcca cggcgcccgc gccgccgccc tcgccggagc ccacgagacc tgcatggacg   120
ggcatgggct tgagagcagc accttccagc gccgccgctg ccgccgccga ggttgagcag   180
cgccgcagcc ccgggctctg ccccccgccg ctggagctgc tgctgctgct gctgttcagc   240
ctcgggctgc tccacgcagg tgactgccaa cagccagccc aatgtcgaat ccagaaatgc   300
accacggact tcgtgtccct gacttctcac ctgaactctg ccgttgacgg ctttgactct   360
gagttttgca aggccttgcg tgcctatgct ggctgcaccc agcgaacttc aaaagcctgc   420
cgtggcaacc tggtatacca ttctgccgtg ttgggtatca gtgacctcat gagccagagg   480
aattgttcca aggatggacc cacatcctct accaaccccg aagtgaccca tgatccttgc   540
aactatcaca gccacgctgg agccaggaa cacaggagag gggaccagaa ccctcccagt   600
tacctttttt gtggcttgtt tggagatcct cacctcagaa ctttcaagga taacttccaa   660
acatgcaaag tagaagggc ctggccactc atagataata attatctttc agttcaagtg   720
acaaacgtac ctgtggtccc tggatccagt gctactgcta caaataagat cactattatc   780
ttcaaagccc accatgagtg tacagatcag aaagtctacc aagctgtgac agatgacctg   840
ccggccgcct ttgtggatgg caccaccagt ggtggggaca gcgatgccaa gagcctgcgt   900
atcgtggaaa gggagagtgg ccactatgtg agatgcacg cccgctatat agggaccaca   960
gtgtttgtgc ggcaggtggg tcgctacctg acccttgcca tccgtatgcc tgaagacctg  1020
gccatgtcct acgaggagag ccaggacctg cagctgtgcg tgaacggctg ccccctgagt  1080
gaacgcatcg atgacgggca gggccaggtg tctgccatcc tgggacacag cctgcctcgc  1140
acctccttgg tgcaggcctg gcctggctac acactggaga ctgccaacac tcaatgccat  1200
gagaagatgc cagtgaagga catctatttc cagtcctgtg tcttcgacct gctcaccact  1260
ggtgatgcca actttactgc cgcagcccac agtgccttgg aggatgtgga ggccctgcac  1320
ccaaggaagg aacgctggca cattttcccc agcagtggca tgggactccc cgtggaggc   1380
agtgatttgt ctgtcagtct aggactcacc tgcttgatcc ttatcgtgtt tttgtag     1437
```

<210> SEQ ID NO 10
<211> LENGTH: 478
<212> TYPE: PRT
<213> ORGANISM: Homo sapiens

<400> SEQUENCE: 10

```
Met Ile Arg Lys Lys Arg Lys Arg Ser Ala Pro Gly Pro Cys Arg
1               5                   10                  15

Ser His Gly Pro Arg Pro Ala Thr Ala Pro Ala Pro Pro Ser Pro
                20                  25                  30

Glu Pro Thr Arg Pro Ala Trp Thr Gly Met Gly Leu Arg Ala Ala Pro
        35                  40                  45

Ser Ser Ala Ala Ala Ala Ala Glu Val Glu Gln Arg Arg Ser Pro
        50                  55                  60

Gly Leu Cys Pro Pro Leu Glu Leu Leu Leu Leu Leu Leu Phe Ser
65                  70                  75                  80

Leu Gly Leu Leu His Ala Gly Asp Cys Gln Gln Pro Ala Gln Cys Arg
                85                  90                  95
```

```
Ile Gln Lys Cys Thr Thr Asp Phe Val Ser Leu Thr Ser His Leu Asn
            100                 105                 110

Ser Ala Val Asp Gly Phe Asp Ser Glu Phe Cys Lys Ala Leu Arg Ala
        115                 120                 125

Tyr Ala Gly Cys Thr Gln Arg Thr Ser Lys Ala Cys Arg Gly Asn Leu
    130                 135                 140

Val Tyr His Ser Ala Val Leu Gly Ile Ser Asp Leu Met Ser Gln Arg
145                 150                 155                 160

Asn Cys Ser Lys Asp Gly Pro Thr Ser Thr Asn Pro Glu Val Thr
                165                 170                 175

His Asp Pro Cys Asn Tyr His Ser His Ala Gly Ala Arg Glu His Arg
            180                 185                 190

Arg Gly Asp Gln Asn Pro Pro Ser Tyr Leu Phe Cys Gly Leu Phe Gly
        195                 200                 205

Asp Pro His Leu Arg Thr Phe Lys Asp Asn Phe Gln Thr Cys Lys Val
    210                 215                 220

Glu Gly Ala Trp Pro Leu Ile Asp Asn Asn Tyr Leu Ser Val Gln Val
225                 230                 235                 240

Thr Asn Val Pro Val Pro Gly Ser Ser Ala Thr Ala Thr Asn Lys
                245                 250                 255

Ile Thr Ile Ile Phe Lys Ala His His Glu Cys Thr Asp Gln Lys Val
            260                 265                 270

Tyr Gln Ala Val Thr Asp Asp Leu Pro Ala Ala Phe Val Asp Gly Thr
        275                 280                 285

Thr Ser Gly Gly Asp Ser Asp Ala Lys Ser Leu Arg Ile Val Glu Arg
    290                 295                 300

Glu Ser Gly His Tyr Val Glu Met His Ala Arg Tyr Ile Gly Thr Thr
305                 310                 315                 320

Val Phe Val Arg Gln Val Gly Arg Tyr Leu Thr Leu Ala Ile Arg Met
                325                 330                 335

Pro Glu Asp Leu Ala Met Ser Tyr Glu Glu Ser Gln Asp Leu Gln Leu
            340                 345                 350

Cys Val Asn Gly Cys Pro Leu Ser Glu Arg Ile Asp Asp Gly Gln Gly
        355                 360                 365

Gln Val Ser Ala Ile Leu Gly His Ser Leu Pro Arg Thr Ser Leu Val
    370                 375                 380

Gln Ala Trp Pro Gly Tyr Thr Leu Glu Thr Ala Asn Thr Gln Cys His
385                 390                 395                 400

Glu Lys Met Pro Val Lys Asp Ile Tyr Phe Gln Ser Cys Val Phe Asp
                405                 410                 415

Leu Leu Thr Thr Gly Asp Ala Asn Phe Thr Ala Ala His Ser Ala
            420                 425                 430

Leu Glu Asp Val Glu Ala Leu His Pro Arg Lys Glu Arg Trp His Ile
        435                 440                 445

Phe Pro Ser Ser Gly Asn Gly Thr Pro Arg Gly Gly Ser Asp Leu Ser
    450                 455                 460

Val Ser Leu Gly Leu Thr Cys Leu Ile Leu Ile Val Phe Leu
465                 470                 475

<210> SEQ ID NO 11
<211> LENGTH: 21
<212> TYPE: DNA
<213> ORGANISM: Artificial Sequence
<220> FEATURE:
```

-continued

```
<223> OTHER INFORMATION: /note="Description of Artificial Sequence:
      Human PD-L2 forward synthetic primer"

<400> SEQUENCE: 11
ggcagaaact tcagctgtgt g                                              21

<210> SEQ ID NO 12
<211> LENGTH: 20
<212> TYPE: DNA
<213> ORGANISM: Artificial Sequence
<220> FEATURE:
<223> OTHER INFORMATION: /note="Description of Artificial Sequence:
      Human PD-L2 reverse synthetic primer"

<400> SEQUENCE: 12
ggtcctgggt tccatctgac                                                20

<210> SEQ ID NO 13
<211> LENGTH: 20
<212> TYPE: DNA
<213> ORGANISM: Artificial Sequence
<220> FEATURE:
<223> OTHER INFORMATION: /note="Description of Artificial Sequence:
      Human Stat6 forward synthetic primer"

<400> SEQUENCE: 13
ggcatcttct gggtgactgg                                                20

<210> SEQ ID NO 14
<211> LENGTH: 20
<212> TYPE: DNA
<213> ORGANISM: Artificial Sequence
<220> FEATURE:
<223> OTHER INFORMATION: /note="Description of Artificial Sequence:
      Human Stat6 reverse synthetic primer"

<400> SEQUENCE: 14
ggcatcttct gggtgactgg                                                20

<210> SEQ ID NO 15
<211> LENGTH: 24
<212> TYPE: DNA
<213> ORGANISM: Artificial Sequence
<220> FEATURE:
<223> OTHER INFORMATION: /note="Description of Artificial Sequence:
      Human cyclophilin forward synthetic primer"

<400> SEQUENCE: 15
ctcgaataag tttgacttgt gttt                                           24

<210> SEQ ID NO 16
<211> LENGTH: 19
<212> TYPE: DNA
<213> ORGANISM: Artificial Sequence
<220> FEATURE:
<223> OTHER INFORMATION: /note="Description of Artificial Sequence:
      Human cyclophilin reverse synthetic primer"

<400> SEQUENCE: 16
ctaggcatgg gagggaaca                                                 19
```

PD-L2 BIOMARKERS PREDICTIVE OF PD-1 PATHWAY INHIBITOR RESPONSES IN ESOPHAGOGASTRIC CANCERS

CROSS-REFERENCE TO RELATED APPLICATIONS

This application claims the benefit of U.S. Provisional Application No. 62/129,094, filed on 6 Mar. 2015; the entire contents of said application are incorporated herein in their entirety by this reference.

STATEMENT OF RIGHTS

This invention was made with government support under Grant Numbers R01 AI089955 and P01 CA098101 awarded by the National Institutes of Health. The U.S. government has certain rights in the invention. This statement is included solely to comply with 37 C.F.R. § 401.14(a)(f)(4) and should not be taken as an assertion or admission that the application discloses and/or claims only one invention.

BACKGROUND OF THE INVENTION

The incidence of esophagogastric cancers, such as esophageal adenocarcinoma (EAC), has increased dramatically in the Western world in recent decades (Jemal et al. (2011) *CA* 61:69-90). Five-year survival rates are a dismal 10-15% and treatment is largely reliant upon minimally effective cytotoxic chemotherapy (Cunningham et al. (2008) New *Engl. J. Med.* 358:36-46). There have been multiple attempts to use molecularly targeted agents, such as those targeting ERBB2/HER2 and EGFR. To date, only trastuzumab has proven effective, but it benefits only the ~15% of patients with HER2 overexpression (Bang et al. (2010) *Lancet* 376:687-697). There is a pressing need for new EAC therapies.

As EACs harbor a high somatic mutation burden (Dulak et al. (2013) *Nat. Genet.* 45:478-486) and develop in a background of chronic inflammation caused by gastric reflux, EACs are potentially immunogenic tumors and therefore promising candidates for immunotherapy. In response to gastric reflux, the lower esophagus often undergoes metaplasia to an intestinalized epithelium known as Barrett's esophagus (BE). Barrett's metaplasia is associated with a change from an acute (Th1 type) immune response accompanied with IFN-γ expression (Fitzgerald et al. (2002) *Gut* 51:316-322; Moons et al. (2005) *J. Pathol.* 207:269-276) to a Th2 type chronic inflammation with production of IL-4 and IL-13, a transition that potentially induces an immunosuppressive, tumor-promoting environment.

Among the most promising targets in cancer immunology is the programmed cell death protein 1 (PD-1) pathway. PD-1 is a negative co-stimulatory receptor expressed primarily on T-cells after their activation. The interaction of PD-1 with its ligands, programmed cell death ligand 1 or 2 (PD-L1 or PD-L2) inhibits T cell activation (Freeman et al. (2000) *J. Exp. Med.* 192:1027-1034). Expression of PD-L1 on cancer cells and immune cells has been shown to inhibit the T cell antitumor response and permit neoplastic growth. Expression of these ligands by tumor cells has thus been recognized as a powerful tool exploited by cancers to avoid immune clearance. PD-1 or PD-L1 inhibitors in melanoma, lung, and renal cancer have shown marked response rates with stunning durable clinical responses (Topalian et al. (2012) *New Engl.* 1 Med. 366:2443-2454).

Since generally only subpopulations of cancer patients treated with immunotherapies (e.g., blockade of immune checkpoint molecules, such as those of the PD-1 pathway) respond to such treatment, reliable biomarkers that can predict response or resistance to such immunotherapies are therefore critical for stratifying patient populations and selecting patients who will or will not benefit from such immune therapies. Such biomarkers are not currently known for esophagogastric cancers and metaplasias. Accordingly, there is a great need to identify such biomarkers useful for diagnostic, prognostic, and therapeutic purposes.

SUMMARY OF THE INVENTION

The present invention is based, at least in part, on the discovery that PD-L2 expression is a specific biomarker for prediction of response of esophagogastric cancers and/or esophagogastric metaplasia to PD-1 pathway inhibitors, such as inhibitors of PD-1, PD-L2, and PD-L1. It has heretofore been widely recognized that PD-L1 is upregulated in different cancers such as in a variety of solid tumors, whereas PD-L2 expression is largely limited to dendritic cells and macrophages and predominant cancer expression of PD-L2 has only been described for primary mediastinal large B-cell lymphoma (PMBL) (Shi et al. (2014) *Amer. J. Surg. Pathol.* 38:1715-1723). This observed pattern of robust PD-L2 expression by tumor epithelial cells in a majority of esophagogastric cancers and metaplasia and correlation of such expression with PD-1 expression by lymphoid cells in the esphagogastric cancer tumors is unexpected and different from the pattern of expression of PD-1 pathway members in most other cancers.

In one aspect, a method of identifying the likelihood of an esophagogastric cancer or metaplasia in a subject to be responsive to a PD-1 pathway inhibitor is provided, the method comprising: a) obtaining or providing a patient sample from a patient having the esophagogastric cancer or metaplasia; b) measuring the amount or activity of at least one biomarker listed in Table 1 in the subject sample; and c) comparing said amount or activity of the at least one biomarker listed in Table 1 in a control sample, wherein a significantly increased amount or activity of the at least one biomarker listed in Table 1 in the subject sample relative to the control sample identifies the esophagogastric cancer or metaplasia as being more likely to be responsive to the a PD-1 pathway inhibitor and wherein a decreased amount or activity of the at least one biomarker listed in Table 1 in the subject sample relative to the control sample identifies the esophagogastric cancer or metaplasia as being less likely to be responsive to the a PD-1 pathway inhibitor.

In another aspect, a method of identifying the likelihood of an esophagogastric cancer or metaplasia in a subject to be responsive to a PD-1 pathway inhibitor is provided, the method comprising: a) obtaining or providing a patient sample from a patient having the esophagogastric cancer or metaplasia, wherein the sample comprises nucleic acid molecules from the subject; b) determining the copy number of at least one biomarker listed in Table 1 in the sample; and c) comparing said copy number to that of a control sample, wherein an increased copy number of the biomarker in the sample relative to the control sample identifies the esophagogastric cancer or metaplasia as being more likely to be responsive to the a PD-1 pathway inhibitor and wherein a decreased copy number of the biomarker in the sample relative to the control sample identifies the esophagogastric cancer or metaplasia as being less likely to be responsive to the a PD-1 pathway inhibitor.

The methods of the present invention are characterized by many embodiments and each such embodiment can be applied to any method described herein. For example, in one embodiment, the method further comprises recommending, prescribing, or administering a PD-1 pathway inhibitor if the esophagogastric cancer or metaplasia is determined to be likely to be responsive to PD-1 pathway inhibitor therapy or administering anti-cancer therapy other than a PD-1 pathway inhibitor if the esophagogastric cancer or metaplasia is determined to be less likely to be responsive to PD-1 pathway inhibitor therapy. In another embodiment, the anti-cancer therapy is selected from the group consisting of targeted therapy, chemotherapy, radiation therapy, and/or hormonal therapy. In still another embodiment, the control sample is determined from an esophagogastric cancerous, esophagogastric metaplasic, or non-cancerous esophagogastric sample from either the patient or a member of the same species to which the patient belongs. In yet another embodiment, the control sample is a cancerous esophagogastric, metaplasic esophagogastric, or non-cancerous esophagogastric sample from the patient obtained from an earlier point in time than the patient sample, optionally wherein the control sample is obtained before the patient has received PD-1 pathway inhibitor therapy and the patient sample is obtained after the patient has received PD-1 pathway inhibitor therapy. In another embodiment, the control sample comprises cells or does not comprise cells. In still another embodiment, the control sample comprises esophagogastric cancer or metaplasic cells known to be responsive or non-responsive to the PD-1 pathway inhibitor.

In still another aspect, a method of assessing the efficacy of an agent for treating an esophagogastric cancer or metaplasia in a subject that is unlikely to be responsive to a PD-1 pathway inhibitor is provided, comprising: a) detecting in a first subject sample and maintained in the presence of the agent the amount or activity of at least one biomarker listed in Table 1; b) detecting the amount or activity of the at least one biomarker listed in Table 1 in a second subject sample and maintained in the absence of the test compound; and c) comparing the amount or activity of the at least one biomarker listed in Table 1 from steps a) and b), wherein a significantly decreased amount or activity of the at least one biomarker listed in Table 1 in the first subject sample relative to at least one subsequent subject sample, indicates that the agent treats the esophagogastric cancer or metaplasia in the subject.

In yet another aspect, a method of assessing the efficacy of an agent for treating an esophagogastric cancer or metaplasia in a subject or prognosing progression of an esophagogastric cancer or metaplasia in a subject is provided, comprising: a) detecting in a subject sample at a first point in time the amount or activity of at least one biomarker listed in Table 1; b) repeating step a) during at least one subsequent point in time after administration of the agent; and c) comparing the expression and/or activity detected in steps a) and b), wherein a significantly increased amount or activity of the at least one biomarker listed in Table 1 in the first subject sample relative to at least one subsequent subject sample, indicates that the esophagogastric cancer or metaplasia is unlikely to progress or that the agent treats the esophagogastric cancer or metaplasia in the subject.

As stated above, the methods of the present invention are characterized by many embodiments and each such embodiment can be applied to any method described herein. In one embodiment, the subject has undergone treatment, completed treatment, and/or is in remission for the esophagogastric cancer or metaplasia between the first point in time and the subsequent point in time. In another embodiment, the first and/or at least one subsequent sample is selected from the group consisting of ex vivo and in vivo samples. In still another embodiment, the first and/or at least one subsequent sample is obtained from an animal model of the esophagogastric cancer or metaplasia. In yet another embodiment, the first and/or at least one subsequent sample is a portion of a single sample or pooled samples obtained from the subject.

In another aspect, a cell-based assay for screening for agents that have a cytotoxic or cytostatic effect on an esophagogastric cancer or metaplasic cell that is unresponsive to a PD-1 pathway inhibitor comprising, contacting the esophagogastric cancer or metaplasic cell with a test agent, and determining the ability of the test agent to decrease the amount or activity of at least one biomarker listed in Table 1, is provided. In one embodiment, the step of contacting occurs in vivo, ex vivo, or in vitro.

As stated above, the methods and/or assays of the present invention are characterized by many embodiments and each such embodiment can be applied to any method described herein. In one embodiment, the subject sample and/or the control sample has not been contacted with any anti-esophagogastric treatment or PD-1 pathway inhibitor. In another embodiment, the subject has not been administered any anti-esophagogastric treatment or PD-1 pathway inhibitor. In still another embodiment, the method or assay further comprises recommending, prescribing, or administering at least one additional anti-cancer therapeutic agent, optionally wherein the at least one additional anti-cancer therapeutic agent is an immune checkpoint inhibitor. In yet another embodiment, the subject sample is selected from the group consisting of serum, whole blood, plasma, urine, cells, cell lines, resected tissue, and biopsies. In another embodiment, the amount of the at least one biomarker listed in Table 1 is detected using a reagent which specifically binds with the protein. In still another embodiment, the reagent is selected from the group consisting of an antibody, an antibody derivative, and an antibody fragment. In yet another embodiment, the at least one biomarker listed in Table 1 is assessed by detecting the presence in the sample of a transcribed polynucleotide or portion thereof. In another embodiment, the transcribed polynucleotide is an mRNA or a cDNA. In still another embodiment, the step of detecting further comprises amplifying the transcribed polynucleotide. In yet another embodiment, the transcribed polynucleotide is detected by identifying a nucleic acid that anneals with the biomarker nucleic acid, or a portion thereof, under stringent hybridization conditions. In another embodiment, the at least one biomarker listed in Table 1 is PD-L2, or a fragment thereof. In still another embodiment, the PD-1 pathway inhibitor comprises at least one antibody selected from the group consisting of anti-PD-1 antibodies, anti-PD-L1 antibodies, anti-PD-L2 antibodies, and combinations thereof. In yet another embodiment, the PD-1 pathway inhibitor comprises an anti-PD-L2 antibody. In another embodiment, the likelihood of the esophagogastric cancer or metaplasia in the subject to be responsive to a PD-1 pathway inhibitor is the likelihood of at least one criteria selected from the group consisting of cellular proliferation, tumor burden, m-stage, metastasis, progressive disease, clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria. In still another embodiment, the esophagogastric cancer or metaplasia is an esophageal cancer or metaplasia, or a gastric cancer or metaplasia. In yet another embodiment, the esophageal cancer or metaplasia is an esophageal adenocarcinoma or Barrett's esophagus. In another embodiment, the esophageal adenocarcinoma is metastatic. In still another embodiment, the subject is a mammal, such as an animal model of an esophagogastric cancer or metaplasia or a human.

BRIEF DESCRIPTION OF FIGURES

FIG. 3 includes 2 panels, identified as panels A and B, which show that PD-L2 expression is detected at the transition of reflux esophagitis to Barrett's Esophagus and can be induced by IL-4/IL-13. Panel A shows that IHC staining with hematoxylin and (20×) and anti-PD-L2 antibody (20×) identifies PD-L2 expression in Barrett's esophagus and not in reflux esophagitis tissues. Panel B shows induction of PD-L2 mRNA and protein expression of IL-4- and IL-13-treated MKN7, OE33 and FLO-1 cells. A representative experiment is shown. N=3-5. For mRNA expression results, data are depicted as mean+standard deviation. For flow cytometry results, black represents isotype; white and dashed line represents PD-L2 expression 24 hours after adding medium; and grey represents PD-L2 expression 24 hours after IL-4 treatment.

FIG. 4 includes 2 panels, identified as panels A and B, which show clinical and pathologic associations of PD-L2, PD-L1 and PD-1 expression in EAC. Terms used in Panel A include: GERD, gastro-esophageal reflux disease; BE, Barrett's esophagus; and AJCC, American Joint Committee on Cancer. Panel B shows a Kaplan-Meier plot of overall survival stratified by PD-1 expression. PD-1 expression is associated with reduced survival. *P-value<0.05, **P-value<0.001.

FIG. 5 shows clinical and pathological characteristics of esophageal adenocarcinomas analyzed.

FIG. 6 shows associations of PD-L2, PD-L1 and PD-1 expression with demographic, patient, and pathology predictors.

DETAILED DESCRIPTION OF THE INVENTION

Figure 1:
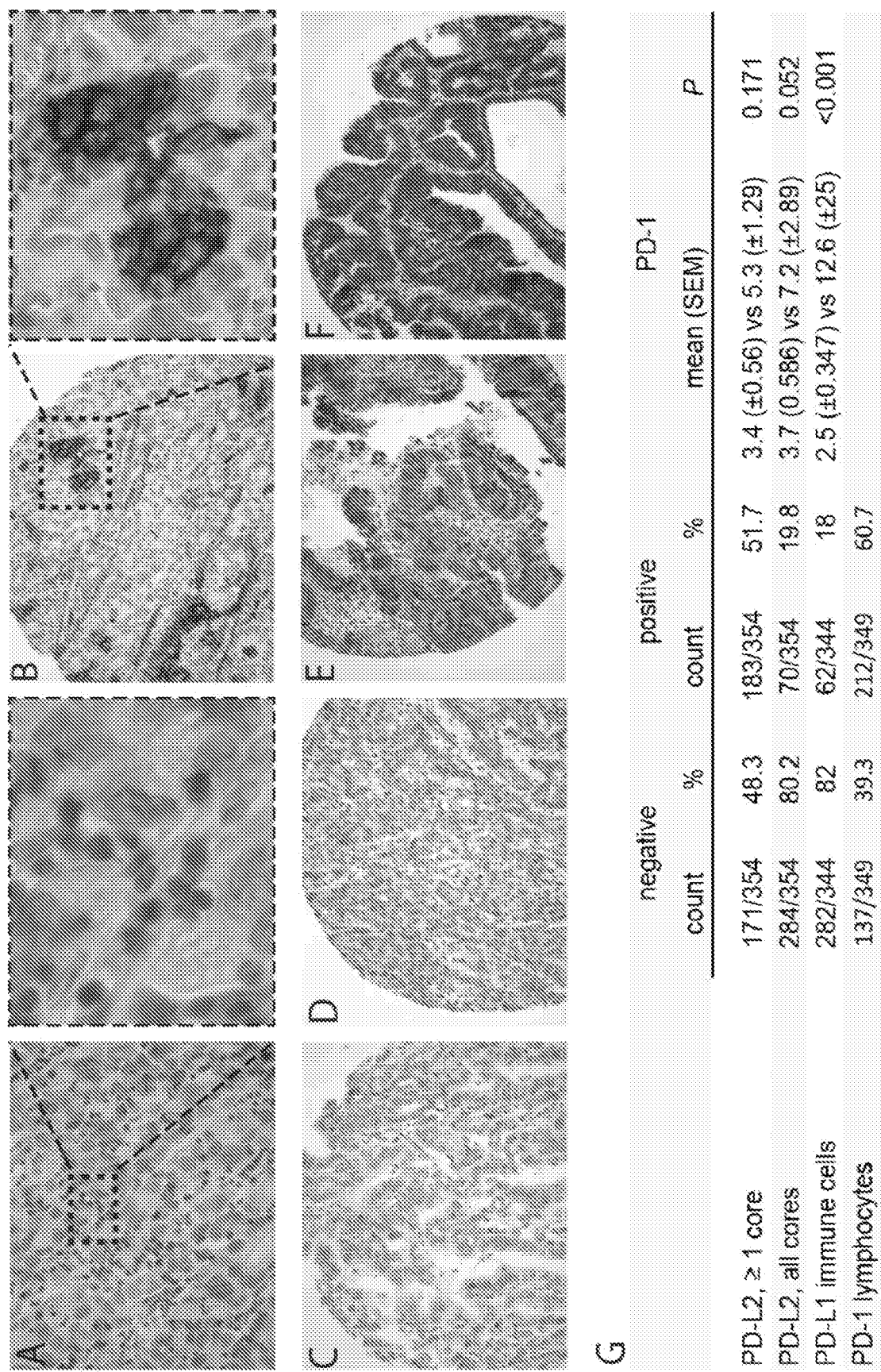
FIG. 1 includes 7 panels, identified as panels A, B, C, D, E, F, and G, which show IHC staining of FFPE esophageal tissues in tissue micro-arrays (20×). Staining with anti-PD-1 antibody showing PD-1 positive TILs (Panel A); anti-PD-L1 antibody in a rare case with positive tumor epithelial staining (Panel B); negative PD-L2 staining (Panel C); weak PD-L2 staining in tumor epithelium scored as 1+ (Panel D); moderate PD-L2 staining scored as 2+ (Panel E), and strong PD-L2 staining scored as 3+ (Panel F). High magnification images to show cytological detail are given for PD-1 and PD-L1. Panel G shows summarized results of PD-L2, PD-L1 and PD-1 positivity for 357 EACs. PD-L2 was scored positive in a core when >50% of the tumor cells showed moderate (2+) or strong (3+) PD-L2 staining of the cell membrane or cytoplasm. PD-L1 and PD-1 were scored positive when any immune cell showed staining. SEM: standard error of mean. The right half of the table compares the number of PD1-positive TILs in cases with and without PD-L2 or PD-L1 positivity. The average number of PD-1 positive TILs is greater in cases scored positive for PD-L2 and PD-L1.

It has been determined herein that certain biomarkers described herein predict clinical outcome in esophagogastric cancer or metaplasia patients (e.g., esophageal adenocarcinoma patients) to PD-1 pathway inhibitor therapy (e.g., blocking antibodies against PD-1, PD-L1, and/or PD-L2, either alone or in combination with other anti-cancer therapeutics such as other immune checkpoint inhibitors). Accordingly, the present invention relates, in part, to methods for stratifying patients and predicting response of an esophagogastric cancer or metaplasia in a subject to PD-1 pathway inhibitory therapy based upon a determination and analysis of biomarkers described herein according to amount (e.g., copy number or level of expression) and/or activity, relative to a control. In addition, such analyses can be used in order to provide useful therapeutic regimens (e.g., based on predictions of clinical response, subject survival or relapse, timing of adjuvant or neoadjuvant treatment, etc.).

I. Definitions

The articles "a" and "an" are used herein to refer to one or to more than one (i.e. to at least one) of the grammatical object of the article. By way of example, "an element" means one element or more than one element.

The term "altered amount" or "altered level" refers to increased or decreased copy number (e.g., germline and/or somatic) of a biomarker nucleic acid, e.g., increased or decreased expression level in a cancer sample, as compared to the expression level or copy number of the biomarker nucleic acid in a control sample. The term "altered amount" of a biomarker also includes an increased or decreased protein level of a biomarker protein in a sample, e.g., a cancer sample, as compared to the corresponding protein level in a normal, control sample. Furthermore, an altered amount of a biomarker protein may be determined by detecting posttranslational modification such as methylation status of the marker, which may affect the expression or activity of the biomarker protein.

The amount of a biomarker in a subject is "significantly" higher or lower than the normal amount of the biomarker, if the amount of the biomarker is greater or less, respectively, than the normal level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternately, the amount of the biomarker in the subject can be considered "significantly" higher or lower than the normal amount if the amount is at least about two, and preferably at least about three, four, or five times, higher or lower, respectively, than the normal amount of the biomarker. Such "significance" can also be applied to any other measured parameter described herein, such as for expression, inhibition, cytotoxicity, cell growth, and the like.

The term "altered level of expression" of a biomarker refers to an expression level or copy number of the biomarker in a test sample, e.g., a sample derived from a patient suffering from cancer, that is greater or less than the standard error of the assay employed to assess expression or copy number, and is preferably at least twice, and more preferably three, four, five or ten or more times the expression level or copy number of the biomarker in a control sample (e.g., sample from a healthy subjects not having the associated disease) and preferably, the average expression level or copy number of the biomarker in several control samples. The altered level of expression is greater or less than the standard error of the assay employed to assess expression or copy number, and is preferably at least 20%, 30%, 40%, 50%, 60%, 70%, 80%, 90%, 100%, 150%, 200%, 300%, 350%, 400%, 500%, 600%, 700%, 800%, 900%, 1000% or more times the expression level or copy number of the biomarker in a control sample (e.g., sample from a healthy subjects not having the associated disease) and preferably, the average expression level or copy number of the biomarker in several control samples.

The term "altered activity" of a biomarker refers to an activity of the biomarker which is increased or decreased in a disease state, e.g., in a cancer sample, as compared to the activity of the biomarker in a normal, control sample. Altered activity of the biomarker may be the result of, for example, altered expression of the biomarker, altered protein level of the biomarker, altered structure of the biomarker, or, e.g., an altered interaction with other proteins involved in the same or different pathway as the biomarker or altered interaction with transcriptional activators or inhibitors.

The term "altered structure" of a biomarker refers to the presence of mutations or allelic variants within a biomarker nucleic acid or protein, e.g., mutations which affect expression or activity of the biomarker nucleic acid or protein, as compared to the normal or wild-type gene or protein. For example, mutations include, but are not limited to substitutions, deletions, or addition mutations. Mutations may be present in the coding or non-coding region of the biomarker nucleic acid.

Unless otherwise specified here within, the terms "antibody" and "antibodies" broadly encompass naturally-occurring forms of antibodies (e.g. IgG, IgA, IgM, IgE) and recombinant antibodies such as single-chain antibodies, chimeric and humanized antibodies and multi-specific antibodies, as well as fragments and derivatives of all of the foregoing, which fragments and derivatives have at least an antigenic binding site. Antibody derivatives may comprise a protein or chemical moiety conjugated to an antibody.

The term "antibody" as used herein also includes an "antigen-binding portion" of an antibody (or simply "antibody portion"). The term "antigen-binding portion", as used herein, refers to one or more fragments of an antibody that retain the ability to specifically bind to an antigen (e.g., a biomarker polypeptide or fragment thereof). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent polypeptides (known as single chain Fv (scFv); see e.g., Bird et al. (1988) *Science* 242:423-426; and Huston et al. (1988) *Proc. Natl. Acad. Sci. USA* 85:5879-5883; and Osbourn et al. 1998, Nature Biotechnology 16: 778). Such single chain antibodies are also intended to be encompassed within the term "antigen-binding portion" of an antibody. Any VH and VL sequences of specific scFv can be linked to human immunoglobulin constant region cDNA or genomic sequences, in order to generate expression vectors encoding complete IgG polypeptides or other isotypes. VH and VL can also be used in the generation of Fab, Fv or other fragments of immunoglobulins using either protein chemistry or recombinant DNA technology. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123).

Still further, an antibody or antigen-binding portion thereof may be part of larger immunoadhesion polypeptides, formed by covalent or noncovalent association of the antibody or antibody portion with one or more other proteins or peptides. Examples of such immunoadhesion polypeptides include use of the streptavidin core region to make a tetrameric scFv polypeptide (Kipriyanov, S. M., et al. (1995) *Human Antibodies and Hybridomas* 6:93-101) and use of a cysteine residue, biomarker peptide and a C-terminal polyhistidine tag to make bivalent and biotinylated scFv polypeptides (Kipriyanov, S. M., et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion polypeptides can be obtained using standard recombinant DNA techniques, as described herein.

Antibodies may be polyclonal or monoclonal; xenogeneic, allogeneic, or syngeneic; or modified forms thereof (e.g. humanized, chimeric, etc.). Antibodies may also be fully human. Preferably, antibodies of the present invention bind specifically or substantially specifically to a biomarker polypeptide or fragment thereof. The terms "monoclonal antibodies" and "monoclonal antibody composition", as used herein, refer to a population of antibody polypeptides that contain only one species of an antigen binding site capable of immunoreacting with a particular epitope of an antigen, whereas the term "polyclonal antibodies" and "polyclonal antibody composition" refer to a population of antibody polypeptides that contain multiple species of antigen binding sites capable of interacting with a particular antigen. A monoclonal antibody composition typically displays a single binding affinity for a particular antigen with which it immunoreacts.

Antibodies may also be "humanized", which is intended to include antibodies made by a non-human cell having variable and constant regions which have been altered to more closely resemble antibodies that would be made by a human cell. For example, by altering the non-human antibody amino acid sequence to incorporate amino acids found in human germline immunoglobulin sequences. The humanized antibodies of the present invention may include amino acid residues not encoded by human germline immunoglobulin sequences (e.g., mutations introduced by random or site-specific mutagenesis in vitro or by somatic mutation in vivo), for example in the CDRs. The term "humanized antibody", as used herein, also includes antibodies in which CDR sequences derived from the germline of another mammalian species, such as a mouse, have been grafted onto human framework sequences.

The term "assigned score" refers to the numerical value designated for each of the biomarkers after being measured in a patient sample. The assigned score correlates to the absence, presence or inferred amount of the biomarker in the sample. The assigned score can be generated manually (e.g., by visual inspection) or with the aid of instrumentation for image acquisition and analysis. In certain embodiments, the assigned score is determined by a qualitative assessment, for example, detection of a fluorescent readout on a graded scale, or quantitative assessment. In one embodiment, an "aggregate score," which refers to the combination of assigned scores from a plurality of measured biomarkers, is determined. In one embodiment the aggregate score is a summation of assigned scores. In another embodiment, combination of assigned scores involves performing mathematical operations on the assigned scores before combining them into an aggregate score. In certain, embodiments, the aggregate score is also referred to herein as the "predictive score."

The term "biomarker" refers to a measurable entity of the present invention that has been determined to be predictive of PD-1 pathway inhibitor therapy effects on a cancer. Biomarkers can include, without limitation, nucleic acids and proteins, including those shown in Table 1, the Examples, and the Figures.

A "blocking" antibody or an antibody "antagonist" is one which inhibits or reduces at least one biological activity of the antigen(s) it binds. In certain embodiments, the blocking antibodies or antagonist antibodies or fragments thereof described herein substantially or completely inhibit a given biological activity of the antigen(s).

The term "body fluid" refers to fluids that are excreted or secreted from the body as well as fluids that are normally not (e.g. amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit).

The terms "cancer" or "tumor" or "hyperproliferative" refer to the presence of cells possessing characteristics typical of cancer-causing cells, such as uncontrolled proliferation, immortality, metastatic potential, rapid growth and proliferation rate, and certain characteristic morphological features. Unless otherwise stated, the terms include metaplasias. In some embodiments, such cells exhibit such characteristics in part or in full due to the expression and activity of immune checkpoint proteins, such as PD-1, PD-L1, and/or CTLA-4. Cancer cells are often in the form of a tumor, but such cells may exist alone within an animal, or may be a non-tumorigenic cancer cell, such as a leukemia cell. As used herein, the term "cancer" includes premalignant as well as malignant cancers. Cancers include, but are not limited to, B cell cancer, e.g., multiple myeloma, Waldenström's macroglobulinemia, the heavy chain diseases, such as, for example, alpha chain disease, gamma chain disease, and mu chain disease, benign monoclonal gammopathy, and immunocytic amyloidosis, melanomas, breast cancer, lung cancer, bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematologic tissues, and the like. Other non-limiting examples of types of cancers applicable to the methods encompassed by the present invention include human sarcomas and carcinomas, e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, colorectal cancer, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, liver cancer, choriocarcinoma, seminoma, embryonal carcinoma, Wilms' tumor, cervical cancer, bone cancer, brain tumor, testicular cancer, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma; leukemias, e.g., acute lymphocytic leukemia and acute myelocytic leukemia (myeloblastic, promyelocytic, myelomonocytic, monocytic and erythroleukemia); chronic leukemia (chronic myelocytic (granulocytic) leukemia and chronic lymphocytic leukemia); and polycythemia vera, lymphoma (Hodgkin's disease and non-Hodgkin's disease), multiple myeloma, Waldenstrom's macroglobulinemia, and heavy chain disease. In some embodiments, cancers are epithlelial in nature and include but are not limited to, bladder cancer, breast cancer, cervical cancer, colon cancer, gynecologic cancers, renal cancer, laryngeal cancer, lung cancer, oral cancer, head and neck cancer, ovarian cancer, pancreatic cancer, prostate cancer, or skin cancer. In other embodiments, the cancer is breast cancer, prostate cancer, lung cancer, or colon cancer. In still other embodiments, the epithelial cancer is non-small-cell lung cancer, nonpapillary renal cell carcinoma, cervical carcinoma, ovarian carcinoma (e.g., serous ovarian carcinoma), or breast carcinoma. The epithelial cancers may be characterized in various other ways including, but not limited to, serous, endometrioid, mucinous, clear cell, Brenner, or undifferentiated.

In certain embodiments, the cancer encompasses esophagogastric cancers. The term "esophagogastric cancers" refers to cancers originating from epithelial cells of the upper alimentary canal including, but not limited to, esophageal cancer, gastric cancer, throat cancer, oral (mouth) cancer, and/or a cancer of the head and/or neck. In some embodiments, the cancer is selected from the group consisting of esophageal cancer, esophageal metaplasia, gastric cancer, and gastric metaplasia. Such cancers are well known in the art, such as described in U.S. Pat. Publ. Nos. 2010/0256630.

In certain embodiments, the cancer is an esophageal cancer or esophageal pre-cancerous lesion (metaplasia). Esophageal cancer is the result of uncontrolled mucosal (epithelial) cell growth in the esophagus. Esophageal cancer is divided into two major types, squamous cell carcinoma and adenocarcinoma. Squamous cell carcinomas develop in the squamous cells that line the esophagus. These cancers normally occur in the upper to middle part of the esophagus. By contrast, adenocarcinomas originate in gland cells not normally a part of the inner lining of the esophagus that replace an area of squamous cells. Esophageal adenocarcinomas typically develop in the glandular tissue in the lower portion of the esophagus in the region where the esophagus and the stomach join.

A representative esophageal pre-cancerous lesion is "Barrett's esophagus." Barrett's esophagus is defined as a change in any length of the esophagealepithelium. When the squamous tissue of the esophagus is replaced by red columnar epithelia, the process is known as metaplasia. The metaplastic columnar epithelia may be of two types: gastric or colonic. Barrett's esophagus is a form of colonic metaplasia. In Barrett's esophagus, the columnar tissue of the stomach extends from the junction of the esophagus and stomach upwards into the esophagus towards the mouth for a variable distance ranging from a few millimeters to nearly the entire length of the esophagus. The metaplasia of Barrett's esophagus may be visible through a gastroscope; however, biopsy specimens of the columnar tissue is typically required to be examined under a microscope in order to properly determine if the cells of the tissue are gastric or colonic in nature. Colonic metaplasia is typically identified by the presence of goblet cells in the epithelium and is necessary for a true diagnosis of Barrett's esophagus. Colonic metaplasia is associated with risk of malignancy in genetically susceptible individuals and can potentially lead to the development of esophageal cancer. It is believed that a chronic reflux of acid or other stomach contents into the esophagus, known as gastroesophageal reflux disease or GERD, leads to damage to the inner lining, or mucosa of the esophagus and causes the inner lining, or mucosa to initiate a natural protective/adaptive process/response of healing that results in the presence of columnar epithelia. Chronic or severe Barrett's esophagus is developed over years, and although it is believed that 10 to 20 million people in the U.S. have acid reflux, only 1 out of 10 people with severe acid reflux problems actually have Barrett's esophagus. Those individuals with Barrett's esophagus typically have a 30 to 40 percent increased risk of developing esophageal cancer.

Staging of esophageal cancer is typically performed according to the TNM system of the American Joint Committee on Cancer (AJCC) available from the American Cancer Society on the World Wide Web at cancer.org. The TNM system is based on several key pieces of information: "T" refers to how far the primary tumor has grown into the wall of the esophagus and into nearby organs; "N" refers to cancer spread to nearby lymph nodes; "M" indicates whether the cancer has metastasized (spread to distant organs); and "G" describes the grade of the cancer, which is based on how the patterns of cancer cells look under a microscope. Staging also takes into account the cell type of the cancer (squamous cell carcinoma or adenocarcinoma). For squamous cell cancers, the location of the tumor can also be a factor in staging.

The T categories describe how deeply the cancer has grown into the wall of the esophagus or into nearby structures. Most esophageal cancers start in the innermost lining of the esophagus (the epithelium) and then grow into deeper layers over time. T categories include the following: TX: The primary tumor can't be assessed; T0: There is no evidence of a primary tumor; Tis: The cancer is only in the epithelium (the top layer of cells lining the inside of the esophagus). It has not started growing into the deeper layers. This stage is also known as high-grade dysplasia. In the past it was called carcinoma in situ; T1: The cancer is growing into the tissue under the epithelium, such as the lamina propria, muscularis mucosa, or submucosa; T1a: The cancer is growing into the lamina propria or muscularis mucosa; T1b: The cancer has grown through the other layers and into the submucosa; T2: The cancer is growing into the thick muscle layer (muscularis propria); T3: The cancer is growing into the outer layer of the esophagus (the adventitia); T4: The cancer is growing into nearby structures; T4a: The cancer is growing into the pleura (the thin layer of tissue covering the lungs), the pericardium (the thin sac surrounding the heart), or the diaphragm (the thin sheet of muscle below the lungs that separates the chest from the abdomen). The cancer can be removed with surgery; and T4b: The cancer cannot be removed with surgery because it has grown into the trachea (windpipe), the aorta (the large blood vessel coming from the heart), the spine, or other crucial structures.

The N categories describe the degree of spreading to lymph nodes. N categories include the following: NX: Nearby lymph nodes can't be assessed; N0: The cancer has not spread to nearby lymph nodes; N1: The cancer has spread to 1 or 2 nearby lymph nodes; N2: The cancer has spread to 3 to 6 nearby lymph nodes; and N3: The cancer has spread to 7 or more nearby lymph nodes.

The M categories describe metastasis status. M categories include the following: M0: The cancer has not spread (metastasized) to distant organs or lymph nodes; and M1: The cancer has spread to distant lymph nodes and/or other organs. Common sites of spread include the liver and lungs.

The G categories described the cancer grade. The grade of a cancer is based on how normal (or differentiated) the cells look under the microscope. The higher the number, the more abnormal the cells look. Higher grade tumors tend to grow and spread faster than lower grade tumors. G categories include the following: GX: The grade cannot be assessed (treated in stage grouping as G1); G1: The cells are well-differentiated; G2: The cells are moderately differentiated; G3: The cells are poorly differentiated; G4: The cells are undifferentiated (these cells are so abnormal that doctors can't tell if they are adenocarcinoma or squamous cell carcinoma). For stage grouping (see below), G4 cancers are grouped with G3 squamous cell cancers.

It is to be noted that some stages of early squamous cell carcinoma also take into account where the tumor is in the esophagus. The location is assigned as either upper, middle, or lower based on where the upper edge of the tumor is.

Once the T, N, M, and G categories have been assigned, this information is combined into an overall stage of 0, I, II, III, or IV. This process is called stage grouping. Some stages are further subdivided into A, B, or C. The stages identify cancers that have a similar prognosis (outlook). Patients with lower stage numbers tend to have a better prognosis. The stage groupings for squamous cell carcinoma and adenocarcinoma are different. Cancers that have features of both squamous cell and adenocarcinoma are staged as squamous cell carcinomas.

Squamous cell carcinoma stages include the following:

Stage 0: Tis, N0, M0, GX or G1; any location: This is the earliest stage of esophageal cancer. It is also called high-grade dysplasia. The cancer cells are found only in the epithelium (the layer of cells lining the esophagus). The cancer has not grown into the connective tissue beneath these cells (Tis). The cancer has not spread to nearby lymph nodes (N0) or other organs (M0). The tumor is well differentiated (G1) or grade information is not available (GX), and it can be anywhere along the esophagus.

Stage IA: T1, N0, M0, GX or G1; any location: The cancer has grown from the epithelium into the layers below, such as the lamina propria, muscularis mucosa, or submucosa, but it has not grown any deeper (T1). It has not spread to nearby lymph nodes (N0) or to distant sites (M0). The tumor is well differentiated (G1) or grade information is not available (GX). It can be anywhere along the esophagus.

Stage IB: Either of the following: T1, N0, M0, G2 or G3; any location: The cancer has grown from the epithelium into the layers below, such as the lamina propria, muscularis mucosa, or submucosa, but it has not grown any deeper (T1). It has not spread to nearby lymph nodes (N0) or to distant sites (M0). It is moderately (G2) or poorly differentiated (G3). The tumor can be anywhere in the esophagus. Alternatively, T2 or T3, N0, M0, GX or G1; location lower: The cancer has grown into the muscle layer called the muscularis propria (T2). It may also have grown through the muscle layer into the adventitia, the connective tissue covering the outside of the esophagus (T3). The cancer has not spread to nearby lymph nodes (N0) or to distant sites (M0). It is well differentiated (G1) or grade information is not available (GX). Its highest point is in the lower part of the esophagus.

Stage IIA: Either of the following: T2 or T3, N0, M0, GX or G1; location upper or middle: The cancer has grown into the muscle layer called the muscularis propria (T2). It may also have grown through the muscle layer into the adventitia, the connective tissue covering the outside of the esophagus (T3). The cancer has not spread to nearby lymph nodes (N0) or to distant sites (M0). The cancer is in the upper or middle part of the esophagus and is well differentiated (G1) or grade information is not available (GX). Alternatively, T2 or T3, N0, M0, G2 or G3; location lower: The cancer has grown into the muscle layer called the muscularis propria (T2). It may also have grown through the muscle layer into the adventitia, the connective tissue covering the outside of the esophagus (T3). The cancer has not spread to lymph nodes (N0) or to distant sites (M0). The cancer is in the lower part of the esophagus and is moderately (G2) or poorly differentiated (G3).

Stage IIB: Either of the following: T2 or T3, N0, M0, G2 or G3; location upper or middle: The cancer has grown into the muscle layer called the muscularis propria (T2). It may also have grown through the muscle layer into the adventitia, the connective tissue covering the outside of the esophagus (T3). The cancer has not spread to nearby lymph nodes (N0) or to distant sites (M0). It is in the upper or middle part of the esophagus and is moderately (G2) or poorly differentiated (G3). Alternatively, T1 or T2, N1, M0, any G; any location: The cancer has grown into the layers below the epithelium, such as the lamina propria, muscularis mucosa, or submucosa (T1). It may also have grown into the muscularis propria (T2). It has not grown through to the outer layer of tissue covering the esophagus. It has spread to 1 or 2 lymph nodes near the esophagus (N1) but has not spread to lymph nodes further away from the esophagus or to distant sites (M0). It can be any grade (G) and can be anywhere along the esophagus.

Stage IIIA: Any of the following: T1 or T2, N2, M0, any G; any location: The cancer has grown into the layers below the epithelium, such as the lamina propria, muscularis mucosa, or submucosa (T1). It may also have grown into the muscularis propria (T2). It has not grown through to the outer layer of tissue covering the esophagus. It has spread to 3 to 6 lymph nodes near the esophagus (N2) but it has not spread to lymph nodes farther away from the esophagus or to distant sites (M0). It can be any grade (G) and can be anywhere along the esophagus. Alternatively, T3, N1, M0, any G; any location: The cancer has grown through the wall of the esophagus to its outer layer, the adventitia (T3). It has spread to 1 or 2 lymph nodes near the esophagus (N1), but it has not spread to lymph nodes farther away from the esophagus or to distant sites (M0). It can be any grade (G) and can be anywhere along the esophagus. Alternatively, T4a, N0, M0, any G; any location: The cancer has grown all the way through the esophagus and into nearby organs or tissues (T4a) but still can be removed. It has not spread to nearby lymph nodes (N0) or to distant sites (M0). It can be any grade (G) and can be anywhere along the esophagus.

Stage IIIB: T3, N2, M0, any G; any location: The cancer has grown through the wall of the esophagus to its outer layer, the adventitia (T3). It has spread to 3 to 6 lymph nodes near the esophagus (N2), but has not spread to lymph nodes farther away from the esophagus or to distant sites (M0). It can be any grade (G) and can be anywhere along the esophagus.

Stage IIIC: Any of the following: T4a, N1 or N2, M0, any G; any location: The cancer has grown all the way through the esophagus and into nearby organs or tissues (T4a) but still can be removed. It has spread to 1 to 6 lymph nodes near the esophagus (N1 or N2), but it has not spread to lymph nodes farther away from the esophagus or to distant sites (M0). It can be any grade (G) and can be anywhere along the esophagus. Alternatively, T4b, any N, M0, any G; any location: The cancer cannot be removed with surgery because it has grown into the trachea (windpipe), the aorta (the large blood vessel coming from the heart), the spine, or other crucial structures (T4b). It may or may not have spread to nearby lymph nodes (any N), but it has not spread to lymph nodes farther away from the esophagus or to distant sites (M0). It can be any grade (G) and can be anywhere along the esophagus. Alternatively, Any T, N3, M0, any G; any location: The cancer has spread to 7 or more nearby lymph nodes (N3), but it has not spread to lymph nodes farther away from the esophagus or to distant sites (M0). It can be any grade and can be anywhere along the esophagus.

Stage IV: Any T, any N, M1, any G; any location: The cancer has spread to distant lymph nodes or other sites (M1). It can be any grade (G) and can be anywhere along the esophagus.

Adenocarcinoma stages include the following. The location of the cancer along the esophagus does not affect the stage of adenocarcinomas.

Stage 0: Tis, N0, M0, GX or G1: This is the earliest stage of esophageal cancer. It is also called high-grade dysplasia. The cancer cells are found only in the epithelium (the layer of cells lining of the esophagus). The cancer has not grown into the connective tissue beneath these cells (Tis). The cancer has not spread to nearby lymph nodes (N0) or other organs (M0). It is well differentiated (G1) or grade information is not available (GX).

Stage IA: T1, N0, M0, GX, G1, or G2: The cancer has grown from the epithelium into the layers below, such as the lamina propria, muscularis mucosa, or submucosa, but it has not grown any deeper (T1). It has not spread to nearby lymph nodes (N0) or to distant sites (M0). It is well (G1) or moderately differentiated (G2), or grade information is not available (GX).

Stage IB: Either of the following: T1, N0, M0, G3: The cancer has grown from the epithelium into the layers below, such as the lamina propria, muscularis mucosa, or submucosa, but it has not grown any deeper (T1). It has not spread to nearby lymph nodes (N0) or to distant sites (M0). It is poorly differentiated (G3). Alternatively, T2, N0, M0, GX, G1, or G2: The cancer has grown into the muscle layer called the muscularis propria (T2). It has not spread to nearby lymph nodes (N0) or to distant sites (M0). It is well (G1) or moderately differentiated (G2), or grade information is not available (GX).

Stage IIA: T2, N0, M0, G3: The cancer has grown into the muscle layer called the muscularis propria (T2). It has not spread to nearby lymph nodes (N0) or to distant sites (M0). It is poorly differentiated (G3).

Stage IIB: Either of the following: T3, N0, M0, any G: The cancer has grown through the wall of the esophagus to its outer layer, the adventitia (T3). It has not spread to nearby lymph nodes (N0) or to distant sites (M0). It can be any grade. Alternatively, T1 or T2, N1, M0, any G: The cancer has grown into the layers below the epithelium, such as the lamina propria, muscularis mucosa, or submucosa (T1). It may also have grown into the muscularis propria (T2). It has not grown through to the outer layer of tissue covering the esophagus. It has spread to 1 or 2 lymph nodes near the esophagus (N1), but it has not spread to lymph nodes farther away from the esophagus or to distant sites (M0). It can be any grade.

Stage IIIA: Any of the following: T1 or T2, N2, M0, any G: The cancer has grown into the layers below the epithelium, such as the lamina propria, muscularis mucosa, or submucosa (T1). It may also have grown into the muscularis propria (T2). It has not grown through to the outer layer of tissue covering the esophagus. It has spread to 3 to 6 lymph nodes near the esophagus (N2) but it has not spread to lymph nodes farther away from the esophagus or to distant sites (M0). It can be any grade (G). Alternatively, T3, N1, M0, any G: The cancer has grown through the wall of the esophagus to its outer layer, the adventitia (T3). It has spread to 1 or 2 lymph nodes near the esophagus (N1), but it has not spread to lymph nodes farther away from the esophagus or to distant sites (M0). It can be any grade (G). Alternatively, T4a, N0, M0, any G: The cancer has grown all the way through the esophagus and into nearby organs or tissues (T4a) but still can be removed. It has not spread to nearby lymph nodes (N0) or to distant sites (M0). It can be any grade (G).

Stage IIIB: T3, N2, M0, any G: The cancer has grown through the wall of the esophagus to its outer layer, the adventitia (T3). It has spread to 3 to 6 lymph nodes near the esophagus (N2), but it has not spread to lymph nodes farther away from the esophagus or to distant sites (M0). It can be any grade (G).

Stage IIIC: Any of the following: T4a, N1 or N2, M0, any G: The cancer has grown all the way through the esophagus and into nearby organs or tissues (T4a) but still can be removed. It has spread to 1 to 6 lymph nodes near the esophagus (N1 or N2), but it has not spread to lymph nodes farther away from the esophagus or to distant sites (M0). It can be any grade (G). Alternatively, T4b, any N, M0, any G: The cancer cannot be removed with surgery because it has grown into the trachea (windpipe), the aorta (the large blood vessel coming from the heart), the spine, or other crucial structures (T4b). It may or may not have spread to nearby lymph nodes (any N), but it has not spread to lymph nodes farther away from the esophagus or to distant sites (M0). It can be any grade (G). Alternatively, Any T, N3, M0, any G: The cancer has spread to 7 or more nearby lymph nodes (N3), but it has not spread to lymph nodes farther away from the esophagus or to distant sites (M0). It can be any grade (G).

Stage IV: Any T, any N, M1, any G: The cancer has spread to distant lymph nodes or other sites (M1). It can be any grade (G).

The AJCC staging system provides a detailed summary of how far the cancer has spread. But for treatment purposes, doctors are often more concerned about whether the cancer can be removed completely with surgery (resected). If, based on where the cancer is and how far it has spread, it could be removed completely by surgery, it is considered potentially resectable. If the cancer has spread too far to be removed completely, it is considered unresectable. Generally, all stage 0, I, and II esophageal cancers are potentially resectable. Most stage III cancers are potentially resectable as well, even when they have spread to nearby lymph nodes, as long as the cancer has not grown into the trachea (windpipe), the aorta (the large blood vessel coming from the heart), the spine, or other nearby crucial structures. Unfortunately, many people whose cancer is potentially resectable may not be able to have surgery to remove their cancers because they aren't healthy enough.

Cancers that have grown into these structures or that have spread to distant lymph nodes or to other organs are considered unresectable, so treatments other than surgery are usually the best option.

In certain embodiments, the cancer is a gastric cancer or gastric pre-cancerous lesion (metaplasia). Gastric cancer is the result of uncontrolled epithelial cell growth in the stomach. About 90-95% of gastric cancers are adenocarcinomas that arise from mucosal cells forming the innermost lining of the stomach. Less common forms of gastric cancer include carcinoid tumors, squamous cell carcinoma, small cell carcinoma, and leiomyosarcoma, of the stomach. In one embodiment, the gastric cancer is a gastric adenocarcinoma.

Staging of gastric cancer is typically performed based upon whether surgery is performed or not performed. The clinical stage of the cancer is the doctor's best estimate of the extent of the cancer, based on the results of physical exams, endoscopy, biopsies, and any imaging tests (such as CT scans) that have been done. If surgery is performed, then the pathologic stage can be determined using the same test results used for the clinical stage, plus what is found from tissues removed during surgery. The clinical stage is used to help plan treatment. Sometimes, though, the cancer has spread further than the clinical stage estimates. Because the pathologic stage is based on what was found at surgery, it can more accurately predict the patient's outlook. Pathologic staging is typically performed using the American Joint Commission on Cancer (AJCC) TNM system available from the American Cancer Society on the World Wide Web at cancer.org. The TNM system for staging contains 3 key pieces of information: "T" describes the extent of the primary tumor (how far it has grown into the wall of the stomach and into nearby organs); "N" describes the spread to nearby (regional) lymph nodes; and "M" indicates whether the cancer has metastasized (spread) to distant parts of the body. The most common sites of distant spread of stomach cancer are the liver, the peritoneum (the lining of the space around the digestive organs), and distant lymph nodes. Less common sites of spread include the lungs and brain.

Numbers or letters appear after T, N, and M to provide more details about each of these factors: The numbers 0 through 4 indicate increasing severity; the letter X means "cannot be assessed" because the information is not available; and the letters "is" refer to carcinoma in situ, which means the tumor is only in the top layer of mucosa cells and has not yet invaded deeper layers of tissue. This system is for staging all stomach cancers except those starting in either the gastroesophageal junction (where the stomach and the esophagus meet) or in the cardia (the first part of the stomach) and growing into the gastroesophageal junction. Those cancers are staged (and often treated) like cancers of the esophagus.

Nearly all stomach cancers start in the innermost layer of the stomach wall (the mucosa). The T category describes how far through the stomach's 5 layers the cancer has invaded. The innermost layer is the mucosa. The mucosa has 3 parts: epithelial cells, which lie on top of a layer of connective tissue (the lamina propria), which is on top of a thin layer of muscle (the muscularis mucosa). Under the mucosa is a supporting layer called the submucosa. Below this is the muscularis propria, a thick layer of muscle that moves and mixes the stomach contents. The next 2 layers, the subserosa and the outermost serosa, act as wrapping layers for the stomach. The T stages include: TX: The main (primary) tumor cannot be assessed; T0: No signs of a main tumor can be found; Tis: Cancer cells are only in the top layer of cells of the mucosa (innermost layer of the stomach) and have not grown into deeper layers of tissue such as the lamina propria or muscularis mucosa. This stage is also known as carcinoma in situ; T1: The tumor has grown from the top layer of cells of the mucosa into the next layers below such as the lamina propria, the muscularis mucosa, or submucosa; T1a: The tumor is growing into the lamina propria or muscularis mucosa; T1b: The tumor has grown through the lamina propria and muscularis mucosa and into the submucosa; T2: The tumor is growing into the muscularis propria layer; T3: The tumor is growing into the subserosa layer; T4: The tumor has grown into the serosa and may be growing into a nearby organ (spleen, intestines, pancreas, kidney, etc.) or other structures such as major blood vessels; T4a: The tumor has grown through the stomach wall into the serosa, but the cancer hasn't grown into any of the nearby organs or structures; and T4b: The tumor has grown through the stomach wall and into nearby organs or structures.

The N categories of gastric cancer include: NX: Nearby (regional) lymph nodes cannot be assessed; N0: No spread to nearby lymph nodes; N1: The cancer has spread to 1 to 2 nearby lymph nodes; N2: The cancer has spread to 3 to 6 nearby lymph nodes; N3: The cancer has spread 7 or more nearby lymph nodes; N3a: The cancer has spread to 7 to 15 nearby lymph nodes; and N3b: The cancer has spread to 16 or more nearby lymph nodes.

The M categories of gastric cancer include: M0: No distant metastasis (the cancer has not spread to distant organs or sites, such as the liver, lungs, or brain); and M1: Distant metastasis (the cancer has spread to organs or lymph nodes far away from the stomach).

Once the T, N, and M categories have been determined, this information is combined and expressed as a stage, using the number 0 (zero) and the Roman numerals I through IV. This is known as stage grouping. Some stages are split into substages, indicated by letters, including the following:

Stage 0: Tis, N0, M0: This is stomach cancer in its earliest stage. It has not grown beyond the inner layer of cells that line the stomach (Tis). The cancer has not spread to any lymph nodes (N0) or anywhere else (M0). This stage is also known as carcinoma in situ.

Stage IA: T1, N0, M0: The cancer has grown beneath the top layer of cells in the mucosa into tissue below, such as the connective tissue (lamina propria), the thin muscle layer (muscularis mucosa), or the submucosa (T1). The cancer has not spread to any lymph nodes (N0) or anywhere else (M0).

Stage IB: Any of the following: T1, N1, M0: The cancer has grown into the layer of connective tissue (lamina propria), and may have grown into the thin layer of muscle beneath it (muscularis mucosa) or deeper into the submucosa (T1). Cancer has also spread to 1 or 2 lymph nodes near the stomach (N1), but not to any distant tissues or organs (M0). Alternatively, T2, N0, M0: The cancer has grown into the main muscle layer of the stomach wall, called the muscularis propria (T2). It has not spread to nearby lymph nodes (N0) or to any distant tissues or organs (M0).

Stage IIA: Any of the following: T1, N2, M0: The cancer has grown beneath the top layer of cells of the mucosa into the layer of connective tissue (lamina propria), thin muscle layer (muscularis mucosa), or the submucosa (T1). It has spread to 3 to 6 nearby lymph nodes (N2). It has not spread to distant sites (M0); Alternatively, T2, N1, M0: The cancer has grown into the main muscle layer of the stomach called the muscularis propria (T2). It has spread to 1 or 2 nearby lymph nodes (N1), but has not spread to distant sites (M0). Alternatively, T3, N0, M0: The cancer has grown through the main muscle layer into the subserosa, but has not grown through all the layers to the outside the stomach (T3). It has not spread to any nearby lymph nodes (N0) or to distant tissues or organs (M0).

Stage IIB: Any of the following: T1, N3, M0: The cancer has grown beneath the top layer of cells of the mucosa into the layer of connective tissue (lamina propria), the thin muscle layer, or the submucosa (T1). It has spread to 7 or more nearby lymph nodes (N3). It has not spread to distant tissues or organs (M0). Alternatively, T2, N2, M0: The cancer has grown into the main muscle layer, called the muscularis propria (T2). It has spread to 3 to 6 nearby lymph nodes (N2), but it has not spread to distant tissues or organs (M0). Alternatively, T3, N1, M0: The cancer has grown into the subserosa layer, but not through all the layers to the outside of the stomach (T3). It has spread to 1 or 2 nearby lymph nodes (N1), but has not spread to distant tissues or organs (M0). Alternatively, T4a, N0, M0: The cancer has grown completely through all the layers of stomach wall into the outer covering of the stomach (the serosa), but it has not grown into nearby organs or tissues, such as the spleen, intestines, kidneys, or pancreas (T4a). It has not spread to any nearby lymph nodes (N0) or distant sites (M0).

Stage IIIA: Any of the following: T2, N3, M0: The cancer has grown into the main muscle layer, called the muscularis propria (T2). It has spread to 7 or more nearby lymph nodes (N3), but has not spread to distant tissues or organs (M0). Alternatively, T3, N2, M0: The cancer has grown into the subserosa layer, but not through all the layers to the outside of the stomach (T3). It has spread to 3 to 6 nearby lymph nodes (N2), but it has not spread to distant tissues or organs (M0). Alternatively, T4a, N1, M0: The cancer has grown completely through all the layers of the stomach wall into the outer covering of the stomach (the serosa), but it has not grown into nearby organs or tissues (T4a). It has spread to 1 or 2 nearby lymph nodes (N1), but it has not spread to distant sites (M0).

Stage IIIB: Any of the following: T3, N3, M0: The cancer has grown into the sub serosa layer, but not through all the layers to the outside of the stomach (T3). It has spread to 7 or more nearby lymph nodes (N2), but it has not spread to distant sites (M0). Alternatively, T4a, N2, M0: The cancer has grown completely through all the layers of the stomach wall into the serosa (the outer covering of the stomach), but it has not grown into nearby organs or tissues (T4a). It has spread to 3 to 6 nearby lymph nodes (N2), but it has not spread to distant sites (M0). Alternatively, T4b, N0 or N1, M0: The cancer has grown through the stomach wall and into nearby organs or structures, such as the spleen, intestines, liver, pancreas, or major blood vessels (T4b). It may also have spread to up to 2 nearby lymph nodes (N0 or N1). It has not spread to distant sites (M0).

Stage IIIC: Any of the following: T4a, N3, M0: The cancer has grown completely through all the layers of the stomach wall into the serosa, but it has not grown into nearby organs or tissues (T4a). It has spread to 7 or more nearby lymph nodes (N3), but it has not spread to distant sites (M0). Alternatively, T4b, N2 or N3, M0: The cancer has grown through the stomach wall and into nearby organs or structures such as the spleen, intestines, liver, pancreas, or major blood vessels (T4b). It has spread to 3 or more nearby lymph nodes (N2 or N3). It has not spread to distant sites (M0).

Stage IV: Any T, any N, M1: The cancer has spread to distant organs such as the liver, lungs, brain, or bones (M1).

The AJCC staging system provides a detailed summary of how far a stomach cancer has spread. But for treatment purposes, doctors are often more concerned about whether the tumor can be removed (resected) with surgery. Resectable cancers are those the doctor believes can be completely removed during surgery. Unresectable cancers can't be removed completely. This might be because the tumor has grown too far into nearby organs or lymph nodes, it has grown too close to major blood vessels, it has spread to distant parts of the body, or the person is not healthy enough for surgery. There is no distinct dividing line between resectable and unresectable in terms of the TNM stage of the cancer, but earlier stage cancers are more likely to be resectable.

The term "coding region" refers to regions of a nucleotide sequence comprising codons which are translated into amino acid residues, whereas the term "noncoding region" refers to regions of a nucleotide sequence that are not translated into amino acids (e.g., 5' and 3' untranslated regions).

The term "complementary" refers to the broad concept of sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. Preferably, the first region comprises a first portion and the second region comprises a second portion, whereby, when the first and second portions are arranged in an antiparallel fashion, at least about 50%, and preferably at least about 75%, at least about 90%, or at least about 95% of the nucleotide residues of the first portion are capable of base pairing with nucleotide residues in the second portion. More preferably, all nucleotide residues of the first portion are capable of base pairing with nucleotide residues in the second portion.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the present invention are not limited to use of a specific cut-point in comparing the level of expression product in the test sample to the control.

The "copy number" of a biomarker nucleic acid refers to the number of DNA sequences in a cell (e.g., germline and/or somatic) encoding a particular gene product. Generally, for a given gene, a mammal has two copies of each gene. The copy number can be increased, however, by gene amplification or duplication, or reduced by deletion. For example, germline copy number changes include changes at one or more genomic loci, wherein said one or more genomic loci are not accounted for by the number of copies in the normal complement of germline copies in a control (e.g., the normal copy number in germline DNA for the same species as that from which the specific germline DNA and corresponding copy number were determined). Somatic copy number changes include changes at one or more genomic loci, wherein said one or more genomic loci are not accounted for by the number of copies in germline DNA of a control (e.g., copy number in germline DNA for the same subject as that from which the somatic DNA and corresponding copy number were determined).

The "normal" copy number (e.g., germline and/or somatic) of a biomarker nucleic acid or "normal" level of expression of a biomarker nucleic acid or protein is the activity/level of expression or copy number in a biological sample, e.g., a sample containing tissue, whole blood, serum, plasma, buccal scrape, saliva, cerebrospinal fluid, urine, stool, and bone marrow, from a subject, e.g., a human, not afflicted with cancer, or from a corresponding non-cancerous tissue in the same subject who has cancer.

As used herein, the term "costimulate" with reference to activated immune cells includes the ability of a costimulatory molecule to provide a second, non-activating receptor mediated signal (a "costimulatory signal") that induces proliferation or effector function. For example, a costimulatory signal can result in cytokine secretion, e.g., in a T cell that has received a T cell-receptor-mediated signal. Immune cells that have received a cell-receptor mediated signal, e.g., via an activating receptor are referred to herein as "activated immune cells."

The term "determining a suitable treatment regimen for the subject" is taken to mean the determination of a treatment regimen (i.e., a single therapy or a combination of different therapies that are used for the prevention and/or treatment of the cancer in the subject) for a subject that is started, modified and/or ended based or essentially based or at least partially based on the results of the analysis according to the present invention. One example is determining whether to provide targeted therapy against a cancer to provide immunotherapy that generally increases immune responses against the cancer (e.g., anti-immune checkpoint therapy). Another example is starting an adjuvant therapy after surgery whose purpose is to decrease the risk of recurrence, another would be to modify the dosage of a particular chemotherapy. The determination can, in addition to the results of the analysis according to the present invention, be based on personal characteristics of the subject to be treated. In most cases, the actual determination of the suitable treatment regimen for the subject will be performed by the attending physician or doctor.

The term "diagnosing cancer" includes the use of the methods, systems, and code of the present invention to determine the presence or absence of a cancer or subtype thereof in an individual. The term also includes methods, systems, and code for assessing the level of disease activity in an individual.

A molecule is "fixed" or "affixed" to a substrate if it is covalently or non-covalently associated with the substrate such that the substrate can be rinsed with a fluid (e.g. standard saline citrate, pH 7.4) without a substantial fraction of the molecule dissociating from the substrate.

The term "expression signature" or "signature" refers to a group of two or more coordinately expressed biomarkers. For example, the genes, proteins, metabolites, and the like making up this signature may be expressed in a specific cell lineage, stage of differentiation, or during a particular biological response. The biomarkers can reflect biological aspects of the tumors in which they are expressed, such as the cell of origin of the cancer, the nature of the non-malignant cells in the biopsy, and the oncogenic mechanisms responsible for the cancer. Expression data and gene expression levels can be stored on computer readable media, e.g., the computer readable medium used in conjunction with a microarray or chip reading device. Such expression data can be manipulated to generate expression signatures.

"Homologous" as used herein, refers to nucleotide sequence similarity between two regions of the same nucleic acid strand or between regions of two different nucleic acid strands. When a nucleotide residue position in both regions is occupied by the same nucleotide residue, then the regions are homologous at that position. A first region is homologous to a second region if at least one nucleotide residue position of each region is occupied by the same residue. Homology between two regions is expressed in terms of the proportion of nucleotide residue positions of the two regions that are occupied by the same nucleotide residue. By way of example, a region having the nucleotide sequence 5'-ATTGCC-3' and a region having the nucleotide sequence 5'-TATGGC-3' share 50% homology. Preferably, the first region comprises a first portion and the second region comprises a second portion, whereby, at least about 50%, and preferably at least about 75%, at least about 90%, or at least about 95% of the nucleotide residue positions of each of the portions are occupied by the same nucleotide residue. More preferably, all nucleotide residue positions of each of the portions are occupied by the same nucleotide residue.

The term "immune cell" refers to cells that play a role in the immune response. Immune cells are of hematopoietic origin, and include lymphocytes, such as B cells and T cells; natural killer cells; myeloid cells, such as monocytes, macrophages, eosinophils, mast cells, basophils, and granulocytes.

The term "immune checkpoint" refers to a group of molecules on the cell surface of CD4+ and/or CD8+ T cells that fine-tune immune responses by down-modulating or inhibiting an anti-tumor immune response. Immune checkpoint proteins are well known in the art and include, without limitation, CTLA-4, PD-1, VISTA, B7-H2, B7-H3, PD-L1, B7-H4, B7-H6, 2B4, ICOS, HVEM, PD-L2, CD160, gp49B, PIR-B, KIR family receptors, TIM-1, TIM-3, TIM-4, LAG-3, BTLA, SIRPalpha (CD47), CD48, 2B4 (CD244), B7.1, B7.2, ILT-2, ILT-4, TIGIT, and A2aR (see, for example, WO 2012/177624). The term further encompasses biologically active protein fragment, as well as nucleic acids encoding full-length immune checkpoint proteins and biologically active protein fragments thereof. In some embodiment, the term further encompasses any fragment according to homology descriptions provided herein.

"Anti-immune checkpoint therapy" refers to the use of agents that inhibit immune checkpoint nucleic acids and/or proteins. Inhibition of one or more immune checkpoints can block or otherwise neutralize inhibitory signaling to thereby upregulate an immune response in order to more efficaciously treat cancer. Exemplary agents useful for inhibiting immune checkpoints include antibodies, small molecules, peptides, peptidomimetics, natural ligands, and derivatives of natural ligands, that can either bind and/or inactivate or inhibit immune checkpoint proteins, or fragments thereof; as well as RNA interference, antisense, nucleic acid aptamers, etc. that can downregulate the expression and/or activity of immune checkpoint nucleic acids, or fragments thereof. Exemplary agents for upregulating an immune response include antibodies against one or more immune checkpoint proteins block the interaction between the proteins and its natural receptor(s); a non-activating form of one or more immune checkpoint proteins (e.g., a dominant negative polypeptide); small molecules or peptides that block the interaction between one or more immune checkpoint proteins and its natural receptor(s); fusion proteins (e.g. the extracellular portion of an immune checkpoint inhibition protein fused to the Fc portion of an antibody or immunoglobulin) that bind to its natural receptor(s); nucleic acid molecules that block immune checkpoint nucleic acid transcription or translation; and the like. Such agents can directly block the interaction between the one or more immune checkpoints and its natural receptor(s) (e.g., antibodies) to prevent inhibitory signaling and upregulate an immune response. Alternatively, agents can indirectly block the interaction between one or more immune checkpoint proteins and its natural receptor(s) to prevent inhibitory signaling and upregulate an immune response. For example, a soluble version of an immune checkpoint protein ligand such as a stabilized extracellular domain can binding to its receptor to indirectly reduce the effective concentration of the receptor to bind to an appropriate ligand. In one embodiment, anti-PD-1 antibodies, anti-PD-L1 antibodies, and/or anti-PD-L2 antibodies, either alone or in combination, are used to inhibit immune checkpoints. These embodiments are also applicable to specific therapy against particular immune checkpoints, such as the PD-1 pathway (e.g., anti-PD-1 pathway therapy, otherwise known as PD-1 pathway inhibitor therapy).

The term "immune response" includes T cell mediated and/or B cell mediated immune responses. Exemplary immune responses include T cell responses, e.g., cytokine production and cellular cytotoxicity. In addition, the term immune response includes immune responses that are indirectly effected by T cell activation, e.g., antibody production (humoral responses) and activation of cytokine responsive cells, e.g., macrophages.

The term "immunotherapeutic agent" can include any molecule, peptide, antibody or other agent which can stimulate a host immune system to generate an immune response to a tumor or cancer in the subject. Various immunotherapeutic agents are useful in the compositions and methods described herein.

The term "inhibit" includes the decrease, limitation, or blockage, of, for example a particular action, function, or interaction. In some embodiments, cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

The term "interaction", when referring to an interaction between two molecules, refers to the physical contact (e.g., binding) of the molecules with one another. Generally, such an interaction results in an activity (which produces a biological effect) of one or both of said molecules.

An "isolated protein" refers to a protein that is substantially free of other proteins, cellular material, separation medium, and culture medium when isolated from cells or produced by recombinant DNA techniques, or chemical precursors or other chemicals when chemically synthesized. An "isolated" or "purified" protein or biologically active portion thereof is substantially free of cellular material or other contaminating proteins from the cell or tissue source from which the antibody, polypeptide, peptide or fusion protein is derived, or substantially free from chemical precursors or other chemicals when chemically synthesized. The language "substantially free of cellular material" includes preparations of a biomarker polypeptide or fragment thereof, in which the protein is separated from cellular components of the cells from which it is isolated or recombinantly produced. In one embodiment, the language "substantially free of cellular material" includes preparations of a biomarker protein or fragment thereof, having less than about 30% (by dry weight) of non-biomarker protein (also referred to herein as a "contaminating protein"), more preferably less than about 20% of non-biomarker protein, still more preferably less than about 10% of non-biomarker protein, and most preferably less than about 5% non-biomarker protein. When antibody, polypeptide, peptide or fusion protein or fragment thereof, e.g., a biologically active fragment thereof, is recombinantly produced, it is also preferably substantially free of culture medium, i.e., culture medium represents less than about 20%, more preferably less than about 10%, and most preferably less than about 5% of the volume of the protein preparation.

A "kit" is any manufacture (e.g. a package or container) comprising at least one reagent, e.g. a probe or small molecule, for specifically detecting and/or affecting the expression of a marker of the present invention. The kit may be promoted, distributed, or sold as a unit for performing the methods of the present invention. The kit may comprise one or more reagents necessary to express a composition useful in the methods of the present invention. In certain embodiments, the kit may further comprise a reference standard, e.g., a nucleic acid encoding a protein that does not affect or regulate signaling pathways controlling cell growth, division, migration, survival or apoptosis. One skilled in the art can envision many such control proteins, including, but not limited to, common molecular tags (e.g., green fluorescent protein and beta-galactosidase), proteins not classified in any of pathway encompassing cell growth, division, migration, survival or apoptosis by GeneOntology reference, or ubiquitous housekeeping proteins. Reagents in the kit may be provided in individual containers or as mixtures of two or more reagents in a single container. In addition, instructional materials which describe the use of the compositions within the kit can be included.

The term "neoadjuvant therapy" refers to a treatment given before the primary treatment. Examples of neoadjuvant therapy can include chemotherapy, radiation therapy, and hormone therapy. For example, in treating breast cancer, neoadjuvant therapy can allows patients with large breast cancer to undergo breast-conserving surgery.

The "normal" level of expression of a biomarker is the level of expression of the biomarker in cells of a subject, e.g., a human patient, not afflicted with a cancer. An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

An "over-expression" or "significantly higher level of expression" of a biomarker refers to an expression level in a test sample that is greater than the standard error of the assay employed to assess expression, and is preferably at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the biomarker in a control sample (e.g., sample from a healthy subject not having the biomarker associated disease) and preferably, the average expression level of the biomarker in several control samples. A "significantly lower level of expression" of a biomarker refers to an expression level in a test sample that is at least 10%, and more preferably 1.2, 1.3, 1.4, 1.5, 1.6, 1.7, 1.8, 1.9, 2.0, 2.1, 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the biomarker in a control sample (e.g., sample from a healthy subject not having the biomarker associated disease) and preferably, the average expression level of the biomarker in several control samples.

The term "pre-determined" biomarker amount and/or activity measurement(s) may be a biomarker amount and/or activity measurement(s) used to, by way of example only, evaluate a subject that may be selected for a particular treatment, evaluate a response to a treatment such as a PD-1 pathway inhibitor therapy, and/or evaluate the disease state. A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements. In another embodiment, the amounts determined and/or compared in a method described herein are based on relative measurements, such as ratios (e.g., serum biomarker normalized to the expression of a housekeeping or otherwise generally constant biomarker). The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to PD-1 pathway inhibitor treatment (e.g., therapeutic antibodies against PD-1, PD-L1, PD-L2, and the like). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC), or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular PD-1 pathway inhibitor therapy or those developing resistance thereto).

The term "pre-malignant lesions" as described herein refers to a lesion that, while not cancerous, has potential for becoming cancerous. It also includes the term "pre-malignant disorders" or "potentially malignant disorders." In particular this refers to a benign, morphologically and/or histologically altered tissue that has a greater than normal risk of malignant transformation, and a disease or a patient's habit that does not necessarily alter the clinical appearance of local tissue but is associated with a greater than normal risk of precancerous lesion or cancer development in that tissue (leukoplakia, erythroplakia, erythroleukoplakia lichen planus (lichenoid reaction) and any lesion or an area which histological examination showed atypia of cells or dysplasia. In one embodiment, a metaplasia is a pre-malignant lesion.

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "probe" refers to any molecule which is capable of selectively binding to a specifically intended target molecule, for example, a nucleotide transcript or protein encoded by or corresponding to a biomarker nucleic acid. Probes can be either synthesized by one skilled in the art, or derived from appropriate biological preparations. For purposes of detection of the target molecule, probes may be specifically designed to be labeled, as described herein. Examples of molecules that can be utilized as probes include, but are not limited to, RNA, DNA, proteins, antibodies, and organic molecules.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as esophageal cancer and gastric cancer), development of one or more clinical factors, or recovery from the disease.

The term "response to anti-cancer therapy" or "response to anti-PD-1 pathway therapy" relates to any response of the hyperproliferative disorder (e.g., cancer) to an anti-cancer agent such as an anti-PD-1 pathway agent, preferably to a change in tumor mass and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any cancer therapy. The outcome measurement may be pathologic response to therapy given in the neoadjuvant setting. Alternatively, outcome measures, such as overall survival and disease-free survival can be monitored over a period of time for subjects following cancer therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of a cancer therapy can be determined using well-known methods in the art, such as those described in the Examples section.

The term "resistance" refers to an acquired or natural resistance of a cancer sample or a mammal to a cancer therapy (i.e., being nonresponsive to or having reduced or limited response to the therapeutic treatment), such as having a reduced response to a therapeutic treatment by 25% or more, for example, 30%, 40%, 50%, 60%, 70%, 80%, or more, to 2-fold, 3-fold, 4-fold, 5-fold, 10-fold, 15-fold, 20-fold or more. The reduction in response can be measured by comparing with the same cancer sample or mammal before the resistance is acquired, or by comparing with a different cancer sample or a mammal who is known to have no resistance to the therapeutic treatment. A typical acquired resistance to chemotherapy is called "multidrug resistance." The multidrug resistance can be mediated by P-glycoprotein or can be mediated by other mechanisms, or it can occur when a mammal is infected with a multi-drug-resistant microorganism or a combination of microorganisms. The determination of resistance to a therapeutic treatment is routine in the art and within the skill of an ordinarily skilled clinician, for example, can be measured by cell proliferative assays and cell death assays as described herein as "sensitizing." In some embodiments, the term "reverses resistance" means that the use of a second agent in combination with a primary cancer therapy (e.g., chemotherapeutic or radiation therapy) is able to produce a significant decrease in tumor volume at a level of statistical significance (e.g., $p<0.05$) when compared to tumor volume of untreated tumor in the circumstance where the primary cancer therapy (e.g., chemotherapeutic or radiation therapy) alone is unable to produce a statistically significant decrease in tumor volume compared to tumor volume of untreated tumor. This generally applies to tumor volume measurements made at a time when the untreated tumor is growing log rhythmically.

The terms "response" or "responsiveness" refers to an anti-cancer response, e.g. in the sense of reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

An "RNA interfering agent" as used herein, is defined as any agent which interferes with or inhibits expression of a target biomarker gene by RNA interference (RNAi). Such RNA interfering agents include, but are not limited to, nucleic acid molecules including RNA molecules which are homologous to the target biomarker gene of the present invention, or a fragment thereof, short interfering RNA (siRNA), and small molecules which interfere with or inhibit expression of a target biomarker nucleic acid by RNA interference (RNAi).

"RNA interference (RNAi)" is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see Coburn, G. and Cullen, B. (2002) *J. of Virology* 76(18):9225), thereby inhibiting expression of the target biomarker nucleic acid. In one embodiment, the RNA is double stranded RNA (dsRNA). This process has been described in plants, invertebrates, and mammalian cells. In nature, RNAi is initiated by the dsRNA-specific endonuclease Dicer, which promotes processive cleavage of long dsRNA into double-stranded fragments termed siRNAs. siRNAs are incorporated into a protein complex that recognizes and cleaves target mRNAs. RNAi can also be initiated by introducing nucleic acid molecules, e.g., synthetic siRNAs or RNA interfering agents, to inhibit or silence the expression of target biomarker nucleic acids. As used herein, "inhibition of target biomarker nucleic acid expression" or "inhibition of marker gene expression" includes any decrease in expression or protein activity or level of the target biomarker nucleic acid or protein encoded by the target biomarker nucleic acid. The decrease may be of at least 30%, 40%, 50%, 60%, 70%, 80%, 90%, 95% or 99% or more as compared to the expression of a target biomarker nucleic acid or the activity or level of the protein encoded by a target biomarker nucleic acid which has not been targeted by an RNA interfering agent.

The term "sample" used for detecting or determining the presence or level of at least one biomarker is typically whole blood, plasma, serum, saliva, urine, stool (e.g., feces), tears, and any other bodily fluid (e.g., as described above under the definition of "body fluids"), or a tissue sample (e.g., biopsy) such as a small intestine, colon sample, or surgical resection tissue. In certain instances, the method of the present invention further comprises obtaining the sample from the individual prior to detecting or determining the presence or level of at least one marker in the sample.

The term "sensitize" means to alter cancer cells or tumor cells in a way that allows for more effective treatment of the associated cancer with a cancer therapy (e.g., anti-immune checkpoint, chemotherapeutic, and/or radiation therapy). In some embodiments, normal cells are not affected to an extent that causes the normal cells to be unduly injured by the anti-immune checkpoint therapy. An increased sensitivity or a reduced sensitivity to a therapeutic treatment is measured according to a known method in the art for the particular treatment and methods described herein below, including, but not limited to, cell proliferative assays (Tanigawa N, Kern D H, Kikasa Y, Morton D L, Cancer Res 1982; 42: 2159-2164), cell death assays (Weisenthal L M, Shoemaker R H, Marsden J A, Dill P L, Baker J A, Moran E M, Cancer Res 1984; 94: 161-173; Weisenthal L M, Lippman M E, Cancer Treat Rep 1985; 69: 615-632; Weisenthal L M, In: Kaspers G J L, Pieters R, Twentyman P R, Weisenthal L M, Veerman A J P, eds. Drug Resistance in Leukemia and Lymphoma. Langhorne, P A: Harwood Academic Publishers, 1993: 415-432; Weisenthal L M, Contrib Gynecol Obstet 1994; 19: 82-90). The sensitivity or resistance may also be measured in animal by measuring the tumor size reduction over a period of time, for example, 6 month for human and 4-6 weeks for mouse. A composition or a method sensitizes response to a therapeutic treatment if the increase in treatment sensitivity or the reduction in resistance is 25% or more, for example, 30%, 40%, 50%, 60%, 70%, 80%, or more, to 2-fold, 3-fold, 4-fold, 5-fold, 10-fold, 15-fold, 20-fold or more, compared to treatment sensitivity or resistance in the absence of such composition or method. The determination of sensitivity or resistance to a therapeutic treatment is routine in the art and within the skill of an ordinarily skilled clinician. It is to be understood that any method described herein for enhancing the efficacy of a cancer therapy can be equally applied to methods for sensitizing hyperproliferative or otherwise cancerous cells (e.g., resistant cells) to the cancer therapy.

The term "synergistic effect" refers to the combined effect of two or more anti-cancer agents (e.g., two or more PD-1 pathway inhibitors) can be greater than the sum of the separate effects of the anticancer agents alone.

"Short interfering RNA" (siRNA), also referred to herein as "small interfering RNA" is defined as an agent which functions to inhibit expression of a target biomarker nucleic acid, e.g., by RNAi. An siRNA may be chemically synthesized, may be produced by in vitro transcription, or may be produced within a host cell. In one embodiment, siRNA is a double stranded RNA (dsRNA) molecule of about 15 to about 40 nucleotides in length, preferably about 15 to about 28 nucleotides, more preferably about 19 to about 25 nucleotides in length, and more preferably about 19, 20, 21, or 22 nucleotides in length, and may contain a 3' and/or 5' overhang on each strand having a length of about 0, 1, 2, 3, 4, or 5 nucleotides. The length of the overhang is independent between the two strands, i.e., the length of the overhang on one strand is not dependent on the length of the overhang on the second strand. Preferably the siRNA is capable of promoting RNA interference through degradation or specific post-transcriptional gene silencing (PTGS) of the target messenger RNA (mRNA).

In another embodiment, an siRNA is a small hairpin (also called stem loop) RNA (shRNA). In one embodiment, these shRNAs are composed of a short (e.g., 19-25 nucleotide) antisense strand, followed by a 5-9 nucleotide loop, and the analogous sense strand. Alternatively, the sense strand may precede the nucleotide loop structure and the antisense strand may follow. These shRNAs may be contained in plasmids, retroviruses, and lentiviruses and expressed from, for example, the pol III U6 promoter, or another promoter (see, e.g., Stewart, et al. (2003) *RNA* April; 9(4):493-501 incorporated by reference herein).

RNA interfering agents, e.g., siRNA molecules, may be administered to a patient having or at risk for having cancer, to inhibit expression of a biomarker gene which is overexpressed in cancer and thereby treat, prevent, or inhibit cancer in the subject.

The term "subject" refers to any healthy animal, mammal or human, or any animal, mammal or human afflicted with a cancer, e.g., lung, ovarian, pancreatic, liver, breast, prostate, and colon carcinomas, as well as melanoma and multiple myeloma. The term "subject" is interchangeable with "patient."

The term "survival" includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g. time of diagnosis or start of treatment) and end point (e.g. death, recurrence or metastasis). In addition, criteria for efficacy of treatment can be expanded to include response to chemotherapy, probability of survival, probability of metastasis within a given time period, and probability of tumor recurrence.

The term "therapeutic effect" refers to a local or systemic effect in animals, particularly mammals, and more particularly humans, caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically effective amount of a compound will depend on its therapeutic index, solubility, and the like. For example, certain compounds discovered by the methods of the present invention may be administered in a sufficient amount to produce a reasonable benefit/risk ratio applicable to such treatment.

The terms "therapeutically-effective amount" and "effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment. Toxicity and therapeutic efficacy of subject compounds may be determined by standard pharmaceutical procedures in cell cultures or experimental animals, e.g., for determining the $LD_{50}$ and the $ED_{50}$. Compositions that exhibit large therapeutic indices are preferred. In some embodiments, the $LD_{50}$ (lethal dosage) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more reduced for the agent relative to no administration of the agent. Similarly, the $ED_{50}$ (i.e., the concentration which achieves a half-maximal inhibition of symptoms) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. Also, Similarly, the $IC_{50}$ (i.e., the concentration which achieves half-maximal cytotoxic or cytostatic effect on cancer cells) can be measured and can be, for example, at least 10%, 20%, 30%, 40%, 50%, 60%, 70%, 80%, 90%, 100%, 200%, 300%, 400%, 500%, 600%, 700%, 800%, 900%, 1000% or more increased for the agent relative to no administration of the agent. In some embodiments, cancer cell growth in an assay can be inhibited by at least about 10%, 15%, 20%, 25%, 30%, 35%, 40%, 45%, 50%, 55%, 60%, 65%, 70%, 75%, 80%, 85%, 90%, 95%, or even 100%. In another embodiment, at least about a 10%, 15%, 20%, 25%, 30%, 35%, 40%, 45%, 50%, 55%, 60%, 65%, 70%, 75%, 80%, 85%, 90%, 95%, or even 100% decrease in a solid malignancy can be achieved.

A "transcribed polynucleotide" or "nucleotide transcript" is a polynucleotide (e.g. an mRNA, hnRNA, a cDNA, or an analog of such RNA or cDNA) which is complementary to or homologous with all or a portion of a mature mRNA made by transcription of a biomarker nucleic acid and normal post-transcriptional processing (e.g. splicing), if any, of the RNA transcript, and reverse transcription of the RNA transcript.

As used herein, the term "unresponsiveness" includes refractivity of immune cells to stimulation, e.g., stimulation via an activating receptor or a cytokine. Unresponsiveness can occur, e.g., because of exposure to immunosuppressants or exposure to high doses of antigen. As used herein, the term "anergy" or "tolerance" includes refractivity to activating receptor-mediated stimulation. Such refractivity is generally antigen-specific and persists after exposure to the tolerizing antigen has ceased. For example, anergy in T cells (as opposed to unresponsiveness) is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134).

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid and the amino acid sequence encoded by that nucleic acid, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp, D) | GAC, GAT |
| Cysteine (Cys, C) | TGC, TGT |

| GENETIC CODE | |
|---|---|
| Glutamic acid (Glu, E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe, F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA encoding a biomarker nucleic acid (or any portion thereof) can be used to derive the polypeptide amino acid sequence, using the genetic code to translate the DNA or RNA into an amino acid sequence. Likewise, for polypeptide amino acid sequence, corresponding nucleotide sequences that can encode the polypeptide can be deduced from the genetic code (which, because of its redundancy, will produce multiple nucleic acid sequences for any given amino acid sequence). Thus, description and/or disclosure herein of a nucleotide sequence which encodes a polypeptide should be considered to also include description and/or disclosure of the amino acid sequence encoded by the nucleotide sequence. Similarly, description and/or disclosure of a polypeptide amino acid sequence herein should be considered to also include description and/or disclosure of all possible nucleotide sequences that can encode the amino acid sequence.

Finally, nucleic acid and amino acid sequence information for the loci and biomarkers of the present invention (e.g., biomarkers listed in Tables 1 and 2) are well known in the art and readily available on publicly available databases, such as the National Center for Biotechnology Information (NCBI). For example, exemplary nucleic acid and amino acid sequences derived from publicly available sequence databases are provided below and include, for example, PCT Publ. WO 2014/022759, which is incorporated herein in its entirety by this reference.

For example, the term "PD-1 pathway" refers to the PD-1 receptor and its ligands, PD-L1 and PD-L2. "PD-1 pathway inhibitors" block or otherwise reduce the interaction between PD-1 and one or both of its ligands such that the immunoinhibitory signaling otherwise generated by the interaction is blocked or otherwise reduced. PD-1 pathway inhibitors can be direct or indirect. Direct PD-1 pathway inhibitors block or otherwise reduce the interaction between PD-1 and one or both of its ligands. Direct PD-1 pathway inhibitors are well known in the art, especially since the natural binding partners of PD-1 (e.g., PD-L1 and PD-L2), PD-L1 (e.g., PD-1 and B7-1), and PD-L2 (e.g., PD-1 and RGMb) are known.

For example, agents which directly block the interaction between PD-1 and PD-L1, PD-1 and PD-L2, PD-1 and both PD-L1 and PD-L2 such as a bispecific antibody, can prevent inhibitory signaling and upregulate an immune response (i.e., as a PD-1 pathway inhibitor). Alternatively, agents that indirectly block the interaction between PD-1 and one or both of its ligands can prevent inhibitory signaling and upregulate an immune response. For example, B7-1 or a soluble form thereof, by binding to a PD-L1 polypeptide indirectly reduces the effective concentration of PD-L1 polypeptide available to bind to PD-1. Exemplary agents include monospecific or bispecific blocking antibodies against PD-1, PD-L1, and/or PD-L2 that block the interaction between the receptor and ligand(s); a non-activating form of PD-1, PD-L1, and/or PD-L2 (e.g., a dominant negative or soluble polypeptide), small molecules or peptides that block the interaction between PD-1, PD-L1, and/or PD-L2; fusion proteins (e.g. the extracellular portion of PD-1, PD-L1, and/or PD-L2, fused to the Fc portion of an antibody or immunoglobulin) that bind to PD-1, PD-L1, and/or PD-L2 and inhibit the interaction between the receptor and ligand(s); a non-activating form of a natural PD-1, PD-L2, and/or PD-L2 ligand, and a soluble form of a natural PD-1, PD-L2, and/or PD-L2 ligand.

Indirect PD-1 pathway inhibitors block or otherwise reduce the immunoinhibitory signaling generated by the interaction between PD-1 and one or both of its ligands without necessarily blocking the interaction between PD-1 and one or both of its ligands. For example, indirect PD-1 pathway inhibitors include intrabodies that bind the intracellular portion of PD-1 and/or PD-L1 required to signal to block or otherwise reduce the immunoinhibitory signaling. Similarly, nucleic acids that reduce the expression of PD-1, PD-L1, and/or PD-L2 can indirectly inhibit the interaction between PD-1 and one or both of its ligands by removing the availability of components for interaction. Such nucleic acid molecules can block PD-L1, PD-L2, and/or PD-L2 transcription or translation.

For example, the term "PD-1" refers to a member of the immunoglobulin gene superfamily that functions as a coinhibitory receptor having PD-L1 and PD-L2 as known ligands. PD-1 was previously identified using a subtraction cloning based approach to select for genes upregulated during TCR-induced activated T cell death. PD-1 is a member of the CD28/CTLA-4 family of molecules based on its ability to bind to PD-L1. Like CTLA-4, PD-1 is rapidly induced on the surface of T-cells in response to anti-CD3 (Agata et al. 25 (1996) *Int. Immunol.* 8:765). In contrast to CTLA-4, however, PD-1 is also induced on the surface of B-cells (in response to anti-IgM). PD-1 is also expressed on a subset of thymocytes and myeloid cells (Agata et al. (1996) supra; Nishimura et al. (1996) *Int. Immunol.* 8:773).

The nucleic acid and amino acid sequences of a representative human PD-1 biomarker is available to the public at the GenBank database under NM_005018.2 and NP_005009.2 and is shown in Table 1 (see also Ishida et al. (1992) 20 *EMBO J* 11:3887; Shinohara et al. (1994) Genomics 23:704; U.S. Pat. No. 5,698,520). PD-1 has an extracellular region containing immunoglobulin superfamily domain, a transmembrane domain, and an intracellular region including an immunoreceptor tyrosine-based inhibitory motif (ITIM) (Ishida et al. (1992) *EMBO J.* 11:3887; Shinohara et al. (1994) Genomics 23:704; and U.S. Pat. No. 5,698,520) and an immunoreceptor tyrosine-based switch motif (ITSM). These features also define a larger family of polypeptides, called the immunoinhibitory receptors, which also includes gp49B, PIR-B, and the killer inhibitory receptors (KIRs) (Vivier and Daeron (1997) *Immunol. Today* 18:286). It is often assumed that the tyrosyl phosphorylated ITIM and ITSM motif of these receptors interacts with SH2-domain containing phosphatases, which leads to inhibitory signals. A subset of these immunoinhibitory receptors bind to MHC polypeptides, for example the KIRs, and CTLA4 binds to B7-1 and B7-2. It has been proposed that there is a phylogenetic relationship between the MHC and B7 genes (Henry et al. (1999) *Immunol. Today* 20(6):285-8). Nucleic acid and polypeptide sequences of PD-1 orthologs in organisms other than humans are well known and include, for example, mouse PD-1 (NM_008798.2 and NP_032824.1), rat PD-1 (NM_001106927.1 and NP_001100397.1), dog PD-1 (XM_543338.3 and XP_543338.3), cow PD-1 (NM_001083506.1 and NP_001076975.1), and chicken PD-1 (XM_422723.3 and XP_422723.2).

PD-1 polypeptides are inhibitory receptors capable of transmitting an inhibitory signal to an immune cell to thereby inhibit immune cell effector function, or are capable of promoting costimulation (e.g., by competitive inhibition) of immune cells, e.g., when present in soluble, monomeric form. Preferred PD-1 family members share sequence identity with PD-1 and bind to one or more B7 family members, e.g., B7-1, B7-2, PD-1 ligand, and/or other polypeptides on antigen presenting cells.

The term "PD-1 activity," includes the ability of a PD-1 polypeptide to modulate an inhibitory signal in an activated immune cell, e.g., by engaging a natural PD-1 ligand on an antigen presenting cell. Modulation of an inhibitory signal in an immune cell results in modulation of proliferation of, and/or cytokine secretion by, an immune cell. Thus, the term "PD-1 activity" includes the ability of a PD-1 polypeptide to bind its natural ligand(s), the ability to modulate immune cell costimulatory or inhibitory signals, and the ability to modulate the immune response.

In some embodiments, a condition such as cancer is responsive to PD-1 blockade alone, but is significantly or synergistically more responsive when treated with PD-1 blockade and RGMb blockade in combination. Many conditions responsive to PD-1 blockade alone are known and include, without limitation, melanoma (e.g., advanced or metastatic melanoma), lung cancer (e.g., non small cell lung cancer and small cell lung cancer), breast cancer (e.g., HER-2 negative breast cancer, estrogen-receptor+/HER-2- breast cancer, and triple negative breast cancer), pancreatic cancer (e.g., pancreatic adenocarcinoma), and Hodgkin lymphoma, as well as bladder, gastric, head and neck, renal, prostate, gynecologic, and hematologic cancers.

The term "PD-1 ligand" refers to binding partners of the PD-1 receptor and includes both PD-L1 (Freeman et al. (2000) *J. Exp. Med.* 192:1027) and PD-L2 (Latchman et al. (2001) *Nat. Immunol.* 2:261). At least two types of human PD-1 ligand polypeptides exist. PD-1 ligand proteins comprise a signal sequence, and an IgV domain, an IgC domain, a transmembrane domain, and a short cytoplasmic tail. Both PD-L1 (See Freeman et al. (2000) *J. Exp. Med.* 192:1027 for sequence data) and PD-L2 (See Latchman et al. (2001) *Nat. Immunol.* 2:261 for sequence data) are members of the B7 family of polypeptides. Both PD-L1 and PD-L2 are expressed in placenta, spleen, lymph nodes, thymus, and heart. Only PD-L2 is expressed in pancreas, lung and liver, while only PD-L1 is expressed in fetal liver. Both PD-1 ligands are upregulated on activated monocytes and dendritic cells, although PD-L1 expression is broader. For example, PD-L1 is known to be constitutively expressed and upregulated to higher levels on murine hematopoietic cells (e.g., T cells, B cells, macrophages, dendritic cells (DCs), and bone marrow-derived mast cells) and non-hematopoietic cells (e.g., endothelial, epithelial, and muscle cells), whereas PD-L2 is inducibly expressed on DCs, macrophages, and bone marrow-derived mast cells (see Butte et al. (2007) *Immunity* 27:111).

PD-1 ligands comprise a family of polypeptides having certain conserved structural and functional features. The term "family" when used to refer to proteins or nucleic acid molecules, is intended to mean two or more proteins or nucleic acid molecules having a common structural domain or motif and having sufficient amino acid or nucleotide sequence homology, as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics. PD-1 ligands are members of the B7 family of polypeptides. The term "B7 family" or "B7 polypeptides" as used herein includes costimulatory polypeptides that share sequence homology with B7 polypeptides, e.g., with B7-1, B7-2, B7h (Swallow et al. (1999) *Immunity* 11:423), and/or PD-1 ligands (e.g., PD-L1 or PD-L2). For example, human B7-1 and B7-2 share approximately 26% amino acid sequence identity when compared using the BLAST program at NCBI with the default parameters (Blosum62 matrix with gap penalties set at existence 11 and extension 1 (See the NCBI website). The term B7 family also includes variants of these polypeptides which are capable of modulating immune cell function. The B7 family of molecules share a number of conserved regions, including signal domains, IgV domains and the IgC domains. IgV domains and the IgC domains are art-recognized Ig superfamily member domains. These domains correspond to structural units that have distinct folding patterns called Ig folds. Ig folds are comprised of a sandwich of two β sheets, each consisting of anti-parallel β strands of 5-10 amino acids with a conserved disulfide bond between the two sheets in most, but not all, IgC domains of Ig, TCR, and MHC molecules share the same types of sequence patterns and are called the C1-set within the Ig superfamily. Other IgC domains fall within other sets. IgV domains also share sequence patterns and are called V set domains. IgV domains are longer than IgC domains and contain an additional pair of β strands.

Preferred B7 polypeptides are capable of providing costimulatory or inhibitory signals to immune cells to thereby promote or inhibit immune cell responses. For example, B7 family members that bind to costimulatory receptors increase T cell activation and proliferation, while B7 family members that bind to inhibitory receptors reduce costimulation. Moreover, the same B7 family member may increase or decrease T cell costimulation. For example, when bound to a costimulatory receptor, PD-1 ligand can induce costimulation of immune cells or can inhibit immune cell costimulation, e.g., when present in soluble form. When bound to an inhibitory receptor, PD-1 ligand polypeptides can transmit an inhibitory signal to an immune cell. Preferred B7 family members include B7-1, B7-2, B7h, PD-L1 or PD-L2 and soluble fragments or derivatives thereof. In one embodiment, B7 family members bind to one or more receptors on an immune cell, e.g., CTLA4, CD28, ICOS, PD-1 and/or other receptors, and, depending on the receptor, have the ability to transmit an inhibitory signal or a costimulatory signal to an immune cell, preferably a T cell.

Modulation of a costimulatory signal results in modulation of effector function of an immune cell. Thus, the term "PD-1 ligand activity" includes the ability of a PD-1 ligand polypeptide to bind its natural receptor(s) (e.g. PD-1 or B7-1), the ability to modulate immune cell costimulatory or inhibitory signals, and the ability to modulate the immune response.

The term "PD-L1" refers to a specific PD-1 ligand. Two forms of human PD-L1 molecules have been identified. One form is a naturally occurring PD-L1 soluble polypeptide, i.e., having a short hydrophilic domain and no transmembrane domain, and is referred to herein as PD-L1S (shown in Table 1 as SEQ ID NO: 4). The second form is a cell-associated polypeptide, i.e., having a transmembrane and cytoplasmic domain, referred to herein as PD-L1M (shown in SEQ ID NO: 6). The nucleic acid and amino acid sequences of representative human PD-L1 biomarkers regarding PD-L1M are also available to the public at the GenBank database under NM_014143.3 and NP_054862.1. PD-L1 proteins comprise a signal sequence, and an IgV domain and an IgC domain. The signal sequence of SEQ ID NO: 4 is shown from about amino acid 1 to about amino acid 18. The signal sequence of SEQ ID NO: 6 is shown: from about amino acid 1 to about amino acid 18. The IgV domain of SEQ ID NO: 4 is shown from about amino acid 19 to about amino acid 134 and the IgV domain of SEQ ID NO: 6 is shown from about amino acid 19 to about amino acid 134. The IgC domain of SEQ ID NO: 4 is shown from about amino acid 135 to about amino acid 227 and the IgC domain of SEQ ID NO: 6 is shown from about amino acid 135 to about amino acid 227. The hydrophilic tail of the PD-L1 exemplified in SEQ ID NO: 4 comprises a hydrophilic tail shown from about amino acid 228 to about amino acid 245. The PD-L1 polypeptide exemplified in SEQ ID NO: 6 comprises a transmembrane domain shown from about amino acids 239 to about amino acid 259 of SEQ ID NO: 6 and a cytoplasmic domain shown from about 30 amino acid 260 to about amino acid 290 of SEQ ID NO: 6. In addition, nucleic acid and polypeptide sequences of PD-L1 orthologs in organisms other than humans are well known and include, for example, mouse PD-L1 (NM_021893.3 and NP_068693.1), rat PD-L1 (NM_001191954.1 and NP_001178883.1), dog PD-L1 (XM_541302.3 and XP_541302.3), cow PD-L1 (NM_001163412.1 and NP_001156884.1), and chicken PD-L1 (XM_424811.3 and XP_424811.3).

The term "PD-L2" refers to another specific PD-1 ligand. PD-L2 is a B7 family member expressed on various APCs, including dendritic cells, macrophages and bone-marrow derived mast cells (Zhong et al. (2007) Eur. J. Immunol. 37:2405). APC-expressed PD-L2 is able to both inhibit T cell activation through ligation of PD-1 and costimulate T cell activation, through a PD-1 independent mechanism (Shin et al. (2005) J. Exp. Med. 201:1531). In addition, ligation of dendritic cell-expressed PD-L2 results in enhanced dendritic cell cytokine expression and survival (Radhakrishnan et al. (2003) J. Immunol. 37:1827; Nguyen et al. (2002) J. Exp. Med. 196:1393). The nucleic acid and amino acid sequences of representative human PD-L2 biomarkers (e.g., SEQ ID NOs: 1 and 2) are well known in the art and are also available to the public at the GenBank database under NM_025239.3 and NP_079515.2. PD-L2 proteins are characterized by common structural elements. In some embodiments, PD-L2 proteins include at least one or more of the following domains: a signal peptide domain, a transmembrane domain, an IgV domain, an IgC domain, an extracellular domain, a transmembrane domain, and a cytoplasmic domain. For example, amino acids 1-19 of SEQ ID NO: 2 comprises a signal sequence. As used herein, a "signal sequence" or "signal peptide" serves to direct a polypeptide containing such a sequence to a lipid bilayer, and is cleaved in secreted and membrane bound polypeptides and includes a peptide containing about 15 or more amino acids which occurs at the N-terminus of secretory and membrane bound polypeptides and which contains a large number of hydrophobic amino acid residues. For example, a signal sequence contains at least about 10-30 amino acid residues, preferably about 15-25 amino acid residues, more preferably about 18-20 amino acid residues, and even more preferably about 19 amino acid residues, and has at least about 35-65%, preferably about 38-50%, and more preferably about 40-45% hydrophobic amino acid residues (e.g., valine, leucine, isoleucine or phenylalanine). In another embodiment, amino acid residues 220-243 of the native human PD-L2 polypeptide and amino acid residues 201-243 of the mature polypeptide comprise a transmembrane domain. As used herein, the term "transmembrane domain" includes an amino acid sequence of about 15 amino acid residues in length which spans the plasma membrane. More preferably, a transmembrane domain includes about at least 20, 25, 30, 35, 40, or 45 amino acid residues and spans the plasma membrane. Transmembrane domains are rich in hydrophobic residues, and typically have an alpha-helical structure. In a preferred embodiment, at least 50%, 60%, 70%, 80%, 90%, 95% or more of the amino acids of a transmembrane domain are hydrophobic, e.g., leucines, isoleucines, tyrosines, or tryptophans. Transmembrane domains are described in, for example, Zagotta, W. N. et al. (1996) Annu. Rev. Neurosci. 19: 235-263. In still another embodiment, amino acid residues 20-120 of the native human PD-L2 polypeptide and amino acid residues 1-101 of the mature polypeptide comprise an IgV domain. Amino acid residues 121-219 of the native human PD-L2 polypeptide and amino acid residues 102-200 of the mature polypeptide comprise an IgC domain. As used herein, IgV and IgC domains are recognized in the art as Ig superfamily member domains. These domains correspond to structural units that have distinct folding patterns called Ig folds. Ig folds are comprised of a sandwich of two ß sheets, each consisting of antiparallel (3 strands of 5-10 amino acids with a conserved disulfide bond between the two sheets in most, but not all, domains. IgC domains of Ig, TCR, and MHC molecules share the same types of sequence patterns and are called the C1 set within the Ig superfamily. Other IgC domains fall within other sets. IgV domains also share sequence patterns and are called V set domains. IgV domains are longer than C-domains and form an additional pair of strands. In yet another embodiment, amino acid residues 1-219 of the native human PD-L2 polypeptide and amino acid residues 1-200 of the mature polypeptide comprise an extracellular domain. As used herein, the term "extracellular domain" represents the N-terminal amino acids which extend as a tail from the surface of a cell. An extracellular domain of the present invention includes an IgV domain and an IgC domain, and may include a signal peptide domain. In still another embodiment, amino acid residues 244-273 of the native human PD-L2 polypeptide and amino acid residues 225-273 of the mature polypeptide comprise a cytoplasmic domain. As used herein, the term "cytoplasmic domain" represents the C-terminal amino acids which extend as a tail into the cytoplasm of a cell. In addition, nucleic acid and polypeptide sequences of PD-L2 orthologs in organisms other than humans are well known and include, for example, mouse PD-L2 (NM_021396.2 and NP_067371.1), rat PD-L2 (NM_001107582.2 and NP_001101052.2), dog PD-L2 (XM_847012.2 and XP_852105.2), cow PD-L2 (XM_586846.5 and XP_586846.3), and chimpanzee PD-L2 (XM_001140776.2 and XP_001140776.1).

The term "PD-L2 activity," "biological activity of PD-L2," or "functional activity of PD-L2," refers to an activity exerted by a PD-L2 protein, polypeptide or nucleic acid molecule on a PD-L2-responsive cell or tissue, or on a PD-L2 polypeptide binding partner, as determined in vivo, or in vitro, according to standard techniques. In one embodiment, a PD-L2 activity is a direct activity, such as an association with a PD-L2 binding partner. As used herein, a "target molecule" or "binding partner" is a molecule with which a PD-L2 polypeptide binds or interacts in nature, such that PD-L2-mediated function is achieved. In an exemplary embodiment, a PD-L2 target molecule is the receptor RGMb. Alternatively, a PD-L2 activity is an indirect activity, such as a cellular signaling activity mediated by interaction of the PD-L2 polypeptide with its natural binding partner (i.e., physiologically relevant interacting macromolecule involved in an immune function or other biologically relevant function), e.g., RGMb. The biological activities of PD-L2 are described herein. For example, the PD-L2 polypeptides of the present invention can have one or more of the following activities: 1) bind to and/or modulate the activity of the receptor RGMb, PD-1, or other PD-L2 natural binding partners, 2) modulate intra- or intercellular signaling, 3) modulate activation of immune cells, e.g., T lymphocytes, and 4) modulate the immune response of an organism, e.g., a mouse or human organism.

The term "RGMb" or "DRAGON" refers to a glycosylphophatidylinositol (GPI)-anchored member of the repulsive guidance molecule family, which consists of RGMa, RGMb and RGMc/hemojuvelin (Severyn et al. (2009) Biochem J. 422:393-403). RGMs are glycosylphosphatidylinositol (gpi)-anchored membrane proteins that do not directly signal but act as co-receptors, that modulate the activity of signaling receptors by binding bone morphogenic proteins (BMPs) and neogenin (Conrad et al. (2010) Mol. Cell Neurosci. 43:222-231). RGMb directly binds to BMP-2 or BMP-4, which in turn bind to type I receptors (ALK1, ALK2, ALK3, and ALK6) and type II receptors (BMPRII, ActRIIa and ActRIIb) (Corradini et al. (2009) Cytokine Growth Factor Rev. 20:389-398 and Yoshioka et al. (2012) Eur. J. Immunol. 42:749-759). RGMs coordinate utilization of specific BMP receptors (Corradini et al. (2009) Cytokine Growth Factor Rev. 20:389-398). The function of RGMs was originally described in the developing nervous system where they regulate motility and adhesion of neurons and are critical in embryonic development (Samad et al. (2004) J. Neurosci. 24:2027-2036 and Matsunaga et al. (2004) Nat. Cell Biol. 6:749-755). In addition, RGMb expression is observed in macrophages and other cells of the immune system (Xia et al. (2010) J. Immunol. 186:1369-1376). A role for RGMb in the immune system is only beginning to emerge (Galligan et al. (2007) J. Immunol. 143:2714-2722 and Xia et al. (2010) J. Immunol. 186:1369-1376). For example, the relationship of RGMb-BMP-neogenin signaling in mediating respiratory disorders or that modulating such signaling could effectively treat such respiratory disorders, especially at the effector stage, were not heretofore known.

Co-receptors such as RGMb often have large extracellular domains with multiple motifs enabling them to bind several different ligands. RGMb has been shown to bind neogenin (Bell et al. (2013) Science 341:77-80 and Conrad et al. (2009) Mol. Cell Neurosci. 43:222-231), bone morphogenetic proteins (BMPs) (Samad et al. (2005) J. Biol. Chem. 280:14122-14129 and Xia et al. (2010) J. Am. Soc. Nephrol. 21:666-677), and more recently, programmed death ligand 2 (PD-L2). The nucleic acid and amino acid sequences of representative human RGMb biomarkers (e.g., SEQ ID NOs: 9 and 10) are well known in the art and are also available to the public at the GenBank database under NM_001012761.2 and NP_001012779.2. RGMb proteins are characterized by common structural elements. In some embodiments, RGMb proteins comprise conserved domains with homology to notch-3, phosphatidylinositol-4-phosphate-5-kinase type II beta, insulin-like growth factor binding protein-2, thrombospondin, ephrin type-B receptor 3 precursor, and Slit-2, all of which are known to influence axonal guidance, neurite outgrowth, and other neuronal developmental functions. The C-terminus of RGMb also contains a hydrophobic domain indicative of a 21 amino acid extracellular GPI anchoring. In addition, nucleic acid and polypeptide sequences of RGMb orthologs in organisms other than humans are well known and include, for example, mouse RGMb (NM_178615.3 and NP_848730.2), chimpanzee RGMb (XM_517848.3 and XP_517848.2), cow RGMb (XM_002689413.1 and XP_002689459.1), chicken RGMb (XM_42860.3 and XP_424860.3), and zebrafish RGMb (NM_001001727.1 and NP_001001727.1).

Apart from its role in immunomodulation via the RGMb-PD-L2 interaction, RGMb is also physiologically relevant to the "RGMb-NEO1-BMP signaling pathway," which refers to one of the intracellular signaling pathways activated by the binding of BMP factors to RGMb and NEO1 co-receptors. Without being bound by theory, it is believed that the RGMb-NEO1-BMP signaling pathway signals according to a model whereby RGMb forms a signaling supercomplex of BMP-BMP receptors-RGMb-Neogenin (BBRN supercomplex). RGMb directly binds to BMP-2 or BMP-4 as natural binding partners, which bind to type I BMP receptors (BMPR1a, BMPR1b, ACVR1, ACVRL1) and recruit type II BMP receptors (BMPR2, ACVR2a, ACVR2b) (Corradini et al. (2009) Cytokine Growth Factor Rev. 20:389-398 and Yoshioka et al. (2012) Eur. J. Immunol. 42:749-759). Then, type II BMP receptors phosphorylate type I BMP receptors, which phosphorylate Smad1/5/8 or p38 mitogen activated protein kinase (MAPK) and extracellular signal-regulated protein kinase (ERK), leading to downstream target gene transcription (Corradini et al.

(2009) *Cytokine Growth Factor Rev.* 20:389-398 and Xia et al. (2010) *J. Immunol.* 186:1369-1376). RGMs facilitate the utilization of ACVR2a by BMP-2/4. In the absence of an RGM, BMP-2/4 preferentially utilize BMPR2 (Corradini et al. (2009) *Cytokine Growth Factor Rev.* 20:389-398). RGMb may also signal through neogenin as a natural binding partner and downstream effector Rho, triggering cytoskeletal rearrangement (Bell et al. (2013) *Science* 341:77-80 and Conrad et al. (2007) *J. Biol. Chem.* 282:16423-16433). PD-L2 may interact with this BBRN supercomplex by binding to RGMb, and modulate these signaling pathways. For example, PD-L2 binding to PD-1 which results in tyrosine phosphorylation of the PD-1 cytoplasmic domain, recruitment of tyrosine phosphatases, particularly SHP-2, and attenuation of antigen receptor signals. Thus, PD-L2 may participate in three important signaling circuits, the PD-1, BMP, and neogenin signaling pathways, by binding to either PD-1 or RGMb. In some embodiments, the RGMb-NEO1-BMP signaling pathway is limited to subsets of biomolecules within the pathway, such as RGMb, NEO1, BMP2, and BMP4, or even individual biomolecules within the pathway, such as RGMb. Exemplary agents useful for inhibiting the RGMb-NEO1-BMP signaling pathway, or other biomarkers described herein, include antibodies, small molecules, peptides, peptidomimetics, natural ligands, and derivatives of natural ligands, that can either bind and/or inactivate or inhibit target proteins, or fragments thereof as well as RNA interference, antisense, nucleic acid aptamers, etc. that can downregulate the expression and/or activity of target nucleic acids, or fragments thereof. In some embodiments, a single agent or a combination of agents can be used to disrupt signaling by the BBRN supercomplex. Exemplary inhibitors of the RGMb-NEO1-BMP signaling pathway are also well known in the art and include, but are not limited to BMP inhibitors, such as inhibitors of BMP2 and BMP4 include noggin, chrodin, Cerl, DAN, WISE (USAG-1), SOST (Extodin), and Gremlin, as well as antibodies, nucleic acids, and extracellular domains of BMP receptors such as soluble activin extracellular domains. Similarly, antibodies that bind to RGMb and/or neogenin to block the interaction with its natural binding partners are contemplated, as well as the use of such natural binding partners, or soluble fragments thereof.

TABLE 1

```
SEQ ID NO: 1 Human PD-L2 cDNA Acid Sequence
atg atc ttc ctc ctg cta atg ttg agc ctg gaa ttg cag ctt cac cag    48
Met Ile Phe Leu Leu Leu Met Leu Ser Leu Glu Leu Gln Leu His Gln
 1               5                  10                  15 ata gca gct tta ttc aca gtg aca gtc cct aag gaa ctg tac ata ata    96
Ile Ala Ala Leu Phe Thr Val Thr Val Pro Lys Glu Leu Tyr Ile Ile
                20                  25                  30 gag cat ggc agc aat gtg acc ctg gaa tgc aac ttt gac act gga agt   144
Glu His Gly Ser Asn Val Thr Leu Glu Cys Asn Phe Asp Thr Gly Ser
            35                  40                  45 cat gtg aac ctt gga gca ata aca gcc agt ttg caa aag gtg gaa aat   192
His Val Asn Leu Gly Ala Ile Thr Ala Ser Leu Gln Lys Val Glu Asn
        50                  55                  60 gat aca tcc cca cac cgt gaa aga gcc act ttg ctg gag gag cag ctg   240
Asp Thr Ser Pro His Arg Glu Arg Ala Thr Leu Leu Glu Glu Gln Leu
65                  70                  75                  80 ccc cta ggg aag gcc tcg ttc cac ata cct caa gtc caa gtg agg gac   288
Pro Leu Gly Lys Ala Ser Phe His Ile Pro Gln Val Gln Val Arg Asp
                85                  90                  95 gaa gga cag tac caa tgc ata atc atc tat ggg gtc gcc tgg gac tac   336
Glu Gly Gln Tyr Gln Cys Ile Ile Ile Tyr Gly Val Ala Trp Asp Tyr
                100                 105                 110 aag tac ctg act ctg aaa gtc aaa gct tcc tac agg aaa ata aac act   384
Lys Tyr Leu Thr Leu Lys Val Lys Ala Ser Tyr Arg Lys Ile Asn Thr
            115                 120                 125 cac atc cta aag gtt cca gaa aca gat gag gta gag ctc acc tgc cag   432
His Ile Leu Lys Val Pro Glu Thr Asp Glu Val Glu Leu Thr Cys Gln
        130                 135                 140 gct aca ggt tat cct ctg gca gaa gta tcc tgg cca aac gtc agc gtt   480
Ala Thr Gly Tyr Pro Leu Ala Glu Val Ser Trp Pro Asn Val Ser Val
145                 150                 155                 160 cct gcc aac acc agc cac tcc agg acc cct gaa ggc ctc tac cag gtc   528
Pro Ala Asn Thr Ser His Ser Arg Thr Pro Glu Gly Leu Tyr Gln Val
                165                 170                 175 acc agt gtt ctg cgc cta aag cca ccc cct ggc aga aac ttc agc tgt   576
Thr Ser Val Leu Arg Leu Lys Pro Pro Pro Gly Arg Asn Phe Ser Cys
                180                 185                 190 gtg ttc tgg aat act cac gtg agg gaa ctt act ttg gcc agc att gac   624
Val Phe Trp Asn Thr His Val Arg Glu Leu Thr Leu Ala Ser Ile Asp
                195                 200                 205
```

TABLE 1-continued

```
ctt caa agt cag atg gaa ccc agg acc cat cca act tgg ctg ctt cac    672
Leu Gln Ser Gln Met Glu Pro Arg Thr His Pro Thr Trp Leu Leu His
    210             215                 220 att ttc atc ccc tcc tgc atc att gct ttc att ttc ata gcc aca gtg    720
Ile Phe Ile Pro Ser Cys Ile Ile Ala Phe Ile Phe Ile Ala Thr Val
225             230                 235                 240 ata gcc cta aga aaa caa ctc tgt caa aag ctg tat tct tca aaa gac    768
Ile Ala Leu Arg Lys Gln Leu Cys Gln Lys Leu Tyr Ser Ser Lys Asp
                245                 250                 255 aca aca aaa aga cct gtc acc aca aca aag agg gaa gtg aac agt gct    816
Thr Thr Lys Arg Pro Val Thr Thr Thr Lys Arg Glu Val Asn Ser Ala
            260                 265                 270 atc                                                                 819
Ile

SEQ ID NO: 2 Human PD-L2 Amino Acid Sequence
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
                20                  25                  30

Glu His Gly Ser Asn Val Thr Leu Glu Cys Asn Phe Asp Thr Gly Ser
            35                  40                  45

His Val Asn Leu Gly Ala Ile Thr Ala Ser Leu Gln Lys Val Glu Asn
        50                  55                  60

Asp Thr Ser Pro His Arg Glu Arg Ala Thr Leu Leu Glu Glu Gln Leu
65                  70                  75                  80

Pro Leu Gly Lys Ala Ser Phe His Ile Pro Gln Val Gln Val Arg Asp
                85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
    130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
    210                 215                 220

Ile Phe Ile Pro Ser Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
            260                 265                 270

Ile

SEQ ID NO: 3 Human PD-L1S cDNA Acid Sequence
gcttcccgag gctccgcacc agccgcgctt ctgtccgcct gcagggcatt ccagaaag     58
atg agg ata ttt gct gtc ttt ata ttc atg acc tac tgg cat ttg ctg    106
Met Arg Ile Phe Ala Val Phe Ile Phe Met Thr Tyr Trp His Leu Leu
1               5                   10                  15
```

TABLE 1-continued

```
aac gca ttt act gtc acg gtt ccc aag gac cta tat gtg gta gag tat    154
Asn Ala Phe Thr Val Thr Val Pro Lys Asp Leu Tyr Val Val Glu Tyr
             20                  25                  30 ggt agc aat atg aca att gaa tgc aaa ttc cca gta gaa aaa caa tta    202
Gly Ser Asn Met Thr Ile Glu Cys Lys Phe Pro Val Glu Lys Gln Leu
         35                  40                  45 gac ctg gct gca cta att gtc tat tgg gaa atg gag gat aag aac att    250
Asp Leu Ala Ala Leu Ile Val Tyr Trp Glu Met Glu Asp Lys Asn Ile
     50                  55                  60 att caa ttt gtg cat gga gag gaa gac ctg aag gtt cag cat agt agc    298
Ile Gln Phe Val His Gly Glu Glu Asp Leu Lys Val Gln His Ser Ser
 65                  70                  75                  80 tac aga cag agg gcc cgg ctg ttg aag gac cag ctc tcc ctg gga aat    346
Tyr Arg Gln Arg Ala Arg Leu Leu Lys Asp Gln Leu Ser Leu Gly Asn
                 85                  90                  95 gct gca ctt cag atc aca gat gtg aaa ttg cag gat gca ggg gtg tac    394
Ala Ala Leu Gln Ile Thr Asp Val Lys Leu Gln Asp Ala Gly Val Tyr
            100                 105                 110 cgc tgc atg atc agc tat ggt ggt gcc gac tac aag cga att act gtg    442
Arg Cys Met Ile Ser Tyr Gly Gly Ala Asp Tyr Lys Arg Ile Thr Val
        115                 120                 125 aaa gtc aat gcc cca tac aac aaa atc aac caa aga att ttg gtt gtg    490
Lys Val Asn Ala Pro Tyr Asn Lys Ile Asn Gln Arg Ile Leu Val Val
    130                 135                 140 gat cca gtc acc tct gaa cat gaa ctg aca tgt cag gct gag ggc tac    538
Asp Pro Val Thr Ser Glu His Glu Leu Thr Cys Gln Ala Glu Gly Tyr
145                 150                 155                 160 ccc aag gcc gaa gtc atc tgg aca agc agt gac cat caa gtc ctg agt    586
Pro Lys Ala Glu Val Ile Trp Thr Ser Ser Asp His Gln Val Leu Ser
                165                 170                 175 ggt aag acc acc acc acc aat tcc aag aga gag gag aag ctt ttc aat    634
Gly Lys Thr Thr Thr Thr Asn Ser Lys Arg Glu Glu Lys Leu Phe Asn
            180                 185                 190 gtg acc agc aca ctg aga atc aac aca aca act aat gag att ttc tac    682
Val Thr Ser Thr Leu Arg Ile Asn Thr Thr Thr Asn Glu Ile Phe Tyr
        195                 200                 205 tgc act ttt agg aga tta gat cct gag gaa aac cat aca gct gaa ttg    730
Cys Thr Phe Arg Arg Leu Asp Pro Glu Glu Asn His Thr Ala Glu Leu
    210                 215                 220 gtc atc cca ggt aat att ctg aat gtg tcc att aaa ata tgt cta aca    778
Val Ile Pro Gly Asn Ile Leu Asn Val Ser Ile Lys Ile Cys Leu Thr
225                 230                 235                 240 ctg tcc cct agc acc tagcatgatg tctgcctatc atagtcattc agtgattgtt   833
Leu Ser Pro Ser Thr
                245 gaataaatga atgaatgaat aacactatgt ttacaaaata tatcctaatt cctcacctcc   893 attcatccaa accatattgt tacttaataa acattcagca gatatttatg gaataaaaaa   953 aaaaaaaaaa aaaaa                                                   968

SEQ ID NO: 4 Human PD-L1S Amino Acid Sequence
Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
             20                  25                  30

Gly Ser Asn Met Thr Ile Glu Cys Lys Phe Pro Val Glu Lys Gln Leu
         35                  40                  45

Asp Leu Ala Ala Leu Ile Val Tyr Trp Glu Met Glu Asp Lys Asn Ile
     50                  55                  60
```

TABLE 1-continued

```
Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
             100                 105                 110

Arg Cys Met Ile Ser Tyr Gly Gly Ala Asp Tyr Lys Arg Ile Thr Val
         115                 120                 125

Lys Val Asn Ala Pro Tyr Asn Lys Ile Asn Gln Arg Ile Leu Val Val
     130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                 165                 170                 175

Gly Lys Thr Thr Thr Thr Asn Ser Lys Arg Glu Glu Lys Leu Phe Asn
             180                 185                 190

Val Thr Ser Thr Leu Arg Ile Asn Thr Thr Thr Asn Glu Ile Phe Tyr
         195                 200                 205

Cys Thr Phe Arg Arg Leu Asp Pro Glu Glu Asn His Thr Ala Glu Leu
     210                 215                 220

Val Ile Pro Gly Asn Ile Leu Asn Val Ser Ile Lys Ile Cys Leu Thr
225                 230                 235                 240

Leu Ser Pro Ser Thr
                245
```

SEQ ID NO: 5 Human PD-L1M cDNA Acid Sequence

```
cgaggctccg caccagccgc gcttctgtcc gcctgcaggg cattccagaa agatgagg    58
                                                        Met Arg
                                                          1 ata ttt gct gtc ttt ata ttc atg acc tac tgg cat ttg ctg aac gca   106
Ile Phe Ala Val Phe Ile Phe Met Thr Tyr Trp His Leu Leu Asn Ala
        5                   10                  15 ttt act gtc acg gtt ccc aag gac cta tat gtg gta gag tat ggt agc   154
Phe Thr Val Thr Val Pro Lys Asp Leu Tyr Val Val Glu Tyr Gly Ser
 20                  25                  30 aat atg aca att gaa tgc aaa ttc cca gta gaa aaa caa tta gac ctg   202
Asn Met Thr Ile Glu Cys Lys Phe Pro Val Glu Lys Gln Leu Asp Leu
 35              40                  45                  50 gct gca cta att gtc tat tgg gaa atg gag gat aag aac att att caa   250
Ala Ala Leu Ile Val Tyr Trp Glu Met Glu Asp Lys Asn Ile Ile Gln
                 55                  60                  65 ttt gtg cat gga gag gaa gac ctg aag gtt cag cat agt agc tac aga   298
Phe Val His Gly Glu Glu Asp Leu Lys Val Gln His Ser Ser Tyr Arg
             70                  75                  80 cag agg gcc cgg ctg ttg aag gac cag ctc tcc ctg gga aat gct gca   346
Gln Arg Ala Arg Leu Leu Lys Asp Gln Leu Ser Leu Gly Asn Ala Ala
         85                  90                  95 ctt cag atc aca gat gtg aaa ttg cag gat gca ggg gtg tac cgc tgc   394
Leu Gln Ile Thr Asp Val Lys Leu Gln Asp Ala Gly Val Tyr Arg Cys
     100                 105                 110 atg atc agc tat ggt ggt gcc gac tac aag cga att act gtg aaa gtc   442
Met Ile Ser Tyr Gly Gly Ala Asp Tyr Lys Arg Ile Thr Val Lys Val
115                 120                 125                 130 aat gcc cca tac aac aaa atc aac caa aga att ttg gtt gtg gat cca   490
Asn Ala Pro Tyr Asn Lys Ile Asn Gln Arg Ile Leu Val Val Asp Pro
                 135                 140                 145
```

TABLE 1-continued

```
gtc acc tct gaa cat gaa ctg aca tgt cag gct gag ggc tac ccc aag      538
Val Thr Ser Glu His Glu Leu Thr Cys Gln Ala Glu Gly Tyr Pro Lys
        150                 155                 160 gcc gaa gtc atc tgg aca agc agt gac cat caa gtc ctg agt ggt aag      586
Ala Glu Val Ile Trp Thr Ser Ser Asp His Gln Val Leu Ser Gly Lys
            165                 170                 175 acc acc acc acc aat tcc aag aga gag gag aag ctt ttc aat gtg acc      634
Thr Thr Thr Thr Asn Ser Lys Arg Glu Glu Lys Leu Phe Asn Val Thr
                180                 185                 190 agc aca ctg aga atc aac aca aca act aat gag att ttc tac tgc act      682
Ser Thr Leu Arg Ile Asn Thr Thr Thr Asn Glu Ile Phe Tyr Cys Thr
195                 200                 205                 210 ttt agg aga tta gat cct gag gaa aac cat aca gct gaa ttg gtc atc      730
Phe Arg Arg Leu Asp Pro Glu Glu Asn His Thr Ala Glu Leu Val Ile
                215                 220                 225 cca gaa cta cct ctg gca cat cct cca aat gaa agg act cac ttg gta      778
Pro Glu Leu Pro Leu Ala His Pro Pro Asn Glu Arg Thr His Leu Val
            230                 235                 240 att ctg gga gcc atc tta tta tgc ctt ggt gta gca ctg aca ttc atc      826
Ile Leu Gly Ala Ile Leu Leu Cys Leu Gly Val Ala Leu Thr Phe Ile
        245                 250                 255 ttc cgt tta aga aaa ggg aga atg atg gat gtg aaa aaa tgt ggc atc      874
Phe Arg Leu Arg Lys Gly Arg Met Met Asp Val Lys Lys Cys Gly Ile
    260                 265                 270 caa gat aca aac tca aag aag caa agt gat aca cat ttg gag gag acg      922
Gln Asp Thr Asn Ser Lys Lys Gln Ser Asp Thr His Leu Glu Glu Th
275                 280                 285                 290 taatccagca ttgaacttc tgatcttcaa gcagggattc tcaacctgtg gtttagggt      982 tcatcgggc tgagcgtgac aagaggaagg aatgggcccg tgggatgcag gcaatgtggg   1042
acttaaaagg cccaagcact gaaaatggaa cctggcgaaa gcagaggagg agaatgaaga   1102
aagatggagt caaacaggga gcctggaggg agaccttgat actttcaaat gcctgagggg   1162
ctcatcgacg cctgtgacag ggagaaagga tacttctgaa caaggagcct ccaagcaaat   1222
catccattgc tcatcctagg aagacgggtt gagaatccct aatttgaggg tcagttcctg   1282
cagaagtgcc ctttgcctcc actcaatgcc tcaatttgtt ttctgcatga ctgagagtct   1342
cagtgttgga acgggacagt atttatgtat gagtttttcc tatttatttt gagtctgtga   1402
ggtcttcttg tcatgtgagt gtggttgtga atgatttctt ttgaagatat attgtagtag   1462
atgttacaat tttgtcgcca aactaaactt gctgcttaat gatttgctca catctagtaa   1522
aacatggagt atttgtaaaa aaaaaaaaaa a                                  1553

SEQ ID NO: 6 Human PD-L1M Amino Acid Sequence
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
                20                  25                  30

Gly Ser Asn Met Thr Ile Glu Cys Lys Phe Pro Val Glu Lys Gln Leu
            35                  40                  45

Asp Leu Ala Ala Leu Ile Val Tyr Trp Glu Met Glu Asp Lys Asn Ile
        50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110
```

TABLE 1-continued

```
Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
            165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
            245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
            275                 280                 285

Glu Thr
    290
```

*Included in Table 1 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 1, or a portion thereof Such nucleic acid molecules can have a function of the full-length nucleic acid as described further herein.
*Included in Table 1 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 1, or a portion thereof. Such polypeptides can have a function of the full-length polypeptide as described further herein.
*Included in Table 1 is PD-L2, including any PD-L2 cDNA or polypeptide.

TABLE 2

```
SEQ ID NO: 7 Human PD-1 cDNA Squence
cactctggtg gggctgctcc aggc atg cag atc cca cag gcg ccc tgg cca        51
                          Met Gln Ile Pro Gln Ala Pro Trp Pro
                            1               5 gtc gtc tgg gcg gtg cta caa ctg ggc tgg cgg cca gga tgg ttc tta        99
Val Val Trp Ala Val Leu Gln Leu Gly Trp Arg Pro Gly Trp Phe Leu
 10                  15                  20                  25 gac tcc cca gac agg ccc tgg aac ccc ccc acc ttc tcc cca gcc ctg       147
Asp Ser Pro Asp Arg Pro Trp Asn Pro Pro Thr Phe Ser Pro Ala Leu
                 30                  35                  40 ctc gtg gtg acc gaa ggg gac aac gcc acc ttc acc tgc agc ttc tcc       195
Leu Val Val Thr Glu Gly Asp Asn Ala Thr Phe Thr Cys Ser Phe Ser
             45                  50                  55 aac aca tcg gag agc ttc gtg cta aac tgg tac cgc atg agc ccc agc       243
Asn Thr Ser Glu Ser Phe Val Leu Asn Trp Tyr Arg Met Ser Pro Ser
         60                  65                  70 aac cag acg gac aag ctg gcc gcc ttc ccc gag gac cgc agc cag ccc       291
Asn Gln Thr Asp Lys Leu Ala Ala Phe Pro Glu Asp Arg Ser Gln Pro
     75                  80                  85 ggc cag gac tgc cgc ttc cgt gtc aca caa ctg ccc aac ggg cgt gac       339
Gly Gln Asp Cys Arg Phe Arg Val Thr Gln Leu Pro Asn Gly Arg Asp
 90                  95                 100                 105
```

TABLE 2 -continued

```
ttc cac atg agc gtg gtc agg gcc cgg cgc aat gac agc ggc acc tac    387
Phe His Met Ser Val Val Arg Ala Arg Arg Asn Asp Ser Gly Thr Tyr
            110                 115                 120 ctc tgt ggg gcc atc tcc ctg gcc ccc aag gcg cag atc aaa gag agc    435
Leu Cys Gly Ala Ile Ser Leu Ala Pro Lys Ala Gln Ile Lys Glu Ser
            125                 130                 135 ctg cgg gca gag ctc agg gtg aca gag aga agg gca gaa gtg ccc aca    483
Leu Arg Ala Glu Leu Arg Val Thr Glu Arg Arg Ala Glu Val Pro Thr
            140                 145                 150 gcc cac ccc agc ccc tca ccc agg tca gcc ggc cag ttc caa acc ctg    531
Ala His Pro Ser Pro Ser Pro Arg Ser Ala Gly Gln Phe Gln Thr Leu
            155                 160                 165 gtg gtt ggt gtc gtg ggc ggc ctg ctg ggc agc ctg gtg ctg cta gtc    579
Val Val Gly Val Val Gly Gly Leu Leu Gly Ser Leu Val Leu Leu Val
170                 175                 180                 185 tgg gtc ctg gcc gtc atc tgc tcc cgg gcc gca cga ggg aca ata gga    627
Trp Val Leu Ala Val Ile Cys Ser Arg Ala Ala Arg Gly Thr Ile Gly
                    190                 195                 200 gcc agg cgc acc ggc cag ccc ctg aag gag gac ccc tca gcc gtg cct    675
Ala Arg Arg Thr Gly Gln Pro Leu Lys Glu Asp Pro Ser Ala Val Pro
            205                 210                 215 gtg ttc tct gtg gac tat ggg gag ctg gat ttc cag tgg cga gag aag    723
Val Phe Ser Val Asp Tyr Gly Glu Leu Asp Phe Gln Trp Arg Glu Lys
            220                 225                 230 acc ccg gag ccc ccc gtg ccc tgt gtc cct gag cag acg gag tat gcc    771
Thr Pro Glu Pro Pro Val Pro Cys Val Pro Glu Gln Thr Glu Tyr Ala
            235                 240                 245 acc att gtc ttt cct agc gga atg ggc acc tca tcc ccc gcc cgc agg    819
Thr Ile Val Phe Pro Ser Gly Met Gly Thr Ser Ser Pro Ala Arg Arg
250                 255                 260                 265 ggc tca gct gac ggc cct cgg agt gcc cag cca ctg agg cct gag gat    867
Gly Ser Ala Asp Gly Pro Arg Ser Ala Gln Pro Leu Arg Pro Glu Asp
                    270                 275                 280 gga cac tgc tct tgg ccc ctc tgaccggctt ccttggccac cagtgttctg cag   921
Gly His Cys Ser Trp Pro Leu
            285

SEQ ID NO: 8 Human PD-1 Amino Acid Sequence
Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160
```

TABLE 2 -continued

```
Arg Ser Ala Gly Gln Phe Gln Thr Leu Val Val Gly Val Val Gly Gly
                    165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
        210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                    245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285
```

SEQ ID NO: 9 Human RGMb cDNA Sequence
```
   1    atgataagga agaagaggaa gcgaagcgcg ccccccggcc catgccgcag ccacgggccc
  61    agacccgcca cggcgcccgc gccgccgccc tcgccggagc ccacgagacc tgcatggacg
 121    ggcatgggct tgagagcagc accttccagc cgccgccgct gccgccgccga ggttgagcag
 181    cgccgcagcc ccgggctctg cccccgccg ctggagctgc tgctgctgct gctgttcagc
 241    ctcgggctgc tccacgcagg tgactgccaa cagccagccc aatgtcgaat ccagaaatgc
 301    accacggact tcgtgtccct gacttctcac ctgaactctg ccgttgacgg ctttgactct
 361    gagttttgca aggccttgcg tgcctatgct ggctgcaccc agcgaacttc aaaagcctgc
 421    cgtggcaacc tggtatacca ttctgccgtg ttgggtatca gtgacctcat gagccagagg
 481    aattgttcca aggatggacc cacatcctct accaaccccg aagtgaccca tgatccttgc
 541    aactatcaca gccacgctgg agccagggaa cacaggagag gggaccagaa ccctcccagt
 601    taccttttt gtggcttgtt tggagatcct cacctcagaa cttcaagga taacttccaa
 661    acatgcaaag tagaaggggc ctggccactc atagataata attatctttc agttcaagtg
 721    acaaacgtac ctgtggtccc tggatccagt gctactgcta caaataagat cactattatc
 781    ttcaaagccc accatgagtg tacagatcag aaagtctacc aagctgtgac agatgacctg
 841    ccggccgcct ttgtggatgg caccaccagt ggtggggaca gcgatgccaa gagcctgcgt
 901    atcgtggaaa gggagagtgg ccactatgtg gagatgcacg cccgctatat agggaccaca
 961    gtgtttgtgc ggcaggtggg tcgctacctg accccttgcca tccgtatgcc tgaagacctg
1021    gccatgtcct acgaggagag ccaggacctg cagctgtgcg tgaacgctgc cccctgagt
1081    gaacgcatcg atgacgggca gggccaggtg tctgccatcc tgggacacag cctgcctcgc
1141    acctccttgg tgcaggcctg gcctggctac acactggaga ctgccaacac tcaatgccat
1201    gagaagatgc cagtgaagga catctatttc agtcctgtg tcttcgacct gctcaccact
1261    ggtgatgcca actttactgc cgcagcccac agtgccttgg aggatgtgga ggccctgcac
1321    ccaaggaagg aacgctggca cattttcccc agcagtggca atgggactcc cgtggaggc
1381    agtgatttgt ctgtcagtct aggactcacc tgcttgatcc ttatcgtgtt tttgtag
```

SEQ ID NO: 10 Human RGMb Amino Acid Sequence
```
   1    mirkkrkrsa ppgpcrshgp rpatapappp speptrpawt gmglraapss aaaaaeveq
  61    rrspglcppp lelllllfs lgllhagdcq gpagcriqkc ttdfvsltsh lnsavdgfds
 121    efckalraya gctqrtskac rgnlvyhsav lgisdlmsqr ncskdgptss tnpevthdpc
```

TABLE 2 -continued

```
181      nyhshagare hrrgdqnpps ylfcglfgdp hlrtfkdnfq tckvegawpl idnnylsvqv 241      tnvpvvpgss atatnkitii fkahhectdq kvyqavtddl paafvdgtts ggdsdakslr 301      iveresghyv emharyigtt vfvrqvgryl tlairmpedl amsyeesqdl qlcvngcpls 361      eriddgqgqv sailghslpr tslvgawpgy tletantqch ekmpvkdiyf qscvfdlltt 421      gdanftaaah saledvealh prkerwhifp ssgngtprgg sdlsyslglt clilivfl
```

*Included in Table 2 are RNA nucleic acid molecules (e.g., thymines replaced with uredines), nucleic acid molecules encoding orthologs of the encoded proteins, as well as DNA or RNA nucleic acid sequences comprising a nucleic acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with the nucleic acid sequence of any SEQ ID NO listed in Table 2, or a portion thereof Such nucleic acid molecules can have a function of the full-length nucleic acid as described further herein.
*Included in Table 2 are orthologs of the proteins, as well as polypeptide molecules comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99%, 99.5%, or more identity across their full length with an amino acid sequence of any SEQ ID NO listed in Table 2, or a portion thereof. Such polypeptides can have a function of the full-length polypeptide as described further herein.

II. Subjects

In one embodiment, the subject for whom predicted likelihood of efficacy of a PD-1 pathway inhibitor therapy is determined, is a mammal (e.g., mouse, rat, primate, non-human mammal, domestic animal, such as a dog, cat, cow, horse, and the like), and is preferably a human.

In another embodiment of the methods of the present invention, the subject has not undergone treatment, such as chemotherapy, radiation therapy, targeted therapy, and/or anti-immune checkpoint therapy. In still another embodiment, the subject has undergone treatment, such as chemotherapy, radiation therapy, targeted therapy, and/or anti-immune checkpoint therapy.

In certain embodiments, the subject has had surgery to remove cancerous or precancerous tissue. In other embodiments, the cancerous tissue has not been removed, e.g., the cancerous tissue may be located in an inoperable region of the body, such as in a tissue that is essential for life, or in a region where a surgical procedure would cause considerable risk of harm to the patient.

The methods of the present invention can be used to determine the responsiveness to PD-1 pathway inhibitor therapies of many different esophagogastric cancers or metaplasias in subjects such as those described herein.

III. Sample Collection, Preparation and Separation

In some embodiments, biomarker amount and/or activity measurement(s) in a sample from a subject is compared to a predetermined control (standard) sample. The sample from the subject is typically from a diseased tissue, such as cancer cells or tissues. The control sample can be from the same subject or from a different subject. The control sample is typically a normal, non-diseased sample. However, in some embodiments, such as for staging of disease or for evaluating the efficacy of treatment, the control sample can be from a diseased tissue. The control sample can be a combination of samples from several different subjects. In some embodiments, the biomarker amount and/or activity measurement(s) from a subject is compared to a pre-determined level. This pre-determined level is typically obtained from normal samples. As described herein, a "pre-determined" biomarker amount and/or activity measurement(s) may be a biomarker amount and/or activity measurement(s) used to, by way of example only, evaluate a subject that may be selected for treatment, evaluate a response to a PD-1 pathway inhibitor therapy, and/or evaluate a response to a combination PD-1 pathway inhibitor therapy (e.g., one or more PD-1 pathway inhibitors alone, or in combination with one or more additional immune checkpoint inhibitors). A pre-determined biomarker amount and/or activity measurement(s) may be determined in populations of patients with or without cancer. The pre-determined biomarker amount and/or activity measurement(s) can be a single number, equally applicable to every patient, or the pre-determined biomarker amount and/or activity measurement(s) can vary according to specific subpopulations of patients. Age, weight, height, and other factors of a subject may affect the pre-determined biomarker amount and/or activity measurement(s) of the individual. Furthermore, the pre-determined biomarker amount and/or activity can be determined for each subject individually. In one embodiment, the amounts determined and/or compared in a method described herein are based on absolute measurements.

In another embodiment, the amounts determined and/or compared in a method described herein are based on relative measurements, such as ratios (e.g., biomarker copy numbers, level, and/or activity before a treatment vs. after a treatment, such biomarker measurements relative to a spiked or man-made control, such biomarker measurements relative to the expression of a housekeeping gene, and the like). For example, the relative analysis can be based on the ratio of pre-treatment biomarker measurement as compared to post-treatment biomarker measurement. Pre-treatment biomarker measurement can be made at any time prior to initiation of anti-cancer therapy. Post-treatment biomarker measurement can be made at any time after initiation of anti-cancer therapy. In some embodiments, post-treatment biomarker measurements are made 1, 2, 3, 4, 5, 6, 7, 8, 9, 10, 11, 12, 13, 14, 15, 16, 17, 18, 19, 20 weeks or more after initiation of anti-cancer therapy, and even longer toward indefinitely for continued monitoring. Treatment can comprise anti-cancer therapy, such as a therapeutic regimen comprising one or more PD-1 pathway inhibitors alone or in combination with other anti-cancer agents, such as other immune checkpoint inhibitors.

The pre-determined biomarker amount and/or activity measurement(s) can be any suitable standard. For example, the pre-determined biomarker amount and/or activity measurement(s) can be obtained from the same or a different human for whom a patient selection is being assessed. In one embodiment, the pre-determined biomarker amount and/or activity measurement(s) can be obtained from a previous assessment of the same patient. In such a manner, the progress of the selection of the patient can be monitored over time. In addition, the control can be obtained from an assessment of another human or multiple humans, e.g., selected groups of humans, if the subject is a human. In such a manner, the extent of the selection of the human for whom selection is being assessed can be compared to suitable other humans, e.g., other humans who are in a similar situation to the human of interest, such as those suffering from similar or the same condition(s) and/or of the same ethnic group.

In some embodiments of the present invention the change of biomarker amount and/or activity measurement(s) from the pre-determined level is about 0.1, 0.2, 0.3, 0.4, 0.5, 0.6, 0.7, 0.8, 0.9, 1.0, 1.5, 2.0, 2.5, 3.0, 3.5, 4.0, 4.5, or 5.0 fold or greater, or any range in between, inclusive. Such cutoff values apply equally when the measurement is based on relative changes, such as based on the ratio of pre-treatment biomarker measurement as compared to post-treatment biomarker measurement.

Biological samples can be collected from a variety of sources from a patient including a body fluid sample, cell sample, or a tissue sample comprising nucleic acids and/or proteins. "Body fluids" refer to fluids that are excreted or secreted from the body as well as fluids that are normally not (e.g., amniotic fluid, aqueous humor, bile, blood and blood plasma, cerebrospinal fluid, cerumen and earwax, cowper's fluid or pre-ejaculatory fluid, chyle, chyme, stool, female ejaculate, interstitial fluid, intracellular fluid, lymph, menses, breast milk, mucus, pleural fluid, pus, saliva, sebum, semen, serum, sweat, synovial fluid, tears, urine, vaginal lubrication, vitreous humor, vomit). In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. IN another embodiment, the sample is serum.

The samples can be collected from individuals repeatedly over a longitudinal period of time (e.g., once or more on the order of days, weeks, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

Ultracentrifugation is a method for removing undesired polypeptides from a sample. Ultracentrifugation is the centrifugation of a sample at about 15,000-60,000 rpm while monitoring with an optical system the sedimentation (or lack thereof) of particles. Electrodialysis is a procedure which uses an electromembrane or semipermeable membrane in a process in which ions are transported through semi-permeable membranes from one solution to another under the influence of a potential gradient. Since the membranes used in electrodialysis may have the ability to selectively transport ions having positive or negative charge, reject ions of the opposite charge, or to allow species to migrate through a semipermeable membrane based on size and charge, it renders electrodialysis useful for concentration, removal, or separation of electrolytes.

Separation and purification in the present invention may include any procedure known in the art, such as capillary electrophoresis (e.g., in capillary or on-chip) or chromatography (e.g., in capillary, column or on a chip). Electrophoresis is a method which can be used to separate ionic molecules under the influence of an electric field. Electrophoresis can be conducted in a gel, capillary, or in a microchannel on a chip. Examples of gels used for electrophoresis include starch, acrylamide, polyethylene oxides, agarose, or combinations thereof. A gel can be modified by its cross-linking, addition of detergents, or denaturants, immobilization of enzymes or antibodies (affinity electrophoresis) or substrates (zymography) and incorporation of a pH gradient. Examples of capillaries used for electrophoresis include capillaries that interface with an electrospray.

Capillary electrophoresis (CE) is preferred for separating complex hydrophilic molecules and highly charged solutes. CE technology can also be implemented on microfluidic chips. Depending on the types of capillary and buffers used, CE can be further segmented into separation techniques such as capillary zone electrophoresis (CZE), capillary isoelectric focusing (CIEF), capillary isotachophoresis (cITP) and capillary electrochromatography (CEC). An embodiment to couple CE techniques to electrospray ionization involves the use of volatile solutions, for example, aqueous mixtures containing a volatile acid and/or base and an organic such as an alcohol or acetonitrile.

Capillary isotachophoresis (cITP) is a technique in which the analytes move through the capillary at a constant speed but are nevertheless separated by their respective mobilities. Capillary zone electrophoresis (CZE), also known as free-solution CE (FSCE), is based on differences in the electrophoretic mobility of the species, determined by the charge on the molecule, and the frictional resistance the molecule encounters during migration which is often directly proportional to the size of the molecule. Capillary isoelectric focusing (CIEF) allows weakly-ionizable amphoteric molecules, to be separated by electrophoresis in a pH gradient. CEC is a hybrid technique between traditional high performance liquid chromatography (HPLC) and CE.

Separation and purification techniques used in the present invention include any chromatography procedures known in the art. Chromatography can be based on the differential adsorption and elution of certain analytes or partitioning of analytes between mobile and stationary phases. Different examples of chromatography include, but not limited to, liquid chromatography (LC), gas chromatography (GC), high performance liquid chromatography (HPLC), etc.

IV. Biomarker Nucleic Acids and Polypeptides

One aspect of the present invention pertains to the use of isolated nucleic acid molecules that correspond to biomarker nucleic acids that encode a biomarker polypeptide or a portion of such a polypeptide. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule is one which is separated from other nucleic acid molecules which are present in the natural source of the nucleic acid molecule. Preferably, an "isolated" nucleic acid molecule is free of sequences (preferably protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, 4 kB, 3 kB, 2 kB, 1 kB, 0.5 kB or 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

A biomarker nucleic acid molecule of the present invention can be isolated using standard molecular biology techniques and the sequence information in the database records described herein. Using all or a portion of such nucleic acid sequences, nucleic acid molecules of the present invention can be isolated using standard hybridization and cloning techniques (e.g., as described in Sambrook et al., ed., *Molecular Cloning: A Laboratory Manual,* 2nd ed., Cold Spring Harbor Laboratory Press, Cold Spring Harbor, N.Y., 1989).

A nucleic acid molecule of the present invention can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule of the present invention can be prepared by standard synthetic techniques, e.g., using an automated DNA synthesizer.

Moreover, a nucleic acid molecule of the present invention can comprise only a portion of a nucleic acid sequence, wherein the full length nucleic acid sequence comprises a marker of the present invention or which encodes a polypeptide corresponding to a marker of the present invention. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, preferably about 15, more preferably about 25, 50, 75, 100, 125, 150, 175, 200, 250, 300, 350, or 400 or more consecutive nucleotides of a biomarker nucleic acid sequence. Probes based on the sequence of a biomarker nucleic acid molecule can be used to detect transcripts or genomic sequences corresponding to one or more markers of the present invention. The probe comprises a label group attached thereto, e.g., a radioisotope, a fluorescent compound, an enzyme, or an enzyme co-factor.

A biomarker nucleic acid molecules that differ, due to degeneracy of the genetic code, from the nucleotide sequence of nucleic acid molecules encoding a protein which corresponds to the biomarker, and thus encode the same protein, are also contemplated.

In addition, it will be appreciated by those skilled in the art that DNA sequence polymorphisms that lead to changes in the amino acid sequence can exist within a population (e.g., the human population). Such genetic polymorphisms can exist among individuals within a population due to natural allelic variation. An allele is one of a group of genes which occur alternatively at a given genetic locus. In addition, it will be appreciated that DNA polymorphisms that affect RNA expression levels can also exist that may affect the overall expression level of that gene (e.g., by affecting regulation or degradation).

The term "allele," which is used interchangeably herein with "allelic variant," refers to alternative forms of a gene or portions thereof. Alleles occupy the same locus or position on homologous chromosomes. When a subject has two identical alleles of a gene, the subject is said to be homozygous for the gene or allele. When a subject has two different alleles of a gene, the subject is said to be heterozygous for the gene or allele. For example, biomarker alleles can differ from each other in a single nucleotide, or several nucleotides, and can include substitutions, deletions, and insertions of nucleotides. An allele of a gene can also be a form of a gene containing one or more mutations.

The term "allelic variant of a polymorphic region of gene" or "allelic variant", used interchangeably herein, refers to an alternative form of a gene having one of several possible nucleotide sequences found in that region of the gene in the population. As used herein, allelic variant is meant to encompass functional allelic variants, non-functional allelic variants, SNPs, mutations and polymorphisms.

The term "single nucleotide polymorphism" (SNP) refers to a polymorphic site occupied by a single nucleotide, which is the site of variation between allelic sequences. The site is usually preceded by and followed by highly conserved sequences of the allele (e.g., sequences that vary in less than 1/100 or 1/1000 members of a population). A SNP usually arises due to substitution of one nucleotide for another at the polymorphic site. SNPs can also arise from a deletion of a nucleotide or an insertion of a nucleotide relative to a reference allele. Typically the polymorphic site is occupied by a base other than the reference base. For example, where the reference allele contains the base "T" (thymidine) at the polymorphic site, the altered allele can contain a "C" (cytidine), "G" (guanine), or "A" (adenine) at the polymorphic site. SNP's may occur in protein-coding nucleic acid sequences, in which case they may give rise to a defective or otherwise variant protein, or genetic disease. Such a SNP may alter the coding sequence of the gene and therefore specify another amino acid (a "missense" SNP) or a SNP may introduce a stop codon (a "nonsense" SNP). When a SNP does not alter the amino acid sequence of a protein, the SNP is called "silent." SNP's may also occur in noncoding regions of the nucleotide sequence. This may result in defective protein expression, e.g., as a result of alternative spicing, or it may have no effect on the function of the protein.

As used herein, the terms "gene" and "recombinant gene" refer to nucleic acid molecules comprising an open reading frame encoding a polypeptide corresponding to a marker of the present invention. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the present invention.

In another embodiment, a biomarker nucleic acid molecule is at least 7, 15, 20, 25, 30, 40, 60, 80, 100, 150, 200, 250, 300, 350, 400, 450, 550, 650, 700, 800, 900, 1000, 1100, 1200, 1300, 1400, 1500, 1600, 1700, 1800, 1900, 2000, 2200, 2400, 2600, 2800, 3000, 3500, 4000, 4500, or more nucleotides in length and hybridizes under stringent conditions to a nucleic acid molecule corresponding to a marker of the present invention or to a nucleic acid molecule encoding a protein corresponding to a marker of the present invention. As used herein, the term "hybridizes under stringent conditions" is intended to describe conditions for hybridization and washing under which nucleotide sequences at least 60% (65%, 70%, 75%, 80%, preferably 85%) identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). A preferred, non-limiting example of stringent hybridization conditions are hybridization in 6× sodium chloride/sodium citrate (SSC) at about 45° C., followed by one or more washes in 0.2×SSC, 0.1% SDS at 50-65° C.

In addition to naturally-occurring allelic variants of a nucleic acid molecule of the present invention that can exist in the population, the skilled artisan will further appreciate that sequence changes can be introduced by mutation thereby leading to changes in the amino acid sequence of the encoded protein, without altering the biological activity of the protein encoded thereby. For example, one can make nucleotide substitutions leading to amino acid substitutions at "non-essential" amino acid residues. A "non-essential" amino acid residue is a residue that can be altered from the wild-type sequence without altering the biological activity, whereas an "essential" amino acid residue is required for biological activity. For example, amino acid residues that are not conserved or only semi-conserved among homologs of various species may be non-essential for activity and thus would be likely targets for alteration. Alternatively, amino acid residues that are conserved among the homologs of various species (e.g., murine and human) may be essential for activity and thus would not be likely targets for alteration.

Accordingly, another aspect of the present invention pertains to nucleic acid molecules encoding a polypeptide of the present invention that contain changes in amino acid residues that are not essential for activity. Such polypeptides differ in amino acid sequence from the naturally-occurring proteins which correspond to the markers of the present invention, yet retain biological activity. In one embodiment, a biomarker protein has an amino acid sequence that is at least about 40% identical, 50%, 60%, 70%, 75%, 80%, 83%, 85%, 87.5%, 90%, 91%, 92%, 93%, 94%, 95%, 96%, 97%, 98%, 99% or identical to the amino acid sequence of a biomarker protein described herein.

An isolated nucleic acid molecule encoding a variant protein can be created by introducing one or more nucleotide substitutions, additions or deletions into the nucleotide sequence of nucleic acids of the present invention, such that one or more amino acid residue substitutions, additions, or deletions are introduced into the encoded protein. Mutations can be introduced by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), non-polar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed recombinantly and the activity of the protein can be determined.

In some embodiments, the present invention further contemplates the use of anti-biomarker antisense nucleic acid molecules, i.e., molecules which are complementary to a sense nucleic acid of the present invention, e.g., complementary to the coding strand of a double-stranded cDNA molecule corresponding to a marker of the present invention or complementary to an mRNA sequence corresponding to a marker of the present invention. Accordingly, an antisense nucleic acid molecule of the present invention can hydrogen bond to (i.e. anneal with) a sense nucleic acid of the present invention. The antisense nucleic acid can be complementary to an entire coding strand, or to only a portion thereof, e.g., all or part of the protein coding region (or open reading frame). An antisense nucleic acid molecule can also be antisense to all or part of a non-coding region of the coding strand of a nucleotide sequence encoding a polypeptide of the present invention. The non-coding regions ("5' and 3' untranslated regions") are the 5' and 3' sequences which flank the coding region and are not translated into amino acids.

An antisense oligonucleotide can be, for example, about 5, 10, 15, 20, 25, 30, 35, 40, 45, or 50 or more nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been sub-cloned in an antisense orientation (i.e., RNA transcribed from the inserted nucleic acid will be of an antisense orientation to a target nucleic acid of interest, described further in the following subsection).

The antisense nucleic acid molecules of the present invention are typically administered to a subject or generated in situ such that they hybridize with or bind to cellular mRNA and/or genomic DNA encoding a polypeptide corresponding to a selected marker of the present invention to thereby inhibit expression of the marker, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. Examples of a route of administration of antisense nucleic acid molecules of the present invention includes direct injection at a tissue site or infusion of the antisense nucleic acid into a blood- or bone marrow-associated body fluid. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

An antisense nucleic acid molecule of the present invention can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, *Nucleic Acids Res.* 15:6625-6641). The antisense nucleic acid molecule can also comprise a 2'-o-methylribonucleotide (Inoue et al., 1987, *Nucleic Acids Res.* 15:6131-6148) or a chimeric RNA-DNA analogue (Inoue et al., 1987, *FEBS Lett.* 215:327-330).

The present invention also encompasses ribozymes. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes as described in Haselhoff and Gerlach, 1988, *Nature* 334:585-591) can be used to catalytically cleave mRNA transcripts to thereby inhibit translation of the protein encoded by the mRNA. A ribozyme having specificity for a nucleic acid molecule encoding a polypeptide corresponding to a marker of the present invention can be designed based upon the nucleotide sequence of a cDNA corresponding to the marker. For example, a derivative of a Tetrahymena L-19 IVS RNA can be constructed in which the nucleotide sequence of the active site is complementary to the nucleotide sequence to be cleaved (see Cech et al. U.S. Pat. No. 4,987,071; and Cech et al. U.S. Pat. No. 5,116,742). Alternatively, an mRNA encoding a polypeptide of the present invention can be used to select a catalytic RNA having a specific ribonuclease activity from a pool of RNA molecules (see, e.g., Bartel and Szostak, 1993, *Science* 261:1411-1418).

The present invention also encompasses nucleic acid molecules which form triple helical structures. For example, expression of a biomarker protein can be inhibited by targeting nucleotide sequences complementary to the regulatory region of the gene encoding the polypeptide (e.g., the promoter and/or enhancer) to form triple helical structures that prevent transcription of the gene in target cells. See generally Helene (1991) *Anticancer Drug Des.* 6(6):569-84; Helene (1992) *Ann. N.Y. Acad. Sci.* 660:27-36; and Maher (1992) *Bioassays* 14(12):807-15.

In various embodiments, the nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acid molecules (see Hyrup et al., 1996, *Bioorganic & Medicinal Chemistry* 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al. (1996), supra; Perry-O'Keefe et al. (1996) *Proc. Natl. Acad. Sci. USA* 93:14670-675.

PNAs can be used in therapeutic and diagnostic applications. For example, PNAs can be used as antisense or antigene agents for sequence-specific modulation of gene expression by, e.g., inducing transcription or translation arrest or inhibiting replication. PNAs can also be used, e.g., in the analysis of single base pair mutations in a gene by, e.g., PNA directed PCR clamping; as artificial restriction enzymes when used in combination with other enzymes, e.g., S1 nucleases (Hyrup (1996), supra; or as probes or primers for DNA sequence and hybridization (Hyrup, 1996, supra; Perry-O'Keefe et al., 1996, *Proc. Natl. Acad. Sci. USA* 93:14670-675).

In another embodiment, PNAs can be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which can combine the advantageous properties of PNA and DNA. Such chimeras allow DNA recognition enzymes, e.g., RNASE H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup (1996), supra, and Finn et al. (1996) *Nucleic Acids Res.* 24(17):3357-63. For example, a DNA chain can be synthesized on a solid support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, *Nucleic Acids Res.* 17:5973-88). PNA monomers are then coupled in a step-wise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, *Bioorganic Med. Chem. Lett.* 5:1119-11124).

In other embodiments, the oligonucleotide can include other appended groups such as peptides (e.g., for targeting host cell receptors in vivo), or agents facilitating transport across the cell membrane (see, e.g., Letsinger et al., 1989, *Proc. Natl. Acad. Sci. USA* 86:6553-6556; Lemaitre et al., 1987, *Proc. Natl. Acad. Sci. USA* 84:648-652; PCT Publication No. WO 88/09810) or the blood-brain barrier (see, e.g., PCT Publication No. WO 89/10134). In addition, oligonucleotides can be modified with hybridization-triggered cleavage agents (see, e.g., Krol et al., 1988, *Bio/Techniques* 6:958-976) or intercalating agents (see, e.g., Zon, 1988, *Pharm. Res.* 5:539-549). To this end, the oligonucleotide can be conjugated to another molecule, e.g., a peptide, hybridization triggered cross-linking agent, transport agent, hybridization-triggered cleavage agent, etc.

Another aspect of the present invention pertains to the use of biomarker proteins and biologically active portions thereof. In one embodiment, the native polypeptide corresponding to a marker can be isolated from cells or tissue sources by an appropriate purification scheme using standard protein purification techniques. In another embodiment, polypeptides corresponding to a marker of the present invention are produced by recombinant DNA techniques. Alternative to recombinant expression, a polypeptide corresponding to a marker of the present invention can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, 20%, 10%, or 5% (by dry weight) of heterologous protein (also referred to herein as a "contaminating protein"). When the protein or biologically active portion thereof is recombinantly produced, it is also preferably substantially free of culture medium, i.e., culture medium represents less than about 20%, 10%, or 5% of the volume of the protein preparation. When the protein is produced by chemical synthesis, it is preferably substantially free of chemical precursors or other chemicals, i.e., it is separated from chemical precursors or other chemicals which are involved in the synthesis of the protein. Accordingly such preparations of the protein have less than about 30%, 20%, 10%, 5% (by dry weight) of chemical precursors or compounds other than the polypeptide of interest.

Biologically active portions of a biomarker polypeptide include polypeptides comprising amino acid sequences sufficiently identical to or derived from a biomarker protein amino acid sequence described herein, but which includes fewer amino acids than the full length protein, and exhibit at least one activity of the corresponding full-length protein. Typically, biologically active portions comprise a domain or motif with at least one activity of the corresponding protein. A biologically active portion of a protein of the present invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide of the present invention.

Preferred polypeptides have an amino acid sequence of a biomarker protein encoded by a nucleic acid molecule described herein. Other useful proteins are substantially identical (e.g., at least about 40%, preferably 50%, 60%, 70%, 75%, 80%, 83%, 85%, 88%, 90%, 91%, 92%, 93%, 94%, 95%, 96%, 97%, 98%, or 99%) to one of these sequences and retain the functional activity of the protein of the corresponding naturally-occurring protein yet differ in amino acid sequence due to natural allelic variation or mutagenesis.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. A preferred, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J Mol. Biol.* 215:403-410. BLAST nucleotide searches can be performed with the NBLAST program, score=100, wordlength=12 to obtain nucleotide sequences homologous to a nucleic acid molecules of the present invention. BLAST protein searches can be performed with the XBLAST program, score=50, wordlength=3 to obtain amino acid sequences homologous to a protein molecules of the present invention. To obtain gapped alignments for comparison purposes, Gapped BLAST can be utilized as described in Altschul et al. (1997) Nucleic Acids Res. 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another preferred, non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

The present invention also provides chimeric or fusion proteins corresponding to a biomarker protein. As used herein, a "chimeric protein" or "fusion protein" comprises all or part (preferably a biologically active part) of a polypeptide corresponding to a marker of the present invention operably linked to a heterologous polypeptide (i.e., a polypeptide other than the polypeptide corresponding to the marker). Within the fusion protein, the term "operably linked" is intended to indicate that the polypeptide of the present invention and the heterologous polypeptide are fused in-frame to each other. The heterologous polypeptide can be fused to the amino-terminus or the carboxyl-terminus of the polypeptide of the present invention.

One useful fusion protein is a GST fusion protein in which a polypeptide corresponding to a marker of the present invention is fused to the carboxyl terminus of GST sequences. Such fusion proteins can facilitate the purification of a recombinant polypeptide of the present invention.

In another embodiment, the fusion protein contains a heterologous signal sequence, immunoglobulin fusion protein, toxin, or other useful protein sequence. Chimeric and fusion proteins of the present invention can be produced by standard recombinant DNA techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see, e.g., Ausubel et al., supra). Moreover, many expression vectors are commercially available that already encode a fusion moiety (e.g., a GST polypeptide). A nucleic acid encoding a polypeptide of the present invention can be cloned into such an expression vector such that the fusion moiety is linked in-frame to the polypeptide of the present invention.

A signal sequence can be used to facilitate secretion and isolation of the secreted protein or other proteins of interest. Signal sequences are typically characterized by a core of hydrophobic amino acids which are generally cleaved from the mature protein during secretion in one or more cleavage events. Such signal peptides contain processing sites that allow cleavage of the signal sequence from the mature proteins as they pass through the secretory pathway. Thus, the present invention pertains to the described polypeptides having a signal sequence, as well as to polypeptides from which the signal sequence has been proteolytically cleaved (i.e., the cleavage products). In one embodiment, a nucleic acid sequence encoding a signal sequence can be operably linked in an expression vector to a protein of interest, such as a protein which is ordinarily not secreted or is otherwise difficult to isolate. The signal sequence directs secretion of the protein, such as from a eukaryotic host into which the expression vector is transformed, and the signal sequence is subsequently or concurrently cleaved. The protein can then be readily purified from the extracellular medium by art recognized methods. Alternatively, the signal sequence can be linked to the protein of interest using a sequence which facilitates purification, such as with a GST domain.

The present invention also pertains to variants of the biomarker polypeptides described herein. Such variants have an altered amino acid sequence which can function as either agonists (mimetics) or as antagonists. Variants can be generated by mutagenesis, e.g., discrete point mutation or truncation. An agonist can retain substantially the same, or a subset, of the biological activities of the naturally occurring form of the protein. An antagonist of a protein can inhibit one or more of the activities of the naturally occurring form of the protein by, for example, competitively binding to a downstream or upstream member of a cellular signaling cascade which includes the protein of interest. Thus, specific biological effects can be elicited by treatment with a variant of limited function. Treatment of a subject with a variant having a subset of the biological activities of the naturally occurring form of the protein can have fewer side effects in a subject relative to treatment with the naturally occurring form of the protein.

Variants of a biomarker protein which function as either agonists (mimetics) or as antagonists can be identified by screening combinatorial libraries of mutants, e.g., truncation mutants, of the protein of the present invention for agonist or antagonist activity. In one embodiment, a variegated library of variants is generated by combinatorial mutagenesis at the nucleic acid level and is encoded by a variegated gene library. A variegated library of variants can be produced by, for example, enzymatically ligating a mixture of synthetic oligonucleotides into gene sequences such that a degenerate set of potential protein sequences is expressible as individual polypeptides, or alternatively, as a set of larger fusion proteins (e.g., for phage display). There are a variety of methods which can be used to produce libraries of potential variants of the polypeptides of the present invention from a degenerate oligonucleotide sequence. Methods for synthesizing degenerate oligonucleotides are known in the art (see, e.g., Narang, 1983, *Tetrahedron* 39:3; Itakura et al., 1984, *Annu. Rev. Biochem.* 53:323; Itakura et al., 1984, *Science* 198:1056; Ike et al., 1983 *Nucleic Acid Res.* 11:477).

In addition, libraries of fragments of the coding sequence of a polypeptide corresponding to a marker of the present invention can be used to generate a variegated population of polypeptides for screening and subsequent selection of variants. For example, a library of coding sequence fragments can be generated by treating a double stranded PCR fragment of the coding sequence of interest with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes amino terminal and internal fragments of various sizes of the protein of interest.

Several techniques are known in the art for screening gene products of combinatorial libraries made by point mutations or truncation, and for screening cDNA libraries for gene products having a selected property. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a technique which enhances the frequency of functional mutants in the libraries, can be used in combination with the screening assays to identify variants of a protein of the present invention (Arkin and Yourvan, 1992, *Proc. Natl. Acad. Sci. USA* 89:7811-7815; Delgrave et al., 1993, *Protein Engineering* 6(3):327-331).

The production and use of biomarker nucleic acid and/or biomarker polypeptide molecules described herein can be facilitated by using standard recombinant techniques. In some embodiments, such techniques use vectors, preferably expression vectors, containing a nucleic acid encoding a biomarker polypeptide or a portion of such a polypeptide. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors, namely expression vectors, are capable of directing the expression of genes to which they are operably linked. In general, expression vectors of utility in recombinant DNA techniques are often in the form of plasmids (vectors). However, the present invention is intended to include such other forms of expression vectors, such as viral vectors (e.g., replication defective retroviruses, adenoviruses and adeno-associated viruses), which serve equivalent functions.

The recombinant expression vectors of the present invention comprise a nucleic acid of the present invention in a form suitable for expression of the nucleic acid in a host cell. This means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, *Methods in Enzymology: Gene Expression Technology* vol. 185, Academic Press, San Diego, Calif. (1991). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the present invention can be introduced into host cells to thereby produce proteins or peptides, including fusion proteins or peptides, encoded by nucleic acids as described herein.

The recombinant expression vectors for use in the present invention can be designed for expression of a polypeptide corresponding to a marker of the present invention in prokaryotic (e.g., *E. coli*) or eukaryotic cells (e.g., insect cells {using baculovirus expression vectors}, yeast cells or mammalian cells). Suitable host cells are discussed further in Goeddel, supra. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988, *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Examples of suitable inducible non-fusion *E. coli* expression vectors include pTrc (Amann et al., 1988, *Gene* 69:301-315) and pET 11d (Studier et al., p. 60-89, In *Gene Expression Technology: Methods in Enzymology* vol. 185, Academic Press, San Diego, Calif., 1991). Target biomarker nucleic acid expression from the pTrc vector relies on host RNA polymerase transcription from a hybrid trp-lac fusion promoter. Target biomarker nucleic acid expression from the pET 11d vector relies on transcription from a T7 gn10-lac fusion promoter mediated by a co-expressed viral RNA polymerase (T7 gn1). This viral polymerase is supplied by host strains BL21 (DE3) or HMS174(DE3) from a resident prophage harboring a T7 gn1 gene under the transcriptional control of the lacUV 5 promoter.

One strategy to maximize recombinant protein expression in *E. coli* is to express the protein in a host bacterium with an impaired capacity to proteolytically cleave the recombinant protein (Gottesman, p. 119-128, In *Gene Expression Technology: Methods in Enzymology* vol. 185, Academic Press, San Diego, Calif., 1990. Another strategy is to alter the nucleic acid sequence of the nucleic acid to be inserted into an expression vector so that the individual codons for each amino acid are those preferentially utilized in *E. coli* (Wada et al., 1992, *Nucleic Acids Res.* 20:2111-2118). Such alteration of nucleic acid sequences of the present invention can be carried out by standard DNA synthesis techniques.

In another embodiment, the expression vector is a yeast expression vector. Examples of vectors for expression in yeast *S. cerevisiae* include pYepSecl (Baldari et al., 1987, *EMBO J.* 6:229-234), pMFa (Kurjan and Herskowitz, 1982, *Cell* 30:933-943), pJRY88 (Schultz et al., 1987, *Gene* 54:113-123), pYES2 (Invitrogen Corporation, San Diego, Calif.), and pPicZ (Invitrogen Corp, San Diego, Calif.).

Alternatively, the expression vector is a baculovirus expression vector. Baculovirus vectors available for expression of proteins in cultured insect cells (e.g., Sf 9 cells) include the pAc series (Smith et al., 1983, *Mol. Cell Biol.* 3:2156-2165) and the pVL series (Lucklow and Summers, 1989, *Virology* 170:31-39).

In yet another embodiment, a nucleic acid of the present invention is expressed in mammalian cells using a mammalian expression vector. Examples of mammalian expression vectors include pCDM8 (Seed, 1987, *Nature* 329:840) and pMT2PC (Kaufman et al., 1987, *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook et al., supra.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al., 1987, *Genes Dev.* 1:268-277), lymphoid-specific promoters (Calame and Eaton, 1988, *Adv. Immunol.* 43:235-275), in particular promoters of T cell receptors (Winoto and Baltimore, 1989, *EMBO J.* 8:729-733) and immunoglobulins (Banerji et al., 1983, *Cell* 33:729-740; Queen and Baltimore, 1983, *Cell* 33:741-748), neuron-specific promoters (e.g., the neurofilament promoter; Byrne and Ruddle, 1989, *Proc. Natl. Acad. Sci. USA* 86:5473-5477), pancreas-specific promoters (Edlund et al., 1985, *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss, 1990, *Science* 249:374-379) and the α-fetoprotein promoter (Camper and Tilghman, 1989, *Genes Dev.* 3:537-546).

The present invention further provides a recombinant expression vector comprising a DNA molecule cloned into the expression vector in an antisense orientation. That is, the DNA molecule is operably linked to a regulatory sequence in a manner which allows for expression (by transcription of the DNA molecule) of an RNA molecule which is antisense to the mRNA encoding a polypeptide of the present invention. Regulatory sequences operably linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue-specific or cell type specific expression of antisense RNA. The antisense expression vector can be in the form of a recombinant plasmid, phagemid, or attenuated virus in which antisense nucleic acids are produced under the control of a high efficiency regulatory region, the activity of which can be determined by the cell type into which the vector is introduced. For a discussion of the regulation of gene expression using antisense genes (see Weintraub et al., 1986, *Trends in Genetics*, Vol. 1(1)).

Another aspect of the present invention pertains to host cells into which a recombinant expression vector of the present invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic (e.g., *E. coli*) or eukaryotic cell (e.g., insect cells, yeast or mammalian cells).

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid into a host cell, including calcium phosphate or calcium chloride co-precipitation, DEAE-dextran-mediated transfection, lipofection, or electroporation. Suitable methods for transforming or transfecting host cells can be found in Sambrook, et al. (supra), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those which confer resistance to drugs, such as G418, hygromycin and methotrexate. Cells stably transfected with the introduced nucleic acid can be identified by drug selection (e.g., cells that have incorporated the selectable marker gene will survive, while the other cells die).

V. Analyzing Biomarker Nucleic Acids and Polypeptides

Biomarker nucleic acids and/or biomarker polypeptides can be analyzed according to the methods described herein and techniques known to the skilled artisan to identify such genetic or expression alterations useful for the present invention including, but not limited to, 1) an alteration in the level of a biomarker transcript or polypeptide, 2) a deletion or addition of one or more nucleotides from a biomarker gene, 4) a substitution of one or more nucleotides of a biomarker gene, 5) aberrant modification of a biomarker gene, such as an expression regulatory region, and the like.

a. Methods for Detection of Copy Number

Methods of evaluating the copy number of a biomarker nucleic acid are well known to those of skill in the art. The presence or absence of chromosomal gain or loss can be evaluated simply by a determination of copy number of the regions or markers identified herein.

In one embodiment, a biological sample is tested for the presence of copy number changes in genomic loci containing the genomic marker. A copy number of at least 3, 4, 5, 6, 7, 8, 9, or 10 is predictive of poorer outcome of PD-1 pathway inhibitor treatment.

Methods of evaluating the copy number of a biomarker locus include, but are not limited to, hybridization-based assays. Hybridization-based assays include, but are not limited to, traditional "direct probe" methods, such as Southern blots, in situ hybridization (e.g., FISH and FISH plus SKY) methods, and "comparative probe" methods, such as comparative genomic hybridization (CGH), e.g., cDNA-based or oligonucleotide-based CGH. The methods can be used in a wide variety of formats including, but not limited to, substrate (e.g. membrane or glass) bound methods or array-based approaches.

In one embodiment, evaluating the biomarker gene copy number in a sample involves a Southern Blot. In a Southern Blot, the genomic DNA (typically fragmented and separated on an electrophoretic gel) is hybridized to a probe specific for the target region. Comparison of the intensity of the hybridization signal from the probe for the target region with control probe signal from analysis of normal genomic DNA (e.g., a non-amplified portion of the same or related cell, tissue, organ, etc.) provides an estimate of the relative copy number of the target nucleic acid. Alternatively, a Northern blot may be utilized for evaluating the copy number of encoding nucleic acid in a sample. In a Northern blot, mRNA is hybridized to a probe specific for the target region. Comparison of the intensity of the hybridization signal from the probe for the target region with control probe signal from analysis of normal RNA (e.g., a non-amplified portion of the same or related cell, tissue, organ, etc.) provides an estimate of the relative copy number of the target nucleic acid. Alternatively, other methods well known in the art to detect RNA can be used, such that higher or lower expression relative to an appropriate control (e.g., a non-amplified portion of the same or related cell tissue, organ, etc.) provides an estimate of the relative copy number of the target nucleic acid.

An alternative means for determining genomic copy number is in situ hybridization (e.g., Angerer (1987) *Meth. Enzymol* 152: 649). Generally, in situ hybridization comprises the following steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments. The reagent used in each of these steps and the conditions for use vary depending on the particular application. In a typical in situ hybridization assay, cells are fixed to a solid support, typically a glass slide. If a nucleic acid is to be probed, the cells are typically denatured with heat or alkali. The cells are then contacted with a hybridization solution at a moderate temperature to permit annealing of labeled probes specific to the nucleic acid sequence encoding the protein. The targets (e.g., cells) are then typically washed at a predetermined stringency or at an increasing stringency until an appropriate signal to noise ratio is obtained. The probes are typically labeled, e.g., with radio-isotopes or fluorescent reporters. In one embodiment, probes are sufficiently long so as to specifically hybridize with the target nucleic acid(s) under stringent conditions. Probes generally range in length from about 200 bases to about 1000 bases. In some applications it is necessary to block the hybridization capacity of repetitive sequences. Thus, in some embodiments, tRNA, human genomic DNA, or Cot-I DNA is used to block non-specific hybridization.

An alternative means for determining genomic copy number is comparative genomic hybridization. In general, genomic DNA is isolated from normal reference cells, as well as from test cells (e.g., tumor cells) and amplified, if necessary. The two nucleic acids are differentially labeled and then hybridized in situ to metaphase chromosomes of a reference cell. The repetitive sequences in both the reference and test DNAs are either removed or their hybridization capacity is reduced by some means, for example by prehybridization with appropriate blocking nucleic acids and/or including such blocking nucleic acid sequences for said repetitive sequences during said hybridization. The bound, labeled DNA sequences are then rendered in a visualizable form, if necessary. Chromosomal regions in the test cells which are at increased or decreased copy number can be identified by detecting regions where the ratio of signal from the two DNAs is altered. For example, those regions that have decreased in copy number in the test cells will show relatively lower signal from the test DNA than the reference compared to other regions of the genome. Regions that have been increased in copy number in the test cells will show relatively higher signal from the test DNA. Where there are chromosomal deletions or multiplications, differences in the ratio of the signals from the two labels will be detected and the ratio will provide a measure of the copy number. In another embodiment of CGH, array CGH (aCGH), the immobilized chromosome element is replaced with a collection of solid support bound target nucleic acids on an array, allowing for a large or complete percentage of the genome to be represented in the collection of solid support bound targets. Target nucleic acids may comprise cDNAs, genomic DNAs, oligonucleotides (e.g., to detect single nucleotide polymorphisms) and the like. Array-based CGH may also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Methods of preparing immobilized chromosomes or arrays and performing comparative genomic hybridization are well known in the art (see, e.g., U.S. Pat. Nos. 6,335,167; 6,197,501; 5,830,645; and 5,665,549 and Albertson (1984) *EMBO J.* 3: 1227-1234; Pinkel (1988) *Proc. Natl. Acad. Sci. USA* 85: 9138-9142; EPO Pub. No. 430,402; Methods in Molecular Biology, Vol. 33: In situ Hybridization Protocols, Choo, ed., Humana Press, Totowa, N.J. (1994), etc.) In another embodiment, the hybridization protocol of Pinkel, et al. (1998) *Nature Genetics* 20: 207-211, or of Kallioniemi (1992) *Proc. Natl Acad Sci USA* 89:5321-5325 (1992) is used.

In still another embodiment, amplification-based assays can be used to measure copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g. healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the present invention. In fluorogenic quantitative PCR, quantitation is based on amount of fluorescence signals, e.g., TaqMan and SYBR green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Loss of heterozygosity (LOH) and major copy proportion (MCP) mapping (Wang, Z. C., et al. (2004) *Cancer Res* 64(1):64-71; Seymour, A. B., et al. (1994) *Cancer Res* 54, 2761-4; Hahn, S. A., et al. (1995) *Cancer Res* 55, 4670-5; Kimura, M., et al. (1996) *Genes Chromosomes Cancer* 17, 88-93; Li et al., (2008) *MBC Bioinform.* 9, 204-219) may also be used to identify regions of amplification or deletion.

b. Methods for Detection of Biomarker Nucleic Acid Expression

Biomarker expression may be assessed by any of a wide variety of well known methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In preferred embodiments, activity of a particular gene is characterized by a measure of gene transcript (e.g. mRNA), by a measure of the quantity of translated protein, or by a measure of gene product activity. Marker expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

In another embodiment, detecting or determining expression levels of a biomarker and functionally similar homologs thereof, including a fragment or genetic alteration thereof (e.g., in regulatory or promoter regions thereof) comprises detecting or determining RNA levels for the marker of interest. In one embodiment, one or more cells from the subject to be tested are obtained and RNA is isolated from the cells. In a preferred embodiment, a sample of breast tissue cells is obtained from the subject.

In one embodiment, RNA is obtained from a single cell. For example, a cell can be isolated from a tissue sample by laser capture microdissection (LCM). Using this technique, a cell can be isolated from a tissue section, including a stained tissue section, thereby assuring that the desired cell is isolated (see, e.g., Bonner et al. (1997) Science 278: 1481; Emmert-Buck et al. (1996) Science 274:998; Fend et al. (1999) Am. J. Path. 154: 61 and Murakami et al. (2000) Kidney Int. 58:1346). For example, Murakami et al., supra, describe isolation of a cell from a previously immunostained tissue section.

It is also be possible to obtain cells from a subject and culture the cells in vitro, such as to obtain a larger population of cells from which RNA can be extracted. Methods for establishing cultures of non-transformed cells, i.e., primary cell cultures, are known in the art.

When isolating RNA from tissue samples or cells from individuals, it may be important to prevent any further changes in gene expression after the tissue or cells has been removed from the subject. Changes in expression levels are known to change rapidly following perturbations, e.g., heat shock or activation with lipopolysaccharide (LPS) or other reagents. In addition, the RNA in the tissue and cells may quickly become degraded. Accordingly, in a preferred embodiment, the tissue or cells obtained from a subject is snap frozen as soon as possible.

RNA can be extracted from the tissue sample by a variety of methods, e.g., the guanidium thiocyanate lysis followed by CsCl centrifugation (Chirgwin et al., 1979, Biochemistry 18:5294-5299). RNA from single cells can be obtained as described in methods for preparing cDNA libraries from single cells, such as those described in Dulac, C. (1998) Curr. Top. Dev. Biol. 36, 245 and Jena et al. (1996) J. Immunol. Methods 190:199. Care to avoid RNA degradation must be taken, e.g., by inclusion of RNAsin.

The RNA sample can then be enriched in particular species. In one embodiment, poly(A)+RNA is isolated from the RNA sample. In general, such purification takes advantage of the poly-A tails on mRNA. In particular and as noted above, poly-T oligonucleotides may be immobilized within on a solid support to serve as affinity ligands for mRNA. Kits for this purpose are commercially available, e.g., the MessageMaker kit (Life Technologies, Grand Island, N.Y.).

In a preferred embodiment, the RNA population is enriched in marker sequences. Enrichment can be undertaken, e.g., by primer-specific cDNA synthesis, or multiple rounds of linear amplification based on cDNA synthesis and template-directed in vitro transcription (see, e.g., Wang et al. (1989) PNAS 86, 9717; Dulac et al., supra, and Jena et al., supra).

The population of RNA, enriched or not in particular species or sequences, can further be amplified. As defined herein, an "amplification process" is designed to strengthen, increase, or augment a molecule within the RNA. For example, where RNA is mRNA, an amplification process such as RT-PCR can be utilized to amplify the mRNA, such that a signal is detectable or detection is enhanced. Such an amplification process is beneficial particularly when the biological, tissue, or tumor sample is of a small size or volume.

Various amplification and detection methods can be used. For example, it is within the scope of the present invention to reverse transcribe mRNA into cDNA followed by polymerase chain reaction (RT-PCR); or, to use a single enzyme for both steps as described in U.S. Pat. No. 5,322,770, or reverse transcribe mRNA into cDNA followed by symmetric gap ligase chain reaction (RT-AGLCR) as described by R. L. Marshall, et al., PCR Methods and Applications 4: 80-84 (1994). Real time PCR may also be used.

Other known amplification methods which can be utilized herein include but are not limited to the so-called "NASBA" or "3SR" technique described in PNAS USA 87: 1874-1878 (1990) and also described in Nature 350 (No. 6313): 91-92 (1991); Q-beta amplification as described in published European Patent Application (EPA) No. 4544610; strand displacement amplification (as described in G. T. Walker et al., Clin. Chem. 42: 9-13 (1996) and European Patent Application No. 684315; target mediated amplification, as described by PCT Publication WO9322461; PCR; ligase chain reaction (LCR) (see, e.g., Wu and Wallace, Genomics 4, 560 (1989), Landegren et al., Science 241, 1077 (1988)); self-sustained sequence replication (SSR) (see, e.g., Guatelli et al., Proc. Nat. Acad. Sci. USA, 87, 1874 (1990)); and transcription amplification (see, e.g., Kwoh et al., Proc. Natl. Acad. Sci. USA 86, 1173 (1989)).

Many techniques are known in the state of the art for determining absolute and relative levels of gene expression, commonly used techniques suitable for use in the present invention include Northern analysis, RNase protection assays (RPA), microarrays and PCR-based techniques, such as quantitative PCR and differential display PCR. For example, Northern blotting involves running a preparation of RNA on a denaturing agarose gel, and transferring it to a suitable support, such as activated cellulose, nitrocellulose or glass or nylon membranes. Radiolabeled cDNA or RNA is then hybridized to the preparation, washed and analyzed by autoradiography.

In situ hybridization visualization may also be employed, wherein a radioactively labeled antisense RNA probe is hybridized with a thin section of a biopsy sample, washed, cleaved with RNase and exposed to a sensitive emulsion for autoradiography. The samples may be stained with hematoxylin to demonstrate the histological composition of the sample, and dark field imaging with a suitable light filter shows the developed emulsion. Non-radioactive labels such as digoxigenin may also be used.

Alternatively, mRNA expression can be detected on a DNA array, chip or a microarray. Labeled nucleic acids of a test sample obtained from a subject may be hybridized to a solid surface comprising biomarker DNA. Positive hybridization signal is obtained with the sample containing biomarker transcripts. Methods of preparing DNA arrays and their use are well known in the art (see, e.g., U.S. Pat. Nos. 6,618,6796; 6,379,897; 6,664,377; 6,451,536; 548,257; U.S. 20030157485 and Schena et al. (1995) *Science* 20, 467-470; Gerhold et al. (1999) *Trends In Biochem. Sci.* 24, 168-173; and Lennon et al. (2000) *Drug Discovery Today* 5, 59-65, which are herein incorporated by reference in their entirety). Serial Analysis of Gene Expression (SAGE) can also be performed (See for example U.S. Patent Application 20030215858).

To monitor mRNA levels, for example, mRNA is extracted from the biological sample to be tested, reverse transcribed, and fluorescently-labeled cDNA probes are generated. The microarrays capable of hybridizing to marker cDNA are then probed with the labeled cDNA probes, the slides scanned and fluorescence intensity measured. This intensity correlates with the hybridization intensity and expression levels.

Types of probes that can be used in the methods described herein include cDNA, riboprobes, synthetic oligonucleotides and genomic probes. The type of probe used will generally be dictated by the particular situation, such as riboprobes for in situ hybridization, and cDNA for Northern blotting, for example. In one embodiment, the probe is directed to nucleotide regions unique to the RNA. The probes may be as short as is required to differentially recognize marker mRNA transcripts, and may be as short as, for example, 15 bases; however, probes of at least 17, 18, 19 or 20 or more bases can be used. In one embodiment, the primers and probes hybridize specifically under stringent conditions to a DNA fragment having the nucleotide sequence corresponding to the marker. As herein used, the term "stringent conditions" means hybridization will occur only if there is at least 95% identity in nucleotide sequences. In another embodiment, hybridization under "stringent conditions" occurs when there is at least 97% identity between the sequences.

The form of labeling of the probes may be any that is appropriate, such as the use of radioisotopes, for example, $^{32}P$ and $^{35}S$. Labeling with radioisotopes may be achieved, whether the probe is synthesized chemically or biologically, by the use of suitably labeled bases.

In one embodiment, the biological sample contains polypeptide molecules from the test subject. Alternatively, the biological sample can contain mRNA molecules from the test subject or genomic DNA molecules from the test subject.

In another embodiment, the methods further involve obtaining a control biological sample from a control subject, contacting the control sample with a compound or agent capable of detecting marker polypeptide, mRNA, genomic DNA, or fragments thereof, such that the presence of the marker polypeptide, mRNA, genomic DNA, or fragments thereof, is detected in the biological sample, and comparing the presence of the marker polypeptide, mRNA, genomic DNA, or fragments thereof, in the control sample with the presence of the marker polypeptide, mRNA, genomic DNA, or fragments thereof in the test sample.

c. Methods for Detection of Biomarker Protein Expression

The activity or level of a biomarker protein can be detected and/or quantified by detecting or quantifying the expressed polypeptide. The polypeptide can be detected and quantified by any of a number of means well known to those of skill in the art. Aberrant levels of polypeptide expression of the polypeptides encoded by a biomarker nucleic acid and functionally similar homologs thereof, including a fragment or genetic alteration thereof (e.g., in regulatory or promoter regions thereof) are associated with the likelihood of response of a cancer to PD-1 pathway inhibitor therapy. Any method known in the art for detecting polypeptides can be used. Such methods include, but are not limited to, immunodiffusion, immunoelectrophoresis, radioimmunoassay (MA), enzyme-linked immunosorbent assays (ELISAs), immunofluorescent assays, Western blotting, binder-ligand assays, immunohistochemical techniques, agglutination, complement assays, high performance liquid chromatography (HPLC), thin layer chromatography (TLC), hyperdiffusion chromatography, and the like (e.g., Basic and Clinical Immunology, Sites and Terr, eds., Appleton and Lange, Norwalk, Conn. pp 217-262, 1991 which is incorporated by reference). Preferred are binder-ligand immunoassay methods including reacting antibodies with an epitope or epitopes and competitively displacing a labeled polypeptide or derivative thereof.

For example, ELISA and MA procedures may be conducted such that a desired biomarker protein standard is labeled (with a radioisotope such as $^{125}$I or $^{35}$S, or an assayable enzyme, such as horseradish peroxidase or alkaline phosphatase), and, together with the unlabelled sample, brought into contact with the corresponding antibody, whereon a second antibody is used to bind the first, and radioactivity or the immobilized enzyme assayed (competitive assay). Alternatively, the biomarker protein in the sample is allowed to react with the corresponding immobilized antibody, radioisotope- or enzyme-labeled anti-biomarker proteinantibody is allowed to react with the system, and radioactivity or the enzyme assayed (ELISA-sandwich assay). Other conventional methods may also be employed as suitable.

The above techniques may be conducted essentially as a "one-step" or "two-step" assay. A "one-step" assay involves contacting antigen with immobilized antibody and, without washing, contacting the mixture with labeled antibody. A "two-step" assay involves washing before contacting, the mixture with labeled antibody. Other conventional methods may also be employed as suitable.

In one embodiment, a method for measuring biomarker protein levels comprises the steps of: contacting a biological specimen with an antibody or variant (e.g., fragment) thereof which selectively binds the biomarker protein, and detecting whether said antibody or variant thereof is bound to said sample and thereby measuring the levels of the biomarker protein.

Enzymatic and radiolabeling of biomarker protein and/or the antibodies may be effected by conventional means. Such means will generally include covalent linking of the enzyme to the antigen or the antibody in question, such as by glutaraldehyde, specifically so as not to adversely affect the activity of the enzyme, by which is meant that the enzyme must still be capable of interacting with its substrate, although it is not necessary for all of the enzyme to be active, provided that enough remains active to permit the assay to be effected. Indeed, some techniques for binding enzyme are non-specific (such as using formaldehyde), and will only yield a proportion of active enzyme.

It is usually desirable to immobilize one component of the assay system on a support, thereby allowing other components of the system to be brought into contact with the component and readily removed without laborious and time-consuming labor. It is possible for a second phase to be immobilized away from the first, but one phase is usually sufficient.

It is possible to immobilize the enzyme itself on a support, but if solid-phase enzyme is required, then this is generally best achieved by binding to antibody and affixing the antibody to a support, models and systems for which are well-known in the art. Simple polyethylene may provide a suitable support.

Enzymes employable for labeling are not particularly limited, but may be selected from the members of the oxidase group, for example. These catalyze production of hydrogen peroxide by reaction with their substrates, and glucose oxidase is often used for its good stability, ease of availability and cheapness, as well as the ready availability of its substrate (glucose). Activity of the oxidase may be assayed by measuring the concentration of hydrogen peroxide formed after reaction of the enzyme-labeled antibody with the substrate under controlled conditions well-known in the art.

Other techniques may be used to detect biomarker protein according to a practitioner's preference based upon the present disclosure. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Anti-biomarker protein antibodies (unlabeled) are then brought into contact with the support and assayed by a secondary immunological reagent, such as labeled protein A or anti-immunoglobulin (suitable labels including $^{125}$I, horseradish peroxidase and alkaline phosphatase). Chromatographic detection may also be used.

Immunohistochemistry may be used to detect expression of biomarker protein, e.g., in a biopsy sample. A suitable antibody is brought into contact with, for example, a thin layer of cells, washed, and then contacted with a second, labeled antibody. Labeling may be by fluorescent markers, enzymes, such as peroxidase, avidin, or radiolabelling. The assay is scored visually, using microscopy.

Anti-biomarker protein antibodies, such as intrabodies, may also be used for imaging purposes, for example, to detect the presence of biomarker protein in cells and tissues of a subject. Suitable labels include radioisotopes, iodine ($^{125}$I, $^{121}$I) carbon ($^{14}$C), sulphur ($^{35}$S), tritium ($^{3}$H), indium ($^{112}$In), and technetium ($^{99}$mTc), fluorescent labels, such as fluorescein and rhodamine, and biotin.

For in vivo imaging purposes, antibodies are not detectable, as such, from outside the body, and so must be labeled, or otherwise modified, to permit detection. Markers for this purpose may be any that do not substantially interfere with the antibody binding, but which allow external detection. Suitable markers may include those that may be detected by X-radiography, NMR or MRI. For X-radiographic techniques, suitable markers include any radioisotope that emits detectable radiation but that is not overtly harmful to the subject, such as barium or cesium, for example. Suitable markers for NMR and MRI generally include those with a detectable characteristic spin, such as deuterium, which may be incorporated into the antibody by suitable labeling of nutrients for the relevant hybridoma, for example.

The size of the subject, and the imaging system used, will determine the quantity of imaging moiety needed to produce diagnostic images. In the case of a radioisotope moiety, for a human subject, the quantity of radioactivity injected will normally range from about 5 to 20 millicuries of technetium-99. The labeled antibody or antibody fragment will then preferentially accumulate at the location of cells which contain biomarker protein. The labeled antibody or antibody fragment can then be detected using known techniques.

Antibodies that may be used to detect biomarker protein include any antibody, whether natural or synthetic, full length or a fragment thereof, monoclonal or polyclonal, that binds sufficiently strongly and specifically to the biomarker protein to be detected. An antibody may have a $K_d$ of at most about $10^{-6}$M, $10^{-7}$M, $10^{-8}$M, $10^{-9}$M, $10^{-10}$ M, $10^{-11}$ M, $10^{-12}$ M. The phrase "specifically binds" refers to binding of, for example, an antibody to an epitope or antigen or antigenic determinant in such a manner that binding can be displaced or competed with a second preparation of identical or similar epitope, antigen or antigenic determinant. An antibody may bind preferentially to the biomarker protein relative to other proteins, such as related proteins.

Antibodies are commercially available or may be prepared according to methods known in the art.

Antibodies and derivatives thereof that may be used encompass polyclonal or monoclonal antibodies, chimeric, human, humanized, primatized (CDR-grafted), veneered or single-chain antibodies as well as functional fragments, i.e., biomarker protein binding fragments, of antibodies. For example, antibody fragments capable of binding to a biomarker protein or portions thereof, including, but not limited to, Fv, Fab, Fab' and F(ab') 2 fragments can be used. Such fragments can be produced by enzymatic cleavage or by recombinant techniques. For example, papain or pepsin cleavage can generate Fab or F(ab') 2 fragments, respectively. Other proteases with the requisite substrate specificity can also be used to generate Fab or F(ab') 2 fragments. Antibodies can also be produced in a variety of truncated forms using antibody genes in which one or more stop codons have been introduced upstream of the natural stop site. For example, a chimeric gene encoding a F(ab') 2 heavy chain portion can be designed to include DNA sequences encoding the CH, domain and hinge region of the heavy chain.

Synthetic and engineered antibodies are described in, e.g., Cabilly et al., U.S. Pat. No. 4,816,567 Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Queen et al., European Patent No. 0451216 B1; and Padlan, E. A. et al., EP 0519596 A1. See also, Newman, R. et al., BioTechnology, 10: 1455-1460 (1992), regarding primatized antibody, and Ladner et al., U.S. Pat. No. 4,946,778 and Bird, R. E. et al., Science, 242: 423-426 (1988)) regarding single-chain antibodies. Antibodies produced from a library, e.g., phage display library, may also be used.

In some embodiments, agents that specifically bind to a biomarker protein other than antibodies are used, such as peptides. Peptides that specifically bind to a biomarker protein can be identified by any means known in the art. For example, specific peptide binders of a biomarker protein can be screened for using peptide phage display libraries.

d. Methods for Detection of Biomarker Structural Alterations

The following illustrative methods can be used to identify the presence of a structural alteration in a biomarker nucleic acid and/or biomarker polypeptide molecule in order to, for example, identify PD-L2 or PD-L1 proteins that are both overexpressed and functional.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) Science 241:1077-1080; and Nakazawa et al. (1994) Proc. Natl. Acad. Sci. USA 91:360-364), the latter of which can be particularly useful for detecting point mutations in a biomarker nucleic acid such as a biomarker gene (see Abravaya et al. (1995) Nucleic Acids Res. 23:675-682). This method can include the steps of collecting a sample of cells from a subject, isolating nucleic acid (e.g., genomic, mRNA or both) from the cells of the sample, contacting the nucleic acid sample with one or more primers which specifically hybridize to a biomarker gene under conditions such that hybridization and amplification of the biomarker gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al. (1990) Proc. Natl. Acad. Sci. USA 87:1874-1878), transcriptional amplification system (Kwoh, D. Y. et al. (1989) Proc. Natl. Acad. Sci. USA 86:1173-1177), Q-Beta Replicase (Lizardi, P. M. et al. (1988) Bio-Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a biomarker nucleic acid from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in biomarker nucleic acid can be identified by hybridizing a sample and control nucleic acids, e.g., DNA or RNA, to high density arrays containing hundreds or thousands of oligonucleotide probes (Cronin, M. T. et al. (1996) Hum. Mutat. 7:244-255; Kozal, M. J. et al. (1996) Nat. Med. 2:753-759). For example, biomarker genetic mutations can be identified in two dimensional arrays containing light-generated DNA probes as described in Cronin et al. (1996) supra. Briefly, a first hybridization array of probes can be used to scan through long stretches of DNA in a sample and control to identify base changes between the sequences by making linear arrays of sequential, overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene. Such biomarker genetic mutations can be identified in a variety of contexts, including, for example, germline and somatic mutations.

In yet another embodiment, any of a variety of sequencing reactions known in the art can be used to directly sequence a biomarker gene and detect mutations by comparing the sequence of the sample biomarker with the corresponding wild-type (control) sequence. Examples of sequencing reactions include those based on techniques developed by Maxam and Gilbert (1977) *Proc. Natl. Acad. Sci. USA* 74:560 or Sanger (1977) *Proc. Natl. Acad Sci. USA* 74:5463. It is also contemplated that any of a variety of automated sequencing procedures can be utilized when performing the diagnostic assays (Naeve (1995) *Biotechniques* 19:448-53), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in a biomarker gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes formed by hybridizing (labeled) RNA or DNA containing the wild-type biomarker sequence with potentially mutant RNA or DNA obtained from a tissue sample. The double-stranded duplexes are treated with an agent which cleaves single-stranded regions of the duplex such as which will exist due to base pair mismatches between the control and sample strands. For instance, RNA/DNA duplexes can be treated with RNase and DNA/DNA hybrids treated with SI nuclease to enzymatically digest the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton et al. (1988) *Proc. Natl. Acad. Sci. USA* 85:4397 and Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in biomarker cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a biomarker sequence, e.g., a wild-type biomarker treated with a DNA mismatch repair enzyme, and the cleavage products, if any, can be detected from electrophoresis protocols or the like (e.g., U.S. Pat. No. 5,459,039.)

In other embodiments, alterations in electrophoretic mobility can be used to identify mutations in biomarker genes. For example, single strand conformation polymorphism (SSCP) may be used to detect differences in electrophoretic mobility between mutant and wild type nucleic acids (Orita et al. (1989) *Proc Natl. Acad. Sci USA* 86:2766; see also Cotton (1993) *Mutat. Res.* 285:125-144 and Hayashi (1992) *Genet. Anal. Tech. Appl.* 9:73-79). Single-stranded DNA fragments of sample and control biomarker nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method utilizes heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313:495). When DGGE is used as the method of analysis, DNA will be modified to ensure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA (Rosenbaum and Reissner (1987) *Biophys. Chem.* 265:12753).

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163; Saiki et al. (1989) *Proc. Natl. Acad. Sci. USA* 86:6230). Such allele specific oligonucleotides are hybridized to PCR amplified target DNA or a number of different mutations when the oligonucleotides are attached to the hybridizing membrane and hybridized with labeled target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

3. Anti-Cancer Therapies

The efficacy of PD-1 pathway inhibitor therapy is predicted according to biomarker amount and/or activity associated with a cancer or metaplasia in a subject according to the methods described herein. In one embodiment, such PD-1 pathway inhibitor therapy or combinations of therapies (e.g., one or more PD-1 pathway inhibitors in combination with one or more additional immune checkpoint inhibitors) can be administered once a subject is indicated as being a likely responder to a PD-1 pathway inhibitor. In another embodiment, such PD-1 pathway inhibitor therapy can be avoided once a subject is indicated as not being a likely responder to a PD-1 pathway inhibitor and an alternative treatment regimen, such as targeted and/or untargeted anti-cancer therapies can be administered. Combination therapies are also contemplated and can comprise, for example, one or more chemotherapeutic agents and radiation, one or more chemotherapeutic agents and immunotherapy, or one or more chemotherapeutic agents, radiation and chemotherapy, each combination of which can be with anti-immune checkpoint therapy.

The term "targeted therapy" refers to administration of agents that selectively interact with a chosen biomolecule to thereby treat cancer. For example, anti-PD-1 pathway agents, such as therapeutic monoclonal blocking antibodies, which are well-known in the art and described above, can be used to target tumor microenvironments and cells expressing unwanted components of the PD-1 pathway, such as PD-1, PD-L1, and/or PD-L2.

Immunotherapy is one form of targeted therapy that may comprise, for example, the use of cancer vaccines and/or sensitized antigen presenting cells. For example, an oncolytic virus is a virus that is able to infect and lyse cancer cells, while leaving normal cells unharmed, making them potentially useful in cancer therapy. Replication of oncolytic viruses both facilitates tumor cell destruction and also produces dose amplification at the tumor site. They may also act as vectors for anticancer genes, allowing them to be specifically delivered to the tumor site. The immunotherapy can involve passive immunity for short-term protection of a host, achieved by the administration of pre-formed antibody directed against a cancer antigen or disease antigen (e.g., administration of a monoclonal antibody, optionally linked to a chemotherapeutic agent or toxin, to a tumor antigen). Immunotherapy can also focus on using the cytotoxic lymphocyte-recognized epitopes of cancer cell lines. Alternatively, antisense polynucleotides, ribozymes, RNA interference molecules, triple helix polynucleotides and the like, can be used to selectively modulate biomolecules that are linked to the initiation, progression, and/or pathology of a tumor or cancer.

The term "untargeted therapy" refers to administration of agents that do not selectively interact with a chosen biomolecule yet treat cancer. Representative examples of untargeted therapies include, without limitation, chemotherapy, gene therapy, and radiation therapy.

In one embodiment, chemotherapy is used. Chemotherapy includes the administration of a chemotherapeutic agent. Such a chemotherapeutic agent may be, but is not limited to, those selected from among the following groups of compounds: platinum compounds, cytotoxic antibiotics, antimetabolities, anti-mitotic agents, alkylating agents, arsenic compounds, DNA topoisomerase inhibitors, taxanes, nucleoside analogues, plant alkaloids, and toxins; and synthetic derivatives thereof. Exemplary compounds include, but are not limited to, alkylating agents: cisplatin, treosulfan, and trofosfamide; plant alkaloids: vinblastine, paclitaxel, docetaxol; DNA topoisomerase inhibitors: teniposide, crisnatol, and mitomycin; anti-folates: methotrexate, mycophenolic acid, and hydroxyurea; pyrimidine analogs: 5-fluorouracil, doxifluridine, and cytosine arabinoside; purine analogs: mercaptopurine and thioguanine; DNA antimetabolites: 2'-deoxy-5-fluorouridine, aphidicolin glycinate, and pyrazoloimidazole; and antimitotic agents: halichondrin, colchicine, and rhizoxin. Compositions comprising one or more chemotherapeutic agents (e.g., FLAG, CHOP) may also be used. FLAG comprises fludarabine, cytosine arabinoside (Ara-C) and G-CSF. CHOP comprises cyclophosphamide, vincristine, doxorubicin, and prednisone. In another embodiments, PARP (e.g., PARP-1 and/or PARP-2) inhibitors are used and such inhibitors are well known in the art (e.g., Olaparib, ABT-888, BSI-201, BGP-15 (N-Gene Research Laboratories, Inc.); INO-1001 (Inotek Pharmaceuticals Inc.); PJ34 (Soriano et al., 2001; Pacher et al., 2002b); 3-aminobenzamide (Trevigen); 4-amino-1, 8-naphthalimide; (Trevigen); 6(5H)-phenanthridinone (Trevigen); benzamide (U.S. Pat. Re. 36,397); and NU1025 (Bowman et al.). The mechanism of action is generally related to the ability of PARP inhibitors to bind PARP and decrease its activity. PARP catalyzes the conversion of .beta.-nicotinamide adenine dinucleotide (NAD+) into nicotinamide and poly-ADP-ribose (PAR). Both poly (ADP-ribose) and PARP have been linked to regulation of transcription, cell proliferation, genomic stability, and carcinogenesis (Bouchard V. J. et. al. Experimental Hematology, Volume 31, Number 6, June 2003, pp. 446-454(9); Herceg Z.; Wang Z.-Q. Mutation Research/Fundamental and Molecular Mechanisms of Mutagenesis, Volume 477, Number 1, 2 Jun. 2001, pp. 97-110(14)). Poly(ADP-ribose) polymerase 1 (PARP1) is a key molecule in the repair of DNA single-strand breaks (SSBs) (de Murcia J. et al. 1997. Proc Natl Acad Sci USA 94:7303-7307; Schreiber V, Dantzer F, Ame J C, de Murcia G (2006) Nat Rev Mol Cell Biol 7:517-528; Wang Z Q, et al. (1997) Genes Dev 11:2347-2358). Knockout of SSB repair by inhibition of PARP1 function induces DNA double-strand breaks (DSBs) that can trigger synthetic lethality in cancer cells with defective homology-directed DSB repair (Bryant H E, et al. (2005) Nature 434:913-917; Farmer H, et al. (2005) Nature 434:917-921). The foregoing examples of chemotherapeutic agents are illustrative, and are not intended to be limiting.

In another embodiment, radiation therapy is used. The radiation used in radiation therapy can be ionizing radiation. Radiation therapy can also be gamma rays, X-rays, or proton beams. Examples of radiation therapy include, but are not limited to, external-beam radiation therapy, interstitial implantation of radioisotopes (1-125, palladium, iridium), radioisotopes such as strontium-89, thoracic radiation therapy, intraperitoneal P-32 radiation therapy, and/or total abdominal and pelvic radiation therapy. For a general overview of radiation therapy, see Hellman, Chapter 16: Principles of Cancer Management: Radiation Therapy, 6th edition, 2001, DeVita et al., eds., J. B. Lippencott Company, Philadelphia. The radiation therapy can be administered as external beam radiation or teletherapy wherein the radiation is directed from a remote source. The radiation treatment can also be administered as internal therapy or brachytherapy wherein a radioactive source is placed inside the body close to cancer cells or a tumor mass. Also encompassed is the use of photodynamic therapy comprising the administration of photosensitizers, such as hematoporphyrin and its derivatives, Vertoporfin (BPD-MA), phthalocyanine, photosensitizer Pc4, demethoxy-hypocrellin A; and 2BA-2-DMHA.

In another embodiment, hormone therapy is used. Hormonal therapeutic treatments can comprise, for example, hormonal agonists, hormonal antagonists (e.g., flutamide, bicalutamide, tamoxifen, raloxifene, leuprolide acetate (LUPRON), LH-RH antagonists), inhibitors of hormone biosynthesis and processing, and steroids (e.g., dexamethasone, retinoids, deltoids, betamethasone, cortisol, cortisone, prednisone, dehydrotestosterone, glucocorticoids, mineralocorticoids, estrogen, testosterone, progestins), vitamin A derivatives (e.g., all-trans retinoic acid (ATRA)); vitamin D3 analogs; antigestagens (e.g., mifepristone, onapristone), or antiandrogens (e.g., cyproterone acetate).

In another embodiment, hyperthermia, a procedure in which body tissue is exposed to high temperatures (up to 106° F.) is used. Heat may help shrink tumors by damaging cells or depriving them of substances they need to live. Hyperthermia therapy can be local, regional, and whole-body hyperthermia, using external and internal heating devices. Hyperthermia is almost always used with other forms of therapy (e.g., radiation therapy, chemotherapy, and biological therapy) to try to increase their effectiveness. Local hyperthermia refers to heat that is applied to a very small area, such as a tumor. The area may be heated externally with high-frequency waves aimed at a tumor from a device outside the body. To achieve internal heating, one of several types of sterile probes may be used, including thin, heated wires or hollow tubes filled with warm water; implanted microwave antennae; and radiofrequency electrodes. In regional hyperthermia, an organ or a limb is heated. Magnets and devices that produce high energy are placed over the region to be heated. In another approach, called perfusion, some of the patient's blood is removed, heated, and then pumped (perfused) into the region that is to be heated internally. Whole-body heating is used to treat metastatic cancer that has spread throughout the body. It can be accomplished using warm-water blankets, hot wax, inductive coils (like those in electric blankets), or thermal chambers (similar to large incubators). Hyperthermia does not cause any marked increase in radiation side effects or complications. Heat applied directly to the skin, however, can cause discomfort or even significant local pain in about half the patients treated. It can also cause blisters, which generally heal rapidly.

In still another embodiment, photodynamic therapy (also called PDT, photoradiation therapy, phototherapy, or photochemotherapy) is used for the treatment of some types of cancer. It is based on the discovery that certain chemicals known as photosensitizing agents can kill one-celled organisms when the organisms are exposed to a particular type of light. PDT destroys cancer cells through the use of a fixed-frequency laser light in combination with a photosensitizing agent. In PDT, the photosensitizing agent is injected into the bloodstream and absorbed by cells all over the body. The agent remains in cancer cells for a longer time than it does in normal cells. When the treated cancer cells are exposed to laser light, the photosensitizing agent absorbs the light and produces an active form of oxygen that destroys the treated cancer cells. Light exposure must be timed carefully so that it occurs when most of the photosensitizing agent has left healthy cells but is still present in the cancer cells. The laser light used in PDT can be directed through a fiber-optic (a very thin glass strand). The fiber-optic is placed close to the cancer to deliver the proper amount of light. The fiber-optic can be directed through a bronchoscope into the lungs for the treatment of lung cancer or through an endoscope into the esophagus for the treatment of esophageal cancer. An advantage of PDT is that it causes minimal damage to healthy tissue. However, because the laser light currently in use cannot pass through more than about 3 centimeters of tissue (a little more than one and an eighth inch), PDT is mainly used to treat tumors on or just under the skin or on the lining of internal organs. Photodynamic therapy makes the skin and eyes sensitive to light for 6 weeks or more after treatment. Patients are advised to avoid direct sunlight and bright indoor light for at least 6 weeks. If patients must go outdoors, they need to wear protective clothing, including sunglasses. Other temporary side effects of PDT are related to the treatment of specific areas and can include coughing, trouble swallowing, abdominal pain, and painful breathing or shortness of breath. In December 1995, the U.S. Food and Drug Administration (FDA) approved a photosensitizing agent called porfimer sodium, or Photofrin®, to relieve symptoms of esophageal cancer that is causing an obstruction and for esophageal cancer that cannot be satisfactorily treated with lasers alone. In January 1998, the FDA approved porfimer sodium for the treatment of early nonsmall cell lung cancer in patients for whom the usual treatments for lung cancer are not appropriate. The National Cancer Institute and other institutions are supporting clinical trials (research studies) to evaluate the use of photodynamic therapy for several types of cancer, including cancers of the bladder, brain, larynx, and oral cavity.

In yet another embodiment, laser therapy is used to harness high-intensity light to destroy cancer cells. This technique is often used to relieve symptoms of cancer such as bleeding or obstruction, especially when the cancer cannot be cured by other treatments. It may also be used to treat cancer by shrinking or destroying tumors. The term "laser" stands for light amplification by stimulated emission of radiation. Ordinary light, such as that from a light bulb, has many wavelengths and spreads in all directions. Laser light, on the other hand, has a specific wavelength and is focused in a narrow beam. This type of high-intensity light contains a lot of energy. Lasers are very powerful and may be used to cut through steel or to shape diamonds. Lasers also can be used for very precise surgical work, such as repairing a damaged retina in the eye or cutting through tissue (in place of a scalpel). Although there are several different kinds of lasers, only three kinds have gained wide use in medicine: Carbon dioxide ($CO_2$) laser—This type of laser can remove thin layers from the skin's surface without penetrating the deeper layers. This technique is particularly useful in treating tumors that have not spread deep into the skin and certain precancerous conditions. As an alternative to traditional scalpel surgery, the $CO_2$ laser is also able to cut the skin. The laser is used in this way to remove skin cancers. Neodymium:yttrium-aluminum-garnet (Nd:YAG) laser-Light from this laser can penetrate deeper into tissue than light from the other types of lasers, and it can cause blood to clot quickly. It can be carried through optical fibers to less accessible parts of the body. This type of laser is sometimes used to treat throat cancers. Argon laser—This laser can pass through only superficial layers of tissue and is therefore useful in dermatology and in eye surgery. It also is used with light-sensitive dyes to treat tumors in a procedure known as photodynamic therapy (PDT). Lasers have several advantages over standard surgical tools, including: Lasers are more precise than scalpels. Tissue near an incision is protected, since there is little contact with surrounding skin or other tissue. The heat produced by lasers sterilizes the surgery site, thus reducing the risk of infection. Less operating time may be needed because the precision of the laser allows for a smaller incision. Healing time is often shortened; since laser heat seals blood vessels, there is less bleeding, swelling, or scarring. Laser surgery may be less complicated. For example, with fiber optics, laser light can be directed to parts of the body without making a large incision. More procedures may be done on an outpatient basis. Lasers can be used in two ways to treat cancer: by shrinking or destroying a tumor with heat, or by activating a chemical—known as a photosensitizing agent—that destroys cancer cells. In PDT, a photosensitizing agent is retained in cancer cells and can be stimulated by light to cause a reaction that kills cancer cells. $CO_2$ and Nd:YAG lasers are used to shrink or destroy tumors. They may be used with endoscopes, tubes that allow physicians to see into certain areas of the body, such as the bladder. The light from some lasers can be transmitted through a flexible endoscope fitted with fiber optics. This allows physicians to see and work in parts of the body that could not otherwise be reached except by surgery and therefore allows very precise aiming of the laser beam. Lasers also may be used with low-power microscopes, giving the doctor a clear view of the site being treated. Used with other instruments, laser systems can produce a cutting area as small as 200 microns in diameter—less than the width of a very fine thread. Lasers are used to treat many types of cancer. Laser surgery is a standard treatment for certain stages of glottis (vocal cord), cervical, skin, lung, vaginal, vulvar, and penile cancers. In addition to its use to destroy the cancer, laser surgery is also used to help relieve symptoms caused by cancer (palliative care). For example, lasers may be used to shrink or destroy a tumor that is blocking a patient's trachea (windpipe), making it easier to breathe. It is also sometimes used for palliation in colorectal and anal cancer. Laser-induced interstitial thermotherapy (LITT) is one of the most recent developments in laser therapy. LITT uses the same idea as a cancer treatment called hyperthermia; that heat may help shrink tumors by damaging cells or depriving them of substances they need to live. In this treatment, lasers are directed to interstitial areas (areas between organs) in the body. The laser light then raises the temperature of the tumor, which damages or destroys cancer cells.

The duration and/or dose of treatment with anti-immune checkpoint therapies may vary according to the particular anti-immune checkpoint agent or combination thereof. An appropriate treatment time for a particular cancer therapeutic agent will be appreciated by the skilled artisan. The present invention contemplates the continued assessment of optimal treatment schedules for each cancer therapeutic agent, where the phenotype of the cancer of the subject as determined by the methods of the present invention is a factor in determining optimal treatment doses and schedules.

Any means for the introduction of a polynucleotide into mammals, human or non-human, or cells thereof may be adapted to the practice of this invention for the delivery of the various constructs of the present invention into the intended recipient. In one embodiment of the present invention, the DNA constructs are delivered to cells by transfection, i.e., by delivery of "naked" DNA or in a complex with a colloidal dispersion system. A colloidal system includes macromolecule complexes, nanocapsules, microspheres, beads, and lipid-based systems including oil-in-water emulsions, micelles, mixed micelles, and liposomes. The preferred colloidal system of this invention is a lipid-complexed or liposome-formulated DNA. In the former approach, prior to formulation of DNA, e.g., with lipid, a plasmid containing a transgene bearing the desired DNA constructs may first be experimentally optimized for expression (e.g., inclusion of an intron in the 5' untranslated region and elimination of unnecessary sequences (Felgner, et al., Ann NY Acad Sci 126-139, 1995). Formulation of DNA, e.g. with various lipid or liposome materials, may then be effected using known methods and materials and delivered to the recipient mammal. See, e.g., Canonico et al, Am J Respir Cell Mol Biol 10:24-29, 1994; Tsan et al, Am J Physiol 268; Alton et al., Nat Genet. 5:135-142, 1993 and U.S. Pat. No. 5,679,647 by Carson et al.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs, which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand. Naked DNA or DNA associated with a delivery vehicle, e.g., liposomes, can be administered to several sites in a subject (see below).

Nucleic acids can be delivered in any desired vector. These include viral or non-viral vectors, including adenovirus vectors, adeno-associated virus vectors, retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus). Nucleic acids can be administered in any desired format that provides sufficiently efficient delivery levels, including in virus particles, in liposomes, in nanoparticles, and complexed to polymers.

The nucleic acids encoding a protein or nucleic acid of interest may be in a plasmid or viral vector, or other vector as is known in the art. Such vectors are well known and any can be selected for a particular application. In one embodiment of the present invention, the gene delivery vehicle comprises a promoter and a demethylase coding sequence. Preferred promoters are tissue-specific promoters and promoters which are activated by cellular proliferation, such as the thymidine kinase and thymidylate synthase promoters. Other preferred promoters include promoters which are activatable by infection with a virus, such as the α- and β-interferon promoters, and promoters which are activatable by a hormone, such as estrogen. Other promoters which can be used include the Moloney virus LTR, the CMV promoter, and the mouse albumin promoter. A promoter may be constitutive or inducible.

In another embodiment, naked polynucleotide molecules are used as gene delivery vehicles, as described in WO 90/11092 and U.S. Pat. No. 5,580,859. Such gene delivery vehicles can be either growth factor DNA or RNA and, in certain embodiments, are linked to killed adenovirus. Curiel et al., Hum. Gene. Ther. 3:147-154, 1992. Other vehicles which can optionally be used include DNA-ligand (Wu et al., J. Biol. Chem. 264:16985-16987, 1989), lipid-DNA combinations (Felgner et al., Proc. Natl. Acad. Sci. USA 84:7413 7417, 1989), liposomes (Wang et al., Proc. Natl. Acad. Sci. 84:7851-7855, 1987) and microprojectiles (Williams et al., Proc. Natl. Acad. Sci. 88:2726-2730, 1991).

A gene delivery vehicle can optionally comprise viral sequences such as a viral origin of replication or packaging signal. These viral sequences can be selected from viruses such as astrovirus, coronavirus, orthomyxovirus, papovavirus, paramyxovirus, parvovirus, picornavirus, poxvirus, retrovirus, togavirus or adenovirus. In a preferred embodiment, the growth factor gene delivery vehicle is a recombinant retroviral vector. Recombinant retroviruses and various uses thereof have been described in numerous references including, for example, Mann et al., Cell 33:153, 1983, Cane and Mulligan, Proc. Nat'l. Acad. Sci. USA 81:6349, 1984, Miller et al., Human Gene Therapy 1:5-14, 1990, U.S. Pat. Nos. 4,405,712, 4,861,719, and 4,980,289, and PCT Application Nos. WO 89/02,468, WO 89/05,349, and WO 90/02,806. Numerous retroviral gene delivery vehicles can be utilized in the present invention, including for example those described in EP 0,415,731; WO 90/07936; WO 94/03622; WO 93/25698; WO 93/25234; U.S. Pat. No. 5,219,740; WO 9311230; WO 9310218; Vile and Hart, Cancer Res. 53:3860-3864, 1993; Vile and Hart, Cancer Res. 53:962-967, 1993; Ram et al., Cancer Res. 53:83-88, 1993; Takamiya et al., J. Neurosci. Res. 33:493-503, 1992; Baba et al., J. Neurosurg. 79:729-735, 1993 (U.S. Pat. No. 4,777,127, GB 2,200,651, EP 0,345,242 and WO91/02805).

Other viral vector systems that can be used to deliver a polynucleotide of the present invention have been derived from herpes virus, e.g., Herpes Simplex Virus (U.S. Pat. No. 5,631,236 by Woo et al., issued May 20, 1997 and WO 00/08191 by Neurovex), vaccinia virus (Ridgeway (1988) Ridgeway, "Mammalian expression vectors," In: Rodriguez R L, Denhardt D T, ed. Vectors: A survey of molecular cloning vectors and their uses. Stoneham: Butterworth; Baichwal and Sugden (1986) "Vectors for gene transfer derived from animal DNA viruses: Transient and stable expression of transferred genes," In: Kucherlapati R, ed. Gene transfer. New York: Plenum Press; Coupar et al. (1988) Gene, 68:1-10), and several RNA viruses. Preferred viruses include an alphavirus, a poxivirus, an arena virus, a vaccinia virus, a polio virus, and the like. They offer several attractive features for various mammalian cells (Friedmann (1989) Science, 244:1275-1281; Ridgeway, 1988, supra; Baichwal and Sugden, 1986, supra; Coupar et al., 1988; Horwich et al. (1990) J. Virol., 64:642-650).

In other embodiments, target DNA in the genome can be manipulated using well-known methods in the art. For example, the target DNA in the genome can be manipulated by deletion, insertion, and/or mutation are retroviral insertion, artificial chromosome techniques, gene insertion, random insertion with tissue specific promoters, gene targeting, transposable elements and/or any other method for introducing foreign DNA or producing modified DNA/modified nuclear DNA. Other modification techniques include deleting DNA sequences from a genome and/or altering nuclear DNA sequences. Nuclear DNA sequences, for example, may be altered by site-directed mutagenesis.

In other embodiments, recombinant biomarker polypeptides, and fragments thereof, can be administered to subjects. In some embodiments, fusion proteins can be constructed and administered which have enhanced biological properties. In addition, the biomarker polypeptides, and fragment thereof, can be modified according to well-known pharmacological methods in the art (e.g., pegylation, glycosylation, oligomerization, etc.) in order to further enhance desirable biological activities, such as increased bioavailability and decreased proteolytic degradation.

4. Clinical Efficacy

Clinical efficacy can be measured by any method known in the art. For example, the response to a therapy, such as anti-immune checkpoint therapies, relates to any response of the cancer, e.g., a tumor, to the therapy, preferably to a change in tumor mass and/or volume after initiation of neoadjuvant or adjuvant chemotherapy. Tumor response may be assessed in a neoadjuvant or adjuvant situation where the size of a tumor after systemic intervention can be compared to the initial size and dimensions as measured by CT, PET, mammogram, ultrasound or palpation and the cellularity of a tumor can be estimated histologically and compared to the cellularity of a tumor biopsy taken before initiation of treatment. Response may also be assessed by caliper measurement or pathological examination of the tumor after biopsy or surgical resection. Response may be recorded in a quantitative fashion like percentage change in tumor volume or cellularity or using a semi-quantitative scoring system such as residual cancer burden (Symmans et al., *J. Clin. Oncol.* (2007) 25:4414-4422) or Miller-Payne score (Ogston et al., (2003) *Breast* (Edinburgh, Scotland) 12:320-327) in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of tumor response may be performed early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed.

In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular anti-immune checkpoint therapeutic regimen is at least 25%, 30%, 35%, 40%, 45%, 50%, 55%, 60%, 65%, 70%, 75%, 80%, 85%, or more.

Additional criteria for evaluating the response to anti-immune checkpoint therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence.

For example, in order to determine appropriate threshold values, a particular anti-immune checkpoint therapeutic regimen can be administered to a population of subjects and the outcome can be correlated to biomarker measurements that were determined prior to administration of any anti-immune checkpoint therapy. The outcome measurement may be pathologic response to therapy given in the neoadjuvant setting. Alternatively, outcome measures, such as overall survival and disease-free survival can be monitored over a period of time for subjects following anti-immune checkpoint therapy for whom biomarker measurement values are known. In certain embodiments, the same doses of anti-immune checkpoint agents are administered to each subject. In related embodiments, the doses administered are standard doses known in the art for anti-immune checkpoint agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months. Biomarker measurement threshold values that correlate to outcome of an anti-immune checkpoint therapy can be determined using methods such as those described in the Examples section.

5. Further Uses and Methods of the Present Invention

The compositions described herein can be used in a variety of diagnostic, prognostic, and therapeutic applications.

a. Screening Methods

One aspect of the present invention relates to screening assays, including non-cell based assays. In one embodiment, the assays provide a method for identifying whether a cancer is likely to respond to PD-1 pathway inhibitor therapy and/or whether an agent can inhibit the growth of or kill a cancer cell that is unlikely to respond to PD-1 pathway inhibitor therapy.

In one embodiment, the present invention relates to assays for screening test agents which bind to, or modulate the biological activity of, at least one biomarker listed in Table 1. In one embodiment, a method for identifying such an agent entails determining the ability of the agent to modulate, e.g. inhibit, the at least one biomarker listed in Table 1.

In one embodiment, an assay is a cell-free or cell-based assay, comprising contacting at least one biomarker listed in Table 1, with a test agent, and determining the ability of the test agent to modulate (e.g. inhibit) the enzymatic activity of the biomarker, such as by measuring direct binding of substrates or by measuring indirect parameters as described below.

For example, in a direct binding assay, biomarker protein (or their respective target polypeptides or molecules) can be coupled with a radioisotope or enzymatic label such that binding can be determined by detecting the labeled protein or molecule in a complex. For example, the targets can be labeled with $^{125}$I, $^{35}$S, $^{14}$C, or $^{3}$H, either directly or indirectly, and the radioisotope detected by direct counting of radioemmission or by scintillation counting. Alternatively, the targets can be enzymatically labeled with, for example, horseradish peroxidase, alkaline phosphatase, or luciferase, and the enzymatic label detected by determination of conversion of an appropriate substrate to product. Determining the interaction between biomarker and substrate can also be accomplished using standard binding or enzymatic analysis assays. In one or more embodiments of the above described assay methods, it may be desirable to immobilize polypeptides or molecules to facilitate separation of complexed from uncomplexed forms of one or both of the proteins or molecules, as well as to accommodate automation of the assay.

Binding of a test agent to a target can be accomplished in any vessel suitable for containing the reactants. Non-limiting examples of such vessels include microtiter plates, test tubes, and micro-centrifuge tubes. Immobilized forms of the antibodies of the present invention can also include antibodies bound to a solid phase like a porous, microporous (with an average pore diameter less than about one micron) or macroporous (with an average pore diameter of more than about 10 microns) material, such as a membrane, cellulose, nitrocellulose, or glass fibers; a bead, such as that made of agarose or polyacrylamide or latex; or a surface of a dish, plate, or well, such as one made of polystyrene.

In an alternative embodiment, determining the ability of the agent to modulate the interaction between the biomarker and a substrate or a biomarker and its natural binding partner can be accomplished by determining the ability of the test agent to modulate the activity of a polypeptide or other product that functions downstream or upstream of its position within the signaling pathway (e.g., feedback loops). Such feedback loops are well-known in the art (see, for example, Chen and Guillemin (2009) *Int. J. Tryptophan Res.* 2:1-19).

The present invention further pertains to novel agents identified by the above-described screening assays. Accordingly, it is within the scope of this invention to further use an agent identified as described herein in an appropriate animal model. For example, an agent identified as described herein can be used in an animal model to determine the efficacy, toxicity, or side effects of treatment with such an agent. Alternatively, an antibody identified as described herein can be used in an animal model to determine the mechanism of action of such an agent.

b. Predictive Medicine

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining the amount and/or activity level of a biomarker listed in Table 1 in the context of a biological sample (e.g., blood, serum, cells, or tissue) to thereby determine whether an individual afflicted with a cancer is likely to respond to PD-1 pathway inhibitor therapy, whether in an original or recurrent cancer. Such assays can be used for prognostic or predictive purpose to thereby prophylactically treat an individual prior to the onset or after recurrence of a disorder characterized by or associated with biomarker polypeptide, nucleic acid expression or activity. The skilled artisan will appreciate that any method can use one or more (e.g., combinations) of biomarkers listed in Table 1.

Another aspect of the present invention pertains to monitoring the influence of agents (e.g., drugs, compounds, and small nucleic acid-based molecules) on the expression or activity of a biomarker listed in Table 1. These and other agents are described in further detail in the following sections.

The skilled artisan will also appreciated that, in certain embodiments, the methods of the present invention implement a computer program and computer system. For example, a computer program can be used to perform the algorithms described herein. A computer system can also store and manipulate data generated by the methods of the present invention which comprises a plurality of biomarker signal changes/profiles which can be used by a computer system in implementing the methods of this invention. In certain embodiments, a computer system receives biomarker expression data; (ii) stores the data; and (iii) compares the data in any number of ways described herein (e.g., analysis relative to appropriate controls) to determine the state of informative biomarkers from cancerous or pre-cancerous tissue. In other embodiments, a computer system (i) compares the determined expression biomarker level to a threshold value; and (ii) outputs an indication of whether said biomarker level is significantly modulated (e.g., above or below) the threshold value, or a phenotype based on said indication.

In certain embodiments, such computer systems are also considered part of the present invention. Numerous types of computer systems can be used to implement the analytic methods of this invention according to knowledge possessed by a skilled artisan in the bioinformatics and/or computer arts. Several software components can be loaded into memory during operation of such a computer system. The software components can comprise both software components that are standard in the art and components that are special to the present invention (e.g., dCHIP software described in Lin et al. (2004) *Bioinformatics* 20, 1233-1240; radial basis machine learning algorithms (RBM) known in the art).

The methods of the present invention can also be programmed or modeled in mathematical software packages that allow symbolic entry of equations and high-level specification of processing, including specific algorithms to be used, thereby freeing a user of the need to procedurally program individual equations and algorithms. Such packages include, e.g., Matlab from Mathworks (Natick, Mass.), Mathematica from Wolfram Research (Champaign, Ill.) or S-Plus from MathSoft (Seattle, Wash.).

In certain embodiments, the computer comprises a database for storage of biomarker data. Such stored profiles can be accessed and used to perform comparisons of interest at a later point in time. For example, biomarker expression profiles of a sample derived from the non-cancerous tissue of a subject and/or profiles generated from population-based distributions of informative loci of interest in relevant populations of the same species can be stored and later compared to that of a sample derived from the cancerous tissue of the subject or tissue suspected of being cancerous of the subject.

In addition to the exemplary program structures and computer systems described herein, other, alternative program structures and computer systems will be readily apparent to the skilled artisan. Such alternative systems, which do not depart from the above described computer system and programs structures either in spirit or in scope, are therefore intended to be comprehended within the accompanying claims.

c. Diagnostic Assays

The present invention provides, in part, methods, systems, and code for accurately classifying whether a biological sample is associated with a cancer that is likely to respond to PD-1 pathway inhibitor therapy. In some embodiments, the present invention is useful for classifying a sample (e.g., from a subject) as associated with or at risk for responding to or not responding to PD-1 pathway inhibitor therapy using a statistical algorithm and/or empirical data (e.g., the amount or activity of a biomarker listed in Table 1).

An exemplary method for detecting the amount or activity of a biomarker listed in Table 1, and thus useful for classifying whether a sample is likely or unlikely to respond to PD-1 pathway inhibitor therapy involves obtaining a biological sample from a test subject and contacting the biological sample with an agent, such as a protein-binding agent like an antibody or antigen-binding fragment thereof, or a nucleic acid-binding agent like an oligonucleotide, capable of detecting the amount or activity of the biomarker in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a based upon a prediction or probability value and the presence or level of the biomarker. The use of a single learning statistical classifier system typically classifies the sample as, for example, a likely anti-immune checkpoint therapy responder or progressor sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the sample classification results to a clinician, e.g., an oncologist.

In another embodiment, the diagnosis of a subject is followed by administering to the individual a therapeutically effective amount of a defined treatment based upon the diagnosis.

In one embodiment, the methods further involve obtaining a control biological sample (e.g., biological sample from a subject who does not have a cancer or whose cancer is susceptible to PD-1 pathway inhibitor therapy), a biological sample from the subject during remission, or a biological sample from the subject during treatment for developing a cancer progressing despite PD-1 pathway inhibitor therapy.

d. Prognostic Assays

The diagnostic methods described herein can furthermore be utilized to identify subjects having or at risk of developing a cancer that is likely or unlikely to be responsive to PD-1 pathway inhibitor therapy. The assays described herein, such as the preceding diagnostic assays or the following assays, can be utilized to identify a subject having or at risk of developing a disorder associated with a misregulation of the amount or activity of at least one biomarker described in Table 1, such as in cancer. Alternatively, the prognostic assays can be utilized to identify a subject having or at risk for developing a disorder associated with a misregulation of the at least one biomarker described in Table 1, such as in cancer. Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat a disease or disorder associated with the aberrant biomarker expression or activity.

e. Treatment Methods

The compositions described herein (including dual binding antibodies and derivatives and conjugates thereof) can be used in a variety of in vitro and in vivo therapeutic applications using the formulations and/or combinations described herein. In one embodiment, anti-immune checkpoint agents can be used to treat cancers determined to be responsive thereto. For example, antibodies that block the interaction between PD-1 and one or both of its ligands, PD-L1 and PD-L2 (e.g., PD-L1 binding to PD-1, PD-L2 binding to PD-1, and the like) can be used to treat cancer in subjects identified as likely responders thereto.

6. Pharmaceutical Compositions

In another aspect, the present invention provides pharmaceutically acceptable compositions which comprise a therapeutically-effective amount of an agent that modulates (e.g., decreases) biomarker expression and/or activity, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "therapeutically-effective amount" as used herein means that amount of an agent that modulates (e.g., inhibits) biomarker expression and/or activity, or expression and/or activity of the complex, or composition comprising an agent that modulates (e.g., inhibits) biomarker expression and/or activity, or expression and/or activity of the complex, which is effective for producing some desired therapeutic effect, e.g., cancer treatment, at a reasonable benefit/risk ratio.

The phrase "pharmaceutically acceptable" is employed herein to refer to those agents, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier must be "acceptable" in the sense of being compatible with the other ingredients of the formulation and not injurious to the subject. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "pharmaceutically-acceptable salts" refers to the relatively non-toxic, inorganic and organic acid addition salts of the agents that modulates (e.g., inhibits) biomarker expression and/or activity, or expression and/or activity of the complex encompassed by the present invention. These salts can be prepared in situ during the final isolation and purification of the therapeutic agents, or by separately reacting a purified therapeutic agent in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like (See, for example, Berge et al. (1977) "Pharmaceutical Salts", *J. Pharm. Sci.* 66:1-19).

In other cases, the agents useful in the methods of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of agents that modulates (e.g., inhibits) biomarker expression and/or activity, or expression and/or activity of the complex. These salts can likewise be prepared in situ during the final isolation and purification of the therapeutic agents, or by separately reacting the purified therapeutic agent in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like (see, for example, Berge et al., supra).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations useful in the methods of the present invention include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient, which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association an agent that modulates (e.g., inhibits) biomarker expression and/or activity, with the carrier and, optionally, one or more accessory ingredients. In general, the formulations are prepared by uniformly and intimately bringing into association a therapeutic agent with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a therapeutic agent as an active ingredient. A compound may also be administered as a bolus, electuary or paste.

In solid dosage forms for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered peptide or peptidomimetic moistened with an inert liquid diluent.

Tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions, which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions, which can be used include polymeric substances and waxes. The active ingredient can also be in micro-encapsulated form, if appropriate, with one or more of the above-described excipients.

Liquid dosage forms for oral administration include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active agent may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing one or more therapeutic agents with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Formulations which are suitable for vaginal administration also include pessaries, tampons, creams, gels, pastes, foams or spray formulations containing such carriers as are known in the art to be appropriate.

Dosage forms for the topical or transdermal administration of an agent that modulates (e.g., inhibits) biomarker expression and/or activity include powders, sprays, ointments, pastes, creams, lotions, gels, solutions, patches and inhalants. The active component may be mixed under sterile conditions with a pharmaceutically-acceptable carrier, and with any preservatives, buffers, or propellants which may be required.

The ointments, pastes, creams and gels may contain, in addition to a therapeutic agent, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an agent that modulates (e.g., inhibits) biomarker expression and/or activity, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The agent that modulates (e.g., inhibits) biomarker expression and/or activity, can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a therapeutic agent to the body. Such dosage forms can be made by dissolving or dispersing the agent in the proper medium. Absorption enhancers can also be used to increase the flux of the peptidomimetic across the skin. The rate of such flux can be controlled by either providing a rate controlling membrane or dispersing the peptidomimetic in a polymer matrix or gel.

Ophthalmic formulations, eye ointments, powders, solutions and the like, are also contemplated as being within the scope of this invention.

Pharmaceutical compositions of this invention suitable for parenteral administration comprise one or more therapeutic agents in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the present invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of an agent that modulates (e.g., inhibits) biomarker expression and/or activity, in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions, which are compatible with body tissue.

When the therapeutic agents of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

Actual dosage levels of the active ingredients in the pharmaceutical compositions of this invention may be determined by the methods of the present invention so as to obtain an amount of the active ingredient, which is effective to achieve the desired therapeutic response for a particular subject, composition, and mode of administration, without being toxic to the subject.

The nucleic acid molecules of the present invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) Proc. Natl. Acad. Sci. USA 91:3054 3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The present invention also encompasses kits for detecting and/or modulating biomarkers described herein. A kit of the present invention may also include instructional materials disclosing or describing the use of the kit or an antibody of the disclosed invention in a method of the disclosed invention as provided herein. A kit may also include additional components to facilitate the particular application for which the kit is designed. For example, a kit may additionally contain means of detecting the label (e.g., enzyme substrates for enzymatic labels, filter sets to detect fluorescent labels, appropriate secondary labels such as a sheep anti-mouse-HRP, etc.) and reagents necessary for controls (e.g., control biological samples or standards). A kit may additionally include buffers and other reagents recognized for use in a method of the disclosed invention. Non-limiting examples include agents to reduce non-specific binding, such as a carrier protein or a detergent.

EXEMPLIFICATION

This invention is further illustrated by the following examples, which should not be construed as limiting.

Example 1: Materials and Methods for Examples 2-8 a. Patient Samples

Tumor microarrays (TMAs) were constructed from 354 resected stage 1-4 esophageal adenocarcinomas. All patients underwent esophagectomy without neoadjuvant treatment. Depending on tumor size, up to three 0.6 mm cores were obtained from each tumor. The number of cores varied per tumor and was dependent on tumor size; approximately 75% of cases were represented by 3 cores. Detailed clinical annotation was performed by trained data abstractors for relevant demographic, comorbidity, tumor pathology and stage, and recurrence and survival variables (FIG. 5). The studies were reviewed and approved by the Institutional Review Board.

b. Immunohistochemistry

Anti-PD-1 (clone EH33), anti-PD-L1 (clone 9A11) and anti-PD-L2 (clone 366C.9E5) antibodies are mouse monoclonal antibodies obtained from Dr. Gordon Freeman's laboratory. PD-1, PD-L2, PD-L1 and PD-L1/CD68 double staining were performed as described in Shi et al. (2014) *Amer. J. Surg. Pathol.* 38:1715-1723 and Chen et al. (2013) *Clin. Cancer Res.* 19:3462-3473. Briefly, for PD-1 immunohistochemical staining, 4-micrometer-thick sections were deparaffinized, rehydrated, and heated in a steamer for 30 minutes for antigen retrieval in citrate buffer pH 6.0 (Invitrogen, Carlsbad, Calif.). After cooling for 20 minutes, sections were incubated with peroxidase block (DAKO, Carpinteria, Calif.) for five minutes and serum-free protein block (DAKO) for 20 minutes. Slides were then incubated at room temperature for one hour with primary antibodies against PD-1 (clone EH33) diluted in Da Vinci green diluent (Biocare Medical, Concord, Calif.). For the secondary antibody, EnVision™ anti-mouse HRP-labeled polymer (DAKO) was applied for 30 minutes. Immunoreactivity for PD-1 was detected in the tumor infiltrating lymphocytes (TIL). Positive TIL cells were counted under a 20× middle power field. For the TMA slides, all positive TILs in each core were counted, whereas five representative areas in each slide with whole tissue were chosen to count, and the average absolute number was recorded.

PD-L1 (clone 405.9A11) staining was observed in cytoplasm and membranes of tumor cells and immune cells and was considered positive if ≥5% of tumor cells had membranous staining or any positive immune cells. PD-L2 (clone 366C.9E5) staining was observed in cytoplasm and membranes of tumor cells and was scored based on the number of positive cores and staining intensity. A tumor core was considered PD-L2 positive when ≥50% of tumor cells on TMAs or ≥10% of tumor cells on whole-tissue slides showed membranous and/or cytoplasmic immunoreactivity (e.g., moderate-strong PD-L2 staining in cytoplasm and/or membrane). The intensity was scored as follows: 0, negative; 1, weak; 2, moderate; 3, strong. For whole-tissue slides, the percentage of positively stained tumor cells for these two antibodies were assessed. The cutoff of PD-L2 positivity in tumor cells on whole-tissue slides is ≥10% and a moderate to strong (2+ and 3+) staining intensity. Double staining for PD-L1 and CD163: After PD-L1 staining and washing, the slides were incubated with mouse monoclonal antibody anti-CD163 (10D6, 1:200, Neomarkers, Fremont, Calif.) diluted in Da Vinci diluent overnight in cold room. The secondary anti-mouse AP-linked antibody (A3562, DAKO) was used for 30 minutes and the slides were developed by liquid permanent red solution (K0640, DAKO).

All the slides were evaluated and scored by a pathologist blinded to clinical data. The scoring for each marker was performed at least twice with one-week interval.

c. Cell Lines and Cell Line Treatment

The human esophageal adenocarcinomas cell lines, OE19, OACM5.1C, ESO26, KYAE-1, and FLO-1, were purchased from the European Collection of cell cultures (ECACC) and have been authenticated by SNP arrays in 2012. MKN7 cells were purchased from the Broad Institute and characterized within the Cancer Cell Line Encyclopedia (CCLE) project. OE33 was purchased from the Sigma (St. Louis, Mo.). Only low-passage frozen cell aliquots of original stocks were used for further experiments and therefore cell lines were not revalidated.

Cell lines OE19, OACM5.1C, ESO26, OE33, KYAE-1, and MKN7 were cultured in RPMI-1640 and FLO-1 in DMEM both supplemented with 10% heat-inactivated FBS, 100 U/mL penicillin, 100 mg/mL streptomycin, and 10 mmol/L HEPES.

FFPE cell pellets were generated by harvesting $10^7$ cells with PBS/EDTA, washing, and fixing in 2 mL 10% formalin at room temperature for 20 minutes. Cells were then washed, suspended in matrigel, processed, embedded in paraffin as a cell pellet tissue microarray, and cut onto glass slides as per standard histologic procedures.

For IL-4 and IL-13 treatment, cells were plated in 6-well plates and stimulated with human recombinant IL-4 (20 ng/ml; BD Pharmingen, #554605) and human recombinant IL-13 (20 ng/ml; Peprotech, #200-13) or with medium for 4, 8, and 24 hours. STAT6 expression and STAT6 phosphorylation were determined by Western blot analyses. Cells were washed twice with PBS and lysed using nuclear and cytoplasmic extraction reagents (NE-PER, Thermo Scientific, #78833). Membranes were incubated with one of the following antibodies: mouse monoclonal anti-pSTAT6 (pY641, 1:500; BD Biosciences; Pharmingen), rabbit polyclonal anti-STAT6 antibody (S-20 1:500; Santa Cruz Biotechnology Inc.), or mouse monoclonal anti-β-actin (1:10,000; Sigma-Aldrich). When necessary, membranes were stripped in 0.2 M glycine/1% w/v sodium dodecyl sulfate, pH 2.5, blocked, and reprobed.

For STAT6 knockdown, transfection of siRNA against STAT6 was performed using siRNA for the STAT6 gene (ON-TARGETplus™ SMARTPOOL, L-006690-00-0005). Non-targeting control siRNA was similarly obtained from Dharmacon (ON-TARGETplus Non-Targeting Pool D-001810-10-05). Cells were plated in a 6-well plate and transfected at a density of $2\times10^5$ cells per well and transfected on day 2 with 40 nM siRNA (OE33) or 20 nM siRNA (MKN7) following complexation with 7.5 µl Lipofectamine RNAiMAX™ (Invitrogen, #13778150), according to the manufacturer's instructions. Knockdown efficiency was assessed at the protein level by Western blot analysis. Cells were lysed in ice-cold RIPA buffer containing phosphatase and protease inhibitors. PD-L2 expression was assessed by qRT-PCR and flow cytometry.

d. Real-Time PCR

Total RNA was extracted using the RNeasy® mini kit (QIAGEN; #) following the manufacturer's instructions. Possible genomic DNA contaminants were removed by DNase treatment with the RNase-free DNase set (Qiagen). Complementary DNA synthesis was performed using the iScript™ complementary DNA synthesis kit (Bio-Rad, Richmond, Calif.). Quantitative reverse transcription-PCR was performed using SYBR® Green PCR master mix and the following primers: PD-L2 forward: 5'-GGCAGAAACTTCAGCTGTGTG-3', PD-L2 reverse: 5'-GGTCCTGGGTTCCATCTGAC-3', STAT6 forward: 5'-GGCATCTTCTGGGTGACTGG-3', STAT6 reverse: 5'-GGCATCTTCTGGGTGACTGG-3', CYCLOPHILIN_ forward: 5'-CTCGAATAAGTTTGACTTGTGTTT-3', CYCLOPHILIN_reverse: 5'-CTAGGCATGGGAGG-GAACA-3'. Triplicates were run for each sample. CYCLOPHILIN was used as internal control, and the ΔΔCT method was used to calculate relative mRNA levels.

e. Flow Cytometry

For cell lines, adherent cells were treated for 4-20 minutes with EDTA and harvested for flow cytometry. For PD-L2 expression analysis, cells were stained with anti-human PD-L2 antibody (clone 24F.10C12 PE, BioLegend,

329605) and isotype control mouse IgG2a (clone MOPC-173, PE, BioLegend, #400213).

For xenografts, freshly biopsied EAC were implanted into the flank of a nude mouse and subsequently propagated. At the time of xenograft passage mice were sacrificed, and blood was collected through cardiac puncture. Tumors were cut into pieces and incubated in collagenase-containing buffer: 100 U/mL of collagenase type IV (Invitrogen), 50 µg/mL of DNase I (Roche), and 10% FBS in RPMI-1640 medium for 45 minutes. After incubation, cells were treated with red blood cell (RBC) lysis buffer and passed through a cell strainer to remove debris. The cell pellet was resuspended in 2% fetal calf serum in PBS and used for flow cytometry analysis. Isolated cells were stained with the LIVE/DEAD® Fixable Dead Cell Stain Kit (Invitrogen). Cells were subsequently stained with anti-PD-L2 antibody, PE isotype control, and anti-EpCAM (clone 9C4, Pacific Blue, Biolegend, #324218).

Flow cytometry was performed with a BD FACSCanto™ II flow cytometer equipped with BD FACSDiva™ software (BD Biosciences). The final analysis and graphical output were performed using FlowJo (TreeStar).

f. Statistical Analyses

All continuous data are presented as the mean±SEM and categorical data as proportions. Data were stratified by expression status for PD-1, PD-L1, PD-L2 and PD-1 co-expression with PD-L1 and PD-L2, and associations with patient demographics, comorbidity and tumor pathology were analyzed using two-tailed Student t-test and Pearson's chi-2 or Fisher's Exact test, where appropriate. Overall survival curves were estimated by the Kaplan-Meier method, stratified by PD-1, PD-L1, PD-L2 and PD-1 co-expression with PD-L1 and PD-L2 and compared by means of the log-rank test. Multivariate Cox proportional hazards analysis was used to control for other significant clinical prognostic factors. All p-values are two sided, and a p-value <0.05 was considered statistically significant. Analysis was performed using SPSS (version 20) and STATA 13.

Example 2: Esophageal Adenocarcinomas Commonly Express PD-L2 in Cancer Epithelial Cells PD-1, PD-L1, and PD-L2 protein expression were assayed in tissue microarrays (TMAs) containing cores from 354 esophageal adenocarcinomas (EACs) using antibodies optimized for formalin fixed paraffin embedded (FFPE) tissues (Shi et al. (2014) *Amer. J. Surg. Pathol.* 38:1715-1723; Chen et al. (2013) *Clin. Cancer Res.* 19:3462-3473). The PD-L2 assay was recently validated on FFPE human lymphoid tissues and shown to be a sensitive and specific assay for PD-L2 expression (Shi et al. (2014) *Amer. J. Surg. Pathol.* 38:1715-1723). Clinical and pathologic characteristics of the study population are listed in FIG. 5.

A strong majority (289/354, 81.6%) of EACs showed evidence of at least weak (1+) epithelial PD-L2 expression in 1 of the cores. In 51.7% (183/354) of EACs, we observed moderate-strong (2+/3+) PD-L2 epithelial expression in at least 1 core. In 19.8% (70/354) of EACs, all evaluated cores had moderate-strong PD-L2 staining (FIG. 1). Immune cells in the tumor microenvironment were negative for PD-L2. Due to the high frequency of weak epithelial PD-L2 expression, only moderate-strong PD-L2 expression was considered positive for further analyses.

Example 3: PD-L1 and PD-1 Expression in Stromal Inflammatory Cells

Tumor epithelial expression of PD-L1 was rare, observed in only 1.7% (6/344) of EACs. However, PD-L1+ inflammatory cells were observed in 18% (62/344) of EACs (FIG. 1). Morphologically, these PD-L1+ inflammatory cells appeared to be macrophages, which was confirmed by PD-L1 double staining with macrophage markers CD68 and CD163 on whole-tumor sections of 16 PD-L1 immune cell-positive EACs. PD-1 positive tumor infiltrating lymphocytes (TILs) were identified in 59.8% (215/349) of EACs. When present, the density of PD-1+ TILs varied from 1-181 per tissue core.

Example 4: Co-Expression of PD-L2, PD-L1, and PD-1

While PD-L2 and PD-L1 expression was not mutually exclusive, tumors with PD-L2 expression in all evaluated core were less likely to possess PD-L1+ immune cells (P=0.045). Both PD-L2+ and PD-L1+ tumors have a higher average number of PD-1+ TILs compared to tumors without PD-L2 or PD-L1 expression (7.2 vs 3.7, P=0.052 and 12.6 vs 2.5, P<0.001 respectively). In 15.5% (53/343) of EACS, no PD-L2+, PD-L1+, or PD-1+ cells was observed.

TMA results were validated using whole-tissue slides from 45 tumors. Expression of PD-L2 was confirmed in 27 of 30 cases that expressed PD-L2 on the TMA. Tumors with PD-L2 activity in all evaluated cores had a larger percentage of PD-L2+ cells (10/15 cases 70-100% of tumor cells positive) compared to tumors with 1 or 2 positive cores (12/16 cases 30-60% of tumor cells positive). Moreover, 6/14 tumors that had no PD-L2 expression on TMAs showed focal regions with PD-L2 expression, indicating that the total frequency of PD-L2 expression may be higher than suggested by TMA results. Similarly, evaluation of whole-tumor slices showed PD-L1+ immune cells in 16/45 (35.6%) whole-tissue sections, of which 7/16 were not identified on the TMAs, again indicating possible underestimation in TMAs due to heterogeneity. In 5/16 EACs, PD-L1+ immune cells were observed only at the tumor border, while PD-L1+ cells infiltrated the tumor in the remaining 11/16 patients. Whole-tissue sections confirmed focal epithelial PD-L1 positivity in only 2/45 patients.

Example 5: Validation of IHC Results

Figure 2:
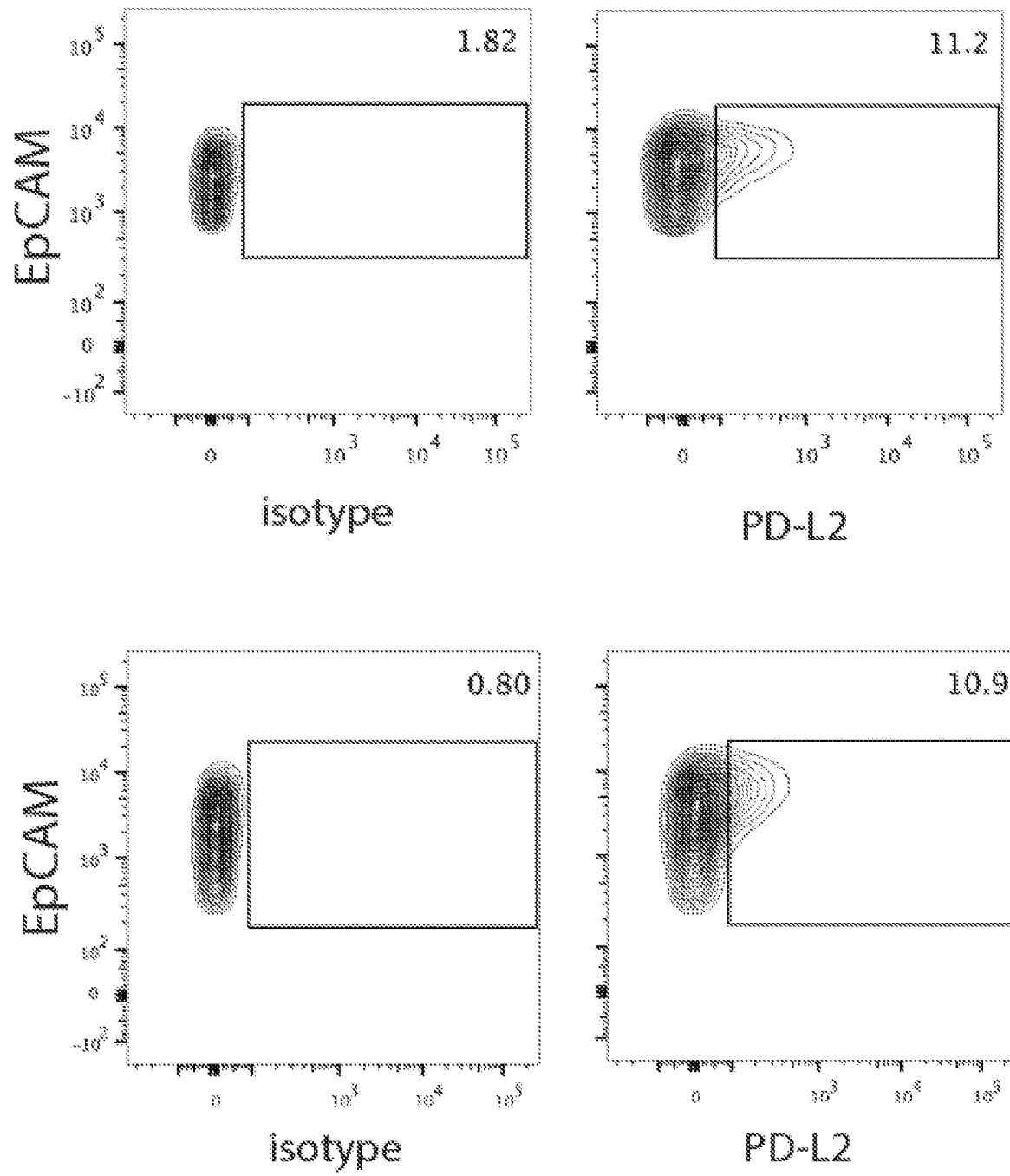
FIG. 2 includes 3 panels, identified as panels A, B, and C, which show validation of IHC results with flow cytometry. Panel A shows IHC and flow cytometry results of PD-L2 expressing OE33 and MKN7 cells and PD-L2 non-expressing ESO26 cells (black, isotype; white, PD-L2). Panel B shows PD-L2 mRNA expression in 7 gastro-esophageal cell lines. Data are depicted as mean+standard deviation. Panel C shows IHC staining of 2 EAC biopsies with anti-PD-L2 antibody (20×). Staining was scored strong (3+) positive for both tumors. Tumor biopsies were implanted in the flank of nude mice. At time of passage, tumors were disaggregated into single cell suspensions and analyzed. Flow cytometry shows co-expression of EpCAM and PD-L2 in 11.9% and 10.2% of EpCAM positive cells. PE-isotype was used as control. A representative experiment of 2 experiments is shown.

Since this is believed be the first study to report abundant and predominant PD-L2 expression in the epithelial cancer cells, validation of the IHC results was performed. PD-L2 epithelial expression in gastro-esophageal cell lines OE19, ESO26, OE33, OACM5.1C, FLO-1, KYAE-1, and MKN7 was queried by IHC, and PD-L2 positivity was identified in the OE33 and MKN7 lines (FIG. 2A). These IHC results were concordant with flow cytometry results using a distinct PD-L2 antibody and mRNA expression levels in fresh cells (FIGS. 2A-2B). As an additional validation of the PD-L2 expression analysis results, samples from recently developed patient-derived xenografts by flow cytometry were evaluated. An EpCAM/PD-L2 double-positive population in two PD-L2 IHC positive xenografts was identified, which further confirms PD-L2 epithelial expression in EAC and validating the IHC findings (FIG. 2C).

Example 6: PD-L2 Expression is Detected at the Transition of Reflux Esophagitis to Barrett's Esophagus and can be Induced by IL-4/IL-13

It was further hypothesized that PD-L2 epithelial expression may also occur in BE, the precursor to EAC. In order to confirm the hypothesis, samples with BE (n=21) and reflux esophagitis without BE (n=14) were obtained and the samples were evaluated for PD-L2 expression via IHC (FIG. 3A). While no reflux esophagitis samples exhibited PD-L2 expression, 42.8% (9/21) of BE cases showed PD-L2 epithelial expression. PD-L1 expression in epithelial or immune cells was not observed.

The onset of PD-L2 expression with development of BE raised the hypothesis that IL-4 or IL-13 expression, which accompanies the transition to BE, may contribute to PD-L2 induction. This hypothesis was tested using in vitro assays. Treatment of PD-L2+ cell lines, OE33 and MKN7, with exogenous IL-4 and IL-13 induced STAT6 phosphorylation and an increase in PD-L2 mRNA. For OE33, an increase in protein expression was observed by flow cytometry (FIGS. 3B-3C). In PD-L2 non-expressing cell lines, IL-4 and IL-13 increase PD-L2 mRNA expression in FLO-1 cells, but not for ESO26. In order to test if constitutive PD-L2 expression is dependent upon IL-4/IL-13/STAT6 signaling, STAT6 expression was knocked down in the PD-L2 expressing cell lines, OE33 and MKN7, and the knockdown did not lead to a change in PD-L2 mRNA or protein expression. The results indicate that Th2-related cytokines can induce PD-L2 expression in EAC cells and that other factors likely also influence the expression of this protein.

Figure 6:
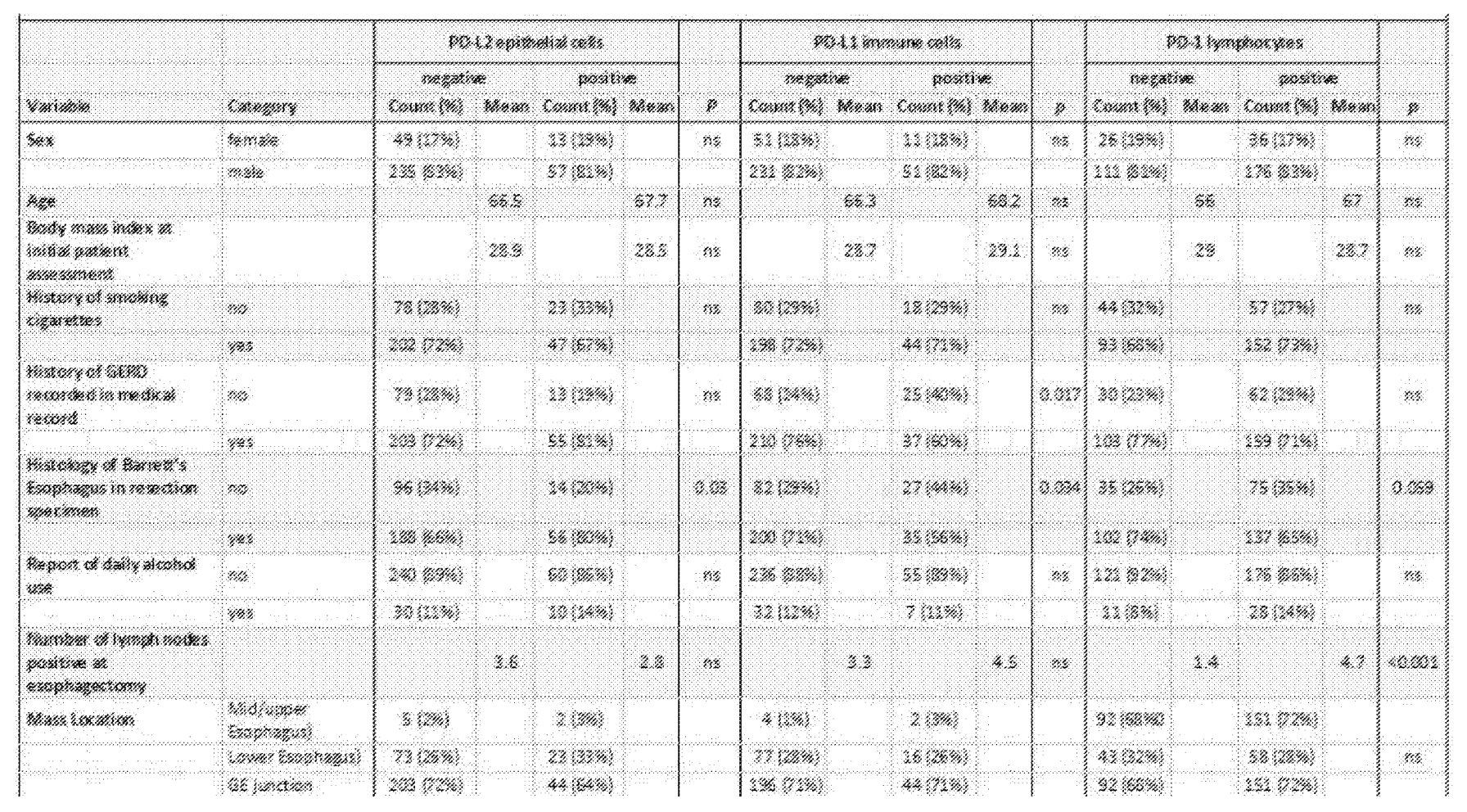
Figure 6:
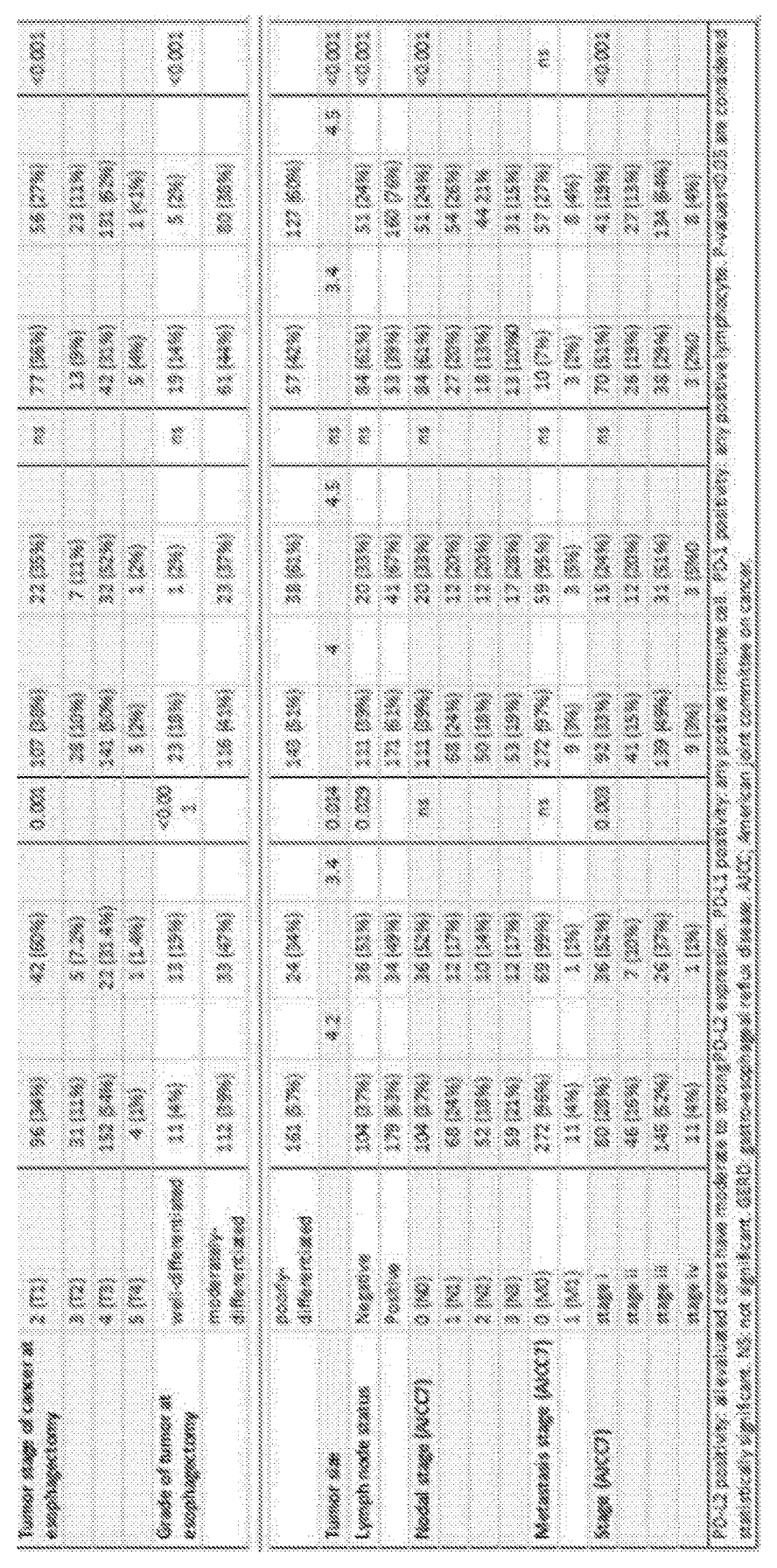

Example 7: Clinical and Pathologic Associations of PD-1 Pathway Member Expression in EAC Clinical correlates of PD-1, PD-L1, and PD-L2 expression were also analyzed. In tumors where all cores showed PD-L2 expression, PD-L2 expression was associated with early-stage disease (P=0.003), smaller tumor size (P=0.01), and a well-differentiated tumor grade (P<0.001) (FIGS. 4A and 6). Moreover, cancers with consistent PD-L2 expression were more likely to have evidence of BE in the resection sample (P=0.03). In contrast, PD-L1 expression was significantly enriched in those tumors lacking evidence of BE in the surgical resection (P=0.034) or lacking a clinical history of gastro-esophageal reflux disease (GERD) (P=0.017).

Tumors with PD-1+ TILs had a higher tumor stage (P<0.001), were more frequently poorly differentiated (P<0.001), and showed a trend towards an absence of BE (P=0.056). PD-1 positivity correlated with an increased mortality (univariate Cox regression HR=1.89 (95% CI 1.38-2.6), P<0.0001) (FIG. 4B). However, the negative association between PD-1 and mortality was lost after adjustment for other prognostic factors (e.g., age, tumor stage, and Charlson comorbidity score). PD-L2 expression showed a trend towards an improved outcome (univariate Cox regression HR=0.75; 95% CI 0.54-1.03; P=0.078). For PD-L1 expression, no association to survival was observed.

Thus, EAC is a highly lethal disease that lacks effective treatment once disseminated disease has emerged, making exploration of the targets of immune checkpoint inhibitors of clear importance. The results described herein represent the first systematic effort to characterize expression and clinical correlations of the PD-1 pathway in EAC. The results demonstrate that the vast majority of EACs harbor expression of at least one member of this pathway: expression of PD-1 itself on lymphoid cells or of the ligands PD-L2 on tumor epithelial cells or PD-L1 on immune cells. Given the heterogeneity in expression of these markers, the data support prediction of PD-1 pathway inhibitor efficacy in EAC results and may underestimate the frequency of expression of these markers in EAC. Moreover, the presence of PD-L2 expression may mark a scenario where inhibition of PD-1, a receptor for both PD-L1 and PD-L2, may have more efficacy than targeting PD-L1.

A surprising and unexpected finding was the observation that EACs commonly have epithelial PD-L2 expression. While PD-L1 has been described to occur commonly in epithelial cancer cells of various lineages (Topalian et al. (2012) *New Engl. J. Med.* 366:2443-2454; Brown et al. (2003) *J. Immunol.* 170:1257-1266), isolated PD-L2 expression has been recorded only for primary mediastinal large B-cell lymphoma (Shi et al. (2014) *Amer. J. Surg. Pathol.* 38:1715-1723). Although PD-L2 expression has been described in esophageal squamous cell carcinomas (Ohigashi et al. (2005) *Clin. Cancer Res.* 11:2947-2953), cervical carcinomas (Karim et al. (2009) *Clin. Cancer Res.* 15:6341-6347), and hepatocellular carcinomas (Wang et al. (2011) *World J. Gastroenterol.* 17:3322-3329) this was always in co-occurrence with PD-L1 epithelial expression. Also Epstein-Barr Virus-positive gastric cancers (The Cancer Genome Atlas Research Network (2014) *Nature* 513:202-209) have increased mRNA expression of both PD-L1 and PD-L2, which occurs in the setting of 9p24.1 amplification, the locus of both of these genes. However, these amplifications have been seen only rarely in EAC (Dulak et al. (2013) *Nat. Genet.* 45:478-486).

In macrophages and dendritic cells PD-L2 transcription is regulated by IL-4/IL-13/STATE signaling (Akbari et al. (2010) *Mucosal Immunol.* 3:81-91; Lesterhuis et al. (2011) *J. Clin. Invest.* 121:3100-3108). Pertinent to the results described herein, EACs develop in a background of chronic inflammation and typically emerge from Barrett's esophagus (BE), itself a tissue type with a documented Th2 skewed inflammatory state with increased 11-4 expression (Fitzgerald et al. (2002) *Gut* 51:316-322; Moons et al. (2005) *J. Pathol.* 207:269-276). PD-L2 epithelial expression in EAC and BE may indeed be a consequence of Il-4/IL-13 expression in the immune microenvironment (Gao et al. (2014) *PloS One* 9:e104453).

The finding of PD-L2 expression in EACs with an association with PD-1 positive TILs and BE indicates that PD-L2 may be a component of a larger chronic inflammatory microenvironment that may facilitate tumor survival. Recent studies have shown that Th2 polarization in esophageal cancer is associated with the infiltration of myeloid-derived suppressor cells (MDSCs) and M2-polarized macrophages (Gao et al. (2014) *PloS One* 9:e104453; Gabitass et al. (2011) *Cancer Immunol. Immunotherap.* 60:1419-1430), illustrating the complexity of the Th2-skewed immune suppressive state.

The identification of PD-L2 as a biomarker for esophagogastric cancer response to PD-1 pathway inhibitors is also unexpected because of the controversial role of PD-L2 in inhibiting T-cell responses. As PD-L1 and PD-L2 show structural similarity, it has been assumed that expression of PD-L1 and PD-L2 by tumor cells are functionally interchangeable mechanisms of immune evasion. However, each has alternative secondary receptors, RGMb for PD-L2 (Xiao et al. (2014) *J. Exp. Med.* 211:943-959) and CD80 for PD-L1 (Butte et al. (2007) *Immunity* 27:111-122). While a number of studies show an inhibitory role for PD-L2 (Latchman et al. (2001) *Nat. Immunol.* 2:261-268; Zhang et al. (2006) *Proc. Natl. Acad. Sci. U.S.A.* 103:11695-11700), several studies suggest that PD-L2 can also stimulate T-cell proliferation and cytokine production (Shin et al. (2003) *J. Exp. Med.* 198:31-38; Wang et al. (2003) *J. Exp. Med.* 197:1083-1091) via a PD-1-receptor independent mechanism, potentially involving a distinct PD-L2 binding partner.

Beyond PD-L2 expression, PD-L1-positive immune cells were also identified in 18%-36% of EACs. The data suggest an intriguing hypothesis that PD-L1 expression may predominate in tumors with a different inflammatory infiltrate than PD-L2-predominant tumors. PD-L1 expression is strongly induced by the Th1 cytokine IFN-γ, while PD-L2 is only weakly induced, raising the hypothesis that PD-L1 positive tumors emerge in the setting of a Th1-type acute inflammation which may predominate in tumors that emerge without antecedent BE.

Thus, the results described herein demonstrate that the majority of EACs show evidence of PD-1 pathway activity. These data indicate the capacity of both PD-L1 and PD-L2 to serve as biomarkers of response. Furthermore, in PD-L2 positive tumors, the presence of secondary mechanisms of immune evasion, such as the presence of M2 macrophages, may also impact response to therapies, potentially leading to tumors where combination immunotherapeutic approaches may be especially beneficial.

Example 8: Esophagogastric Cancer Cell Expression of PD-L2 Inhibition of T Cell Function and Relief Thereof Through PD-1 Pathway Blockade Using Inhibitors to Reactivate Anti-Esophagogastric Cancer Responses It is believed that the expression of PD-L2 by esophagogastric cancer cells leads to down-regulation of the activity of cytotoxic T cells and that blockade of the PD-1 pathway in the esophagogastric cancer microenvironment will reactivate anti-esophagogastric cancer responses. In addition, it is believed that other cells in the esophagogastric cancer cell microenvironment modulate the effect of PD-L2 and the PD-1 pathway such that blockade of related immune checkpoints and/or enhancement of immune costimulatory pathways will increase the efficacy of PD-1 pathway blockade.

In order to confirm that PD-L2 expression on esophagogastric cancer cells, such as esophageal adenocarcinoma cells, functionally inhibit cytotoxic T cells, the activity of PD-L2 upon PD-1+ cytotoxic T lymphocytes (CTLs) using EAC cell line models is used. For example, EAC cell lines identified via flow cytometry to exhibit basal cell surface PD-L2 expression (MKN7 and OE33) can be used. With these models, PD-L2 expression levels are modulated by generating sub-derivations with elimination of PD-L2 expression by CRISPR-mediated deletion of the gene. Additionally, assays based on ectopic expression of PD-L2 (and matched controls with expression of vector only) in EAC cell lines that lack basal PD-L2 expression (OE19, ESO26) can be performed.

In order to study the effect of the EAC models upon PD-1+ CTLs, PD-1+ CTLs (obtained from peripheral blood of EAC patients) ex vivo are obtained and cultured and the cells are examined for production of cytokines (IL-2 and IFN-γ), proliferation, and cytotoxic capacity when co-cultured with EAC cell lines with differing levels of PD-L2 expression. If needed, an alternative source of CTLs, whereby human CD8+ T cells from EAC patients' peripheral blood are transfected with PD-1-encoding mRNA, are used. Determination of PD-L2-positive EAC cell delivery of inhibitory or stimulatory signals to PD-1+ T cells by co-culturing PD-1+ CTLs with the isogenic EAC cell lines with and without PD-L2 expression is made. Activity of CTLs are assayed using target cell killing assays, measurements of T cell viability, proliferation, and cytokine response (e.g., IL-2, IFN-γ, and the like) (Xu et al. (2014) Cancer Cell 25:590-604; Xiao et al. (2014) J. Exp. Med. 211:943-959; Iwai et al. (2002) Proc. Natl. Acad. Sci. U.S.A. 99:12293-12297). It is believed that PD-L2 attenuates CTL activation. Determination of reversibility of any inhibitory effect of PD-L2-positive EAC upon CTLs is made by adding PD-L2 monoclonal antibodies that specifically block the interaction between PD-L2 and PD-1 (Xiao et al. (2014) J. Exp. Med. 211:943-959).

It is also evaluated whether pharmacologic blockade of PD-1 modifies the effect of PD-L2-positive epithelial cells upon CTLs. It is believed that PD-L2-positive EAC cells directly bind to PD-1+ T cells and this is determined using an established cell conjugation assay (Xiao et al. (2014) J. Exp. Med. 211:943-959). The conjugation assay and the additional assays of CTL activity are repeated when CTLs are co-cultured with isogenic EAC cell line systems both with and without the addition of PD-1 blocking antibody and a PD-L2 monoclonal antibody that specifically blocks the interaction between PD-L2 and PD-1 (Xiao et al. (2014) J. Exp. Med. 211:943-959).

It is believed that exposure of CTLs to PD-L2-positive EAC cells results in a change of cytokine response characterized by a reduction of IL-2, TNF, and IFN-γ secretion into the culture medium, accompanied by a reduction in cytotoxicity and proliferation. It is further believed that the use of PD-1-blocking antibodies greatly attenuates the effects of PD-L2 upon CTL inhibition.

In addition, various cancers use immunomodulatory pathways other than the PD-1 immunosuppressive pathway as immune escape pathways, as well as different cell types, such as tumor-promoting macrophages and immunosuppressive myeloid cell populations to specific regulatory T cell populations (Tregs), to downregulate anti-cancer immune responses (Duraiswamy et al. (2013) Cancer Res. 73:6900-6912). It is believed that PD-L2 expression in esophagogastric cancers emerges in the context of a Th2-type chronic inflammatory state that has other immunosuppressant features such that the PD-L2-positive tumor microenvironment also harbors M2 macrophages, MDSCs, and regulatory T cells that exhibit intrinsic T cell inhibitory effects. Thus, it is believed that combinations of PD-1 pathway blockade in addition to inhibition of one or more additional immune checkpoints or other immune suppression pathways and/or cell types is beneficial.

Pilot assays on gastroesophageal cancers have been performed where distinct cell populations from gastroesophageal cancers have been sorted and assayed via multiplexed flow cytometry for the expression of distinct markers to define the details of these cell components. Additional studies to characterize the immune features of esophagogastric cancers are performed by characterizing the immune subpopulations in the microenvironment of PD-L2-positive and PD-L2-negative cancer cells using freshly obtained biopsy samples. For instance, tumors spanning cases with and without PD-L2 expression are disaggregated immediately following removal from the patient. Part of the single cell suspension is used to characterize the type and phenotype of immune subpopulations via flow cytometry. Adaptive immune cells (B cells, Th1-2/regulatory/memory/cytotoxic T cells) and innate immune cells (dendritic cells, eosinophils, mast cells, M1 and M2 macrophages, NK cells, MDSCs, and neutrophils) in PD-L2-positive and PD-L2-negative tumors are analyzed. In follow up of identification of common cell populations via flow cytometry, the spatial organization of these inflammatory cell populations in the tumor with the use of immunohistochemistry in untreated surgical samples is analyzed.

It is believed that distinct, co-existing features of PD-L2-expressing esophagogastric cancer cells, including the presence of distinct immunosuppressive macrophage populations, potentially Treg cells, and other features, exist such that combination therapy with one or more PD-1 pathway inhibitors with one or more inhibitors of immune suppressive pathways and/or cell types further augments anti-cancer immune responses.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web and/or the National Center for Biotechnology Information (NCBI) on the world wide web.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A method of treating an esophagogastric adenocarcinoma in a subject likely to be responsive to a PD-1 pathway inhibitor, the method comprising
   a) measuring the copy number, amount, or activity of PD-L2 in a subject sample obtained from a subject having esophagogastric adenocarcinoma;
   b) comparing the copy number, amount, or activity of PD-L2 in a control sample, and determining a significantly increased copy number, amount, or activity of PD-L2 in the subject sample relative to the control sample thereby identifying the esophagogastric adenocarcinoma as being likely to be responsive to the PD-1 pathway inhibitor; and
   c) administering the PD-1 pathway inhibitor to the subject likely to be responsive to the PD-1 pathway inhibitor.

2. The method of claim 1, further comprising recommending, prescribing, or administering at least one additional anti-cancer therapy.

3. The method of claim 1, wherein the control sample is derived from an esophagogastric adenocarcinoma cancerous sample or non-cancerous esophagogastric sample from either the subject or a member of the same species to which the subject belongs.

4. The method of claim 1, wherein the subject sample and/or the control sample has not been contacted with any anti-esophagogastric adenocarcinoma treatment or PD-1 pathway inhibitor, or wherein the subject has not been administered any anti-esophagogastric adenocarcinoma treatment or PD-1 pathway inhibitor.

5. The method of claim 2, wherein the at least one additional anti-cancer therapy is an immune checkpoint inhibitor.

6. The method of claim 1, wherein the amount of PD-L2 is detected using a reagent which specifically binds with PD-L2.

7. The method of claim 1, wherein PD-L2 is assessed by detecting the presence of a transcribed polynucleotide or portion thereof.

8. The method of claim 1, wherein the PD-1 pathway inhibitor comprises at least one antibody selected from the group consisting of anti-PD-1 antibodies, anti-PD-L1 antibodies, anti-PD-L2 antibodies, and combinations thereof.

9. The method of claim 1, wherein the esophagogastric adenocarcinoma is an esophageal adenocarcinoma, or a gastric adenocarcinoma.

10. The method of claim 1, wherein the subject is a mammal.

11. The method of claim 1, wherein the control sample comprises cells or does not comprise cells; or wherein the control sample comprises esophagogastric adenocarcinoma cells known to be responsive or non-responsive to the PD-1 pathway inhibitor.

12. The method of claim 1, wherein the subject sample is selected from the group consisting of serum, whole blood, plasma, urine, cells, cell lines, resected tissue, and biopsies.

13. The method of claim 1, wherein the esophagogastric adenocarcinoma in the subject is responsive to PD-1 pathway inhibitor in at least one criteria selected from the group consisting of cellular proliferation, tumor burden, m-stage, metastasis, progressive disease, clinical benefit rate, survival until mortality, pathological complete response, semi-quantitative measures of pathologic response, clinical complete remission, clinical partial remission, clinical stable disease, recurrence-free survival, metastasis free survival, disease free survival, circulating tumor cell decrease, circulating marker response, and RECIST criteria.

14. The method of claim 2, wherein the anti-cancer therapy is selected from the group consisting of targeted therapy, chemotherapy, radiation therapy, and/or hormonal therapy.

15. The method of claim 1, wherein the control sample is a cancerous esophagogastric adenocarcinoma or non-cancerous esophagogastric sample from the subject obtained from an earlier point in time than the subject sample; and/or wherein the control sample is obtained before the subject has received PD-1 pathway inhibitor therapy and the subject sample is obtained after the subject has received PD-1 pathway inhibitor therapy.

16. The method of claim 6, wherein the reagent is selected from the group consisting of an antibody, an antibody derivative, and an antibody fragment.

17. The method of claim 7, wherein the transcribed polynucleotide is an mRNA or a cDNA.

18. The method of claim 17, wherein the step of detecting further comprises amplifying the transcribed polynucleotide, and/or wherein the transcribed polynucleotide is detected by identifying a nucleic acid that anneals with the biomarker nucleic acid, or a portion thereof, under stringent hybridization conditions, wherein the stringent hybridization conditions are hybridization in 6× sodium chloride/sodium citrate (SSC) at about 45° C. followed by one or more washes in 0.2×SSC, 0.1% SDS at 50-65° C.

19. The method of claim 8, wherein the PD-1 pathway inhibitor comprises an anti-PD-L2 antibody.

20. The method of claim 9, wherein the esophageal adenocarcinoma is metastatic.

21. The method of claim 10, wherein the mammal is a human, or an animal model of an esophagogastric adenocarcinoma.

* * * * *